US006410221B1

(12) United States Patent
Moyer et al.

(10) Patent No.: US 6,410,221 B1

(45) Date of Patent: *Jun. 25, 2002

(54) ENTOMOPOXVIRUS EXPRESSION SYSTEM

(75) Inventors: Richard W. Moyer; Richard L. Hall, both of Gainesville; Michael E. Gruidl, Tampa; Yi Li, Gainesville, all of FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/370,861

(22) Filed: Aug. 9, 1999

Related U.S. Application Data

(63) Continuation of application No. 08/544,332, filed on Oct. 17, 1995, now Pat. No. 5,935,777, which is a continuation-in-part of application No. 08/107,755, filed on Nov. 22, 1993, now Pat. No. 5,721,352, which is a continuation-in-part of application No. 07/991,867, filed on Dec. 7, 1992, now Pat. No. 5,476,781, which is a continuation-in-part of application No. PCT/US92/00855, filed on Feb. 12, 1992, now Pat. No. 5,721,352, which is a continuation-in-part of application No. 07/827,685, filed on Jan. 30, 1992, now abandoned, which is a continuation-in-part of application No. 07/657,584, filed on Feb. 19, 1991, now abandoned.

(51) Int. Cl.$^7$ .......................... C12Q 1/68; C12Q 1/70; C12N 15/863; C12N 5/10

(52) U.S. Cl. .................... 435/5; 435/320.1; 435/235.1; 435/69.1; 435/6; 435/325; 435/348; 536/23.1; 536/23.2; 536/23.4; 536/23.72; 536/24.1; 536/24.3

(58) Field of Search .......................... 435/320.1, 235.1, 435/69.1, 5, 6, 325, 348; 424/199.1, 202.1; 536/23.1, 23.2, 23.72, 24.1, 24.3, 23.4

(56) References Cited

U.S. PATENT DOCUMENTS

| | | | | |
|---|---|---|---|---|
| 4,338,397 A | | 7/1982 | Gilbert et al. | 435/69.1 |
| 4,722,848 A | | 2/1988 | Paoletto et al. | 424/199.1 |
| 4,745,051 A | | 5/1988 | Smith et al. | 435/69.51 |
| 5,338,679 A | | 8/1994 | Yuen et al. | 435/235.1 |
| 5,476,781 A | * | 12/1995 | Moyer et al. | 435/348 |
| 5,935,777 A | * | 8/1999 | Moyer et al. | 435/5 |

FOREIGN PATENT DOCUMENTS

| | | |
|---|---|---|
| EP | 0261925 | 3/1988 |
| EP | 0397560 | 11/1990 |

OTHER PUBLICATIONS

Roberts, D.W., R.R. Granados (1968) "A Poxlike Virus from *Amsecta moorei*" *J. Invertebr. Pathol.* 12:141–143.

Granados, R.R., M. Naughton (1976) "Replication of *Amsacta moorei* Entomoxpoxvirus and *Autographa californica* Nuclear Polyhedrosis Virus in Hemocyte Cell Lines from *Estigmene acrea*" Invert. Tissue Culture App. in Medicine, Biology and Agriculture 379–389.

Hukuhara, Tosihiko et al. (1990) "Replication of an Entomopoxvirus in Two Lepidopteran Cell Lines" *Journal of Invertebrate Pathology* 56:222–232.

Sato, Takeru (1989) "Establishment of Eight Cell Lines from Neonate Larvae of Torticids (Lepidoptera) and Their Several Characteristics including Susceptibility to Insect viruses" *Invertebrate Cell Systems Application* 11:187–198.

Langridge, W.H.R. et al. (1977) "The Base Composition of Entomopoxvirus DNA" *Virology* 76:616–620.

Hall, R.L., W.F. Hink (1990) "Physical mapping and field inversion gel electrophoresis of *Amsacta moorei* entomopoxvirus DNA" *Arch. Virol.* 110:77–90.

Cohen, S.N. (1975) "The Manipulation of Genes" *Scientific American* 233:23–33.

Funahashi, S. et al. (1988) "Cloning and Characterization of the Gene Encoding the Major Protein of the A–type Inclusion Body of Cowpox Virus" *J. Gen. Virol.* 69:35–47.

Gilbert, W., L. Villa–Komaroff (1980) "Useful Proteins from Recombinant Bacteria" *Scientific American* 242:74–94.

Goeddel, D.V. et al. (1980) "Synthesis of human fibroblast interferon by *E. coli*" *Nucleic Acids Research* 8(18):4057–4074.

Gruidl, M.E. et al. (1992) "Mapping and Molecular Characterization of a Functional Thymidine Kinase from *Amsacta moorei* Entomopoxvirus" *Virology* 186:507–516.

Hall, R.L., R.W. Moyer (1991) "Identification, cloning, an Sequencing of a Fragment of *Amsacta moorei* Entomopoxvirus DNA Containing the Spheroidin Gene and Three Vaccinia Virus–Related Open Reading Frames" *Journal of Virology* 65(12):6516–6527.

Hitzeman, R.A. et al. (1983) "Secretion of Human Interferons by Yeast" *Science* 219:620–625.

Hull, R. et al. (199) Virology–Director and Dictionary of Animal, Bacterial and Plant Viruses, pp. 70, 71, 178, 274–276.

Kasza, L. et al. (1960) "Isolation and Cultivation of Swine Pox Virus in Primary Cell Cultures of Swine Origin" *Am. J. Vet. Res.* 23:269–273.

Kasza, L., R.A. Griesemer (1962) "Experimental Swine Pox" *Am. J. Vet. Res.* 23:443–450.

Langridge, W.H.R. (1983) "Virus DNA Replication and Protein Synthesis in *Amsacta moorei* Entomopoxvirus–Infected *Estigmene acrea* Cells" *Journal of Invertebrate Pathology* 41:341–349.

(List continued on next page.)

*Primary Examiner*—David Guzo

(74) *Attorney, Agent, or Firm*—Saliwanchik, Lloyd & Saliwanchik

(57) ABSTRACT

The subject invention pertains to novel Entomopoxvirus (EPV) polynucleotide sequences free from association with other viral sequences with which they are naturally associated, recombinant polynucleotide vectors containing the sequences, recombinant viruses containing the sequences, and host cells infected with the recombinant viruses are provided herein, as well as methods for use thereof in the expression of heterologous proteins in both insect and mammalian host cells.

10 Claims, 32 Drawing Sheets

OTHER PUBLICATIONS

Langridge, W.H.R. (1983) "Partial Characterization of DNA from Five Entomopoxviruses" *Journal of Invertebrate Pathology* 42:369–375.

Luckow, V.A., M.D. Summers (1988) "Trends in the Development of Baculovirus Expression Vectors" *Bio/Technology* 6:47–55.

Massung, R.F., R.W. Moyer (1991) "The Molecular Biology of Swinepox Virus–1. A Characterization of the Viral DNA" *Virology* 180:347–354.

Massung, R.F., R.W. Moyer (1991) "The Molecular Biology of Swinepox Virus–II. The Infectious Cycle" *Virology* 180:355–364.

Miyanohara, A. et al. (1983) "Expression of hepatitis B surface antigen gene in yeast" *Proc. Natl. Acad. Sci. USA* 80:1–5.

Mory, Y et al. (1981) "Synthesis of Human Interferen $\beta_1$ in *Escherichia coli* infected by a Lambda Phage Recombinant Containing a Human Genomic Fragment" *Eur. J. Biochem.* 120:197–202.

Pearson, A. et al. (1991) The 5' Noncoding Region Sequence of the *Choristoneaura biennis* Entomopoxvirus Spheroidin Gene Functions as an Efficient Late Promoter in the Mammalian Vaccinia Expression System: Virology 180:561–566.

Taniguchi, T. et al. (1980) "Expression of the human fibroblast interferon gene in *Escherichia coli*" *Proc. Natl. Acad. Sci. USA* 77(9):5230–5233.

Upton, C. G. McFadden (1986) "Identification and Nucleotide Sequence of the Thymidine Kinase Gene of Shope Fibroma Virus" *Journal of Virology* 60(3):920–927.

Williams, P.P. et al. (1985) "Experimental Exposure of Partially Histocompatible Miniature Pigs to Swine Poxvirus: Lymphocyte Transformation Responses" *Amer. Assn. Veterinary Laboratory*.

Arif, B.M., E. Kurstak (1991) "The Entomopoxviruses" Viruses of Invertebrates, Chapter 6, pp. 179–195.

Banville, M. et al. (1992) "The predicted amino acid sequence of the spheroidin protein from *Amsacta moorei* entomopoxvirus: lack of homology between major occlusion body proteins of different poxviruses" *Journal of General Virology* 73:559–566.

Goodwin, R.H. et al. (1991) "Entomopoxvirinae" Atlas of Invertebrate Viruses, Chapter 8, pp. 259–285.

Gruidl, M.E. et al. (1992) "Mapping and Molecular Characterization of a Functional Thymidine Kinase from *Armsacta moorei* Entomopoxvirus" *Virology* 186:507–516.

Hall, R.L., R.W. Moyer (1991) "Identification, Cloning, and Sequencing of a Fragment of *Amsacta moorei* Entomopoxvirus DNA Containing the Spheroidin Gene and Three Vaccinia Virus–Related Open Reading Frames" *Journal of Virology* 65(12):6516–6527.

Hunkapillar, M.W., L.E. Hood (1980) "New Protein Sequenator with Increased Sensitivity" *Science* 207:523–525.

Sambrook et al. (1989) "Synthetic Oligonucleotide Probes" Molecular Cloning: A Laboratory Manual, Chapter 11, pp. 11.1–11.19.

Vialard, J.E. et al. (1990) "Identification and Characterization of a Baculovirus Occlusion Body Glycoprotein Which Resembles Spheroidin, an Entomopoxvirus Protein" *Journal of Virology* 64(12):5804–5811.

Langrideg, W. H. R. (1983) "Detection of *Amsacta moorei* Entomopoxvirus and Vaccinia Virus Proteins in Cell Cultures Restrictive for Poxvirus Multiplication" *Journal of Invertebrate Pathology* 42:77–82.

Langridge, W. H. R. (1984) "Detection of DNA Base Sequence Homology Between Entomopoxvirus isolated from Lepidoptera and Orthoptera" *J. Invert. Path.* 43:41–46.

Langridge, W. H. R. (1982) "Structural Proteins of *Amsacta moorei, Euxoa auxiliaris*, and *Melanoplus sanguinipes* Entomopoxviruses" *J. Invert. Path.* 39: 346–353.

Mackett, Michael et al. (1985) "The Construction and Characterisation of Vaccinia Virus Recombinants Expressing Foreign Genes" DNA Cloning II:191–212.

Panicalli, Dennis et al., (1982) "Construction of live vaccines by using genetically engineered poxviruses: Biological activity of recombinant vaccinia virus expressing influenza virus hemagglutinin" *Proc. Natl. Acad. Sci.* USA 80:5364–5368.

Paoletti, Enzo et al. (1984) "Construction of live vaccines using genetically engineered poxviruses: Biological activity of vaccinia virus recombinants expressing the hepatitus B virus surface antigen and the herpes simplex virus glycoprotein D" *Proc. Natl. Acad. Sci.* USA 81:193–197.

Piccini, A., E. Paoletti (1966) "The Use of Vaccinia Virus for the Construction of Recombinant Vaccines" BioEssays 5:248–252.

Yuen. Leonard et al. (1990) "Identification and Sequencing of the Spheroidin Gene of Choristoneura biennis Entomopoxvirus" *Virology* 175:427–433.

BRL Catalog (1985/86) Bethesda Research Laboratories, Gaithersburg, MD, p. 51.

Arif, B.M. (1984) "The Entomopoxviruses" *Advances in Virus Research* 29:195–213.

Bilimoria, S.L., B.M. Arif (1979) "Subunit Protein and Alkaline Protease of Entomopoxvirus Spheroids" Virology 96:596–603.

Chakrabarti, S. et al. (1985) "Vaccinia Virus Expression Vector: Coexpression of β–Galactosidase Provides Visual Screening of Recombinant Virus Plaques" *Molecular and Cellular Biology* 5(12):3403–3409.

* cited by examiner

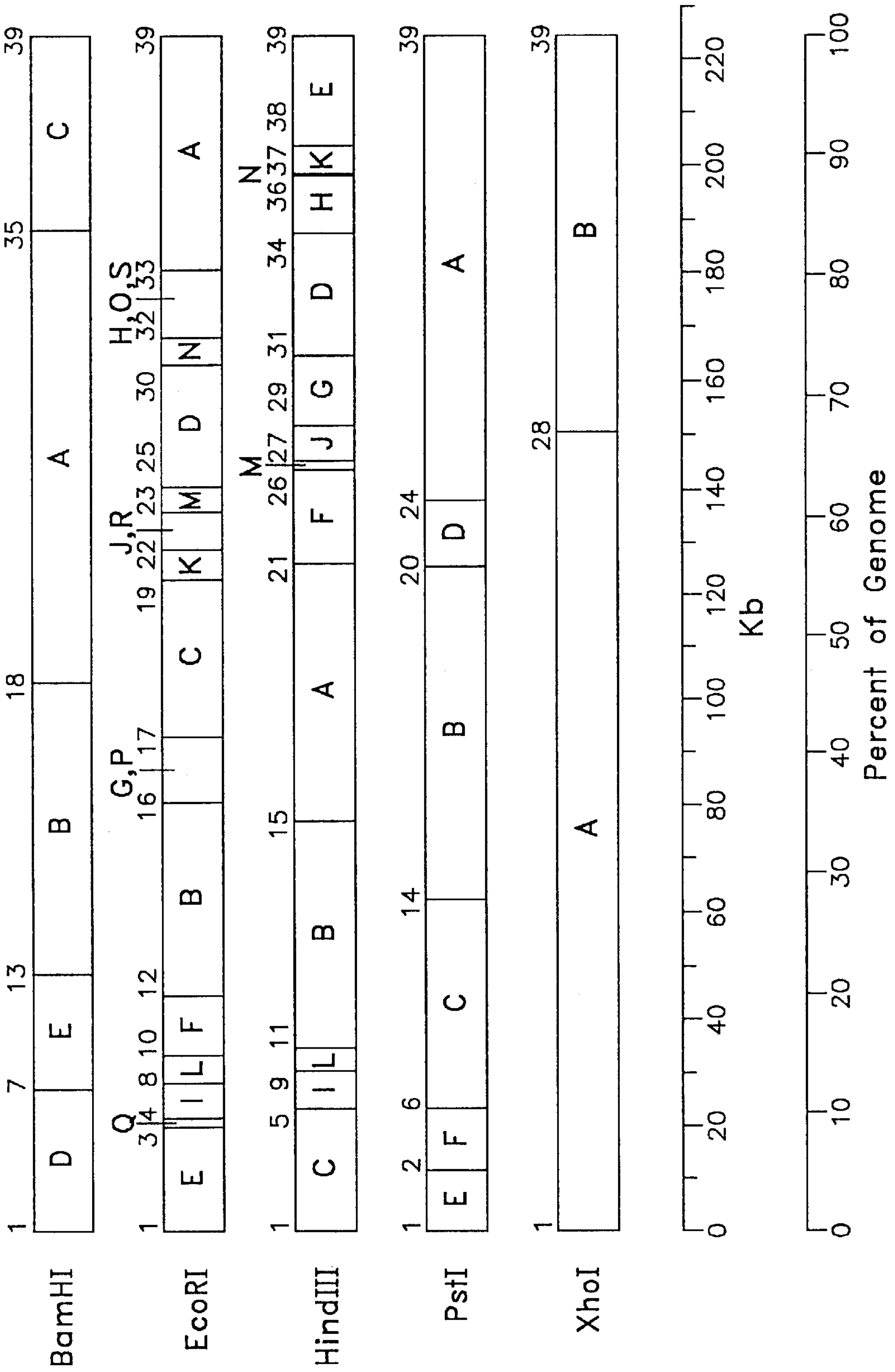
Fig. I

Fig. 2A

```
AGATCTGATG TTCTATATAT AGTACAAATT TGTATGATTA ATTGATATTT TAAAATTCAA      60

GATA TTA AAT ATT AGA TTC TAA ACT ATT CTT CTC ATT ATC AAT ATA ACT      109
         Ile Asn Ser Glu Leu Ser Asn Lys Glu Asn Asp Ile Tyr Ser
          1              5                  10

ATC ATA ATC ATT TTT TAT TTT ACT ACA TAC ATT CAT AAT TCT ATT ACT ATT   160
Asp Tyr Asp Asn Lys Ile Lys Ser Cys Val Asn Met Ile Arg Asn Ser Asn
 15                  20                  25                  30

TTT TTT ATA CAT ATC TAT TAA TTC CAT AAA CTT TTT ATT TTT TAT ATT AAA   211
Lys Lys Tyr Met Asp Ile Leu Glu Met Phe Lys Lys Asn Lys Ile Asn Phe
             35                  40                  45

TAT TTC TAA TGT ATT TTT AAA TTC GTC AAT ACT ATT AAT ATC ATA TCT AGA   262
Ile Glu Leu Thr Asn Lys Phe Glu Asp Ile Ser Asn Ile Asp Tyr Arg Ser
     50                  55                  60                  65

AAT AAA TAA TGC ACC TCT ATA ACT ACT AGC CAA TAA ATC ACC AAT AAA ACT   313
Ile Phe Leu Ala Gly Arg Tyr Ser Ser Ala Leu Leu Asp Gly Ile Phe Ser
                 70                  75                  80

CAT AGA ATA ATA TAA TTT TTT AAA TTC AAA TTT AGA TTT TAT GTT GAA ATA   364
Met Ser Tyr Tyr Leu Lys Lys Phe Glu Phe Lys Ser Lys Ile Asn Phe Tyr
         85                  90                  95

AAC TAT ATA ATA TAA AAA TAT TAT ATT AAA CAT ACC ACA ATC GGG ACT ATC   415
Val Ile Tyr Tyr Leu Phe Ile Ile Asn Phe Met Gly Cys Asp Pro Ser Asp
100                 105                 110                 115
```

Fig. 2B

```
ATA TTG TAA TTC AAA AGT ATT AAA AAA GTA ATA ATT TAC ATT TTT AAA TAT   466
Tyr Gln Leu Glu Phe Thr Asn Phe Phe Tyr Tyr Asn Val Asn Lys Phe Ile
            120                 125                 130

ATC ATT TAA ATA TTC TGA TAG TAC ATC AAT GTA TAA ATA AGC ATA ATT AGT   517
Asp Asn Leu Tyr Glu Ser Leu Val Asp Ile Tyr Leu Tyr Ala Tyr Asn Thr
    135                 140                 145                 150

ATT AGG AGT ACT ATT GTA GTG TTT ATG GCT TTT TAT AGT CAT ATC AGA TTC   568
Asn Pro Thr Ser Asn Tyr His Lys His Ser Lys Ile Thr Met Asp Ser Glu
                155                 160                 165

AAT AAA CAT ATA TTT TTT ATT TTG TTT TAT AAG TTC TGG TAT ATA ACC ACT   619
Ile Phe Met Tyr Lys Lys Asn Gln Lys Ile Leu Glu Pro Ile Tyr Gly Ser
        170                 175                 180

ACT ATT AAA AAA GTA TGC AGC TTT TTT ATC TTT ATC AAA GTG TTT ATC TAT   670
Ser Asn Phe Phe Tyr Ala Ala Lys Lys Asp Lys Asp Phe His Lys Asp Ile
185                 190                 195                 200

TAC GCA ACA AGT AAA ATG ATC ATT ATA AAT TAT AGG AAA CAT AAA AAA TCT   721
Val Cys Cys Thr Phe His Asp Asn Tyr Ile Ile Pro Phe Met Phe Phe Arg
            205                 210                 215

TTT TTT ATC ATT CAT TAA AAA AAA TTT TAC TCT ATC TTC AAG TTT ATA GCA   772
Lys Lys Asp Asn Met Leu Phe Phe Lys Val Arg Asp Glu Leu Lys Tyr Cys
    220                 225                 230                 235
```

Fig. 2C

```
TCT CAT AGA TGA AGC TAC TGT AGC AAT ATT TTT ATC AGT TTT TTC AAA TAA    823
Arg Met Ser Ser Ala Val Thr Ala Ile Asn Lys Asp Thr Lys Glu Phe Leu
                240                 245                 250

AAT CAA ATG AAA ATA ATC ATA ATC TGT ATT AAT CAT AGT TAA TGG ATA TAT    874
Ile Leu His Phe Tyr Asp Tyr Asp Thr Asn Ile Met Thr Leu Pro Tyr Ile
        255                 260                 265

ACA ATT ATA TAT ATC TCC CGA ACT TAA CCA TGT AGA TTT ATC ATG TTT TCT    925
Cys Asn Tyr Ile Asp Gly Ser Ser Leu Trp Thr Ser Lys Asp His Lys Arg
270                 275                 280                 285

TGG GTA AGC TTT AGG TTT AGG ATT AAA TCC CAA AGG CGG TAT TCC TAT TTG    976
Pro Tyr Ala Lys Pro Lys Pro Asn Phe Gly Leu Pro Pro Ile Gly Ile Gln
            290                 295                 300

AGC ATC CAA ATC ATC ATA AAT TGT GGC AAA TGT AGA AAA ATC TCT TGT TTT   1027
Ala Asp Leu Asp Asp Tyr Ile Thr Ala Phe Thr Ser Phe Asp Arg Thr Lys
    305                 310                 315                 320

GGA TAA TTC TGA TTT TAG AAA AGA CTT TCT CAT ATA TAC TAA TGG AAT GCC   1078
Ser Leu Glu Ser Lys Leu Phe Ser Lys Arg Met Tyr Val Leu Pro Ile Gly
                325                 330                 335

TTT ATA TTT TTT AGA TGT AAT AAA AGT ATT AAT ATT TAT ATT TTT ATC TTG   1129
Lys Tyr Lys Lys Ser Thr Ile Phe Thr Asn Ile Asn Ile Asn Lys Asp Gln
        340                 345                 350
```

Fig. 2D

```
TAA ATA TTT TTT TAT AGT CCA AAA TAG AAA AAA TTT TCT TTT AAT ATT ATT   1180
Leu Tyr Lys Lys Ile Thr Trp Phe Leu Phe Phe Lys Arg Lys Ile Asn Asn
355                 360                     365                 370

TTC AAA ATT AAT ATT ATT AAT ATG ATT TGG ATC TAA AAC TAA TTC ATT ATA   1231
Glu Phe Asn Ile Asn Asn Ile His Asn Pro Asp Leu Val Leu Glu Asn Tyr
            375                 380                 385

TAA TAT TTC CAA GTA TTT TAT AGG TAT AAA TGT TAC TTT ACC TCT TGT TTC   1282
Leu Ile Glu Leu Tyr Lys Ile Pro Ile Phe Thr Val Lys Gly Arg Thr Glu
    390                 395                 400                     405

ATC ATC ATC ATC TAT TTT TTC TAA TAT AGC TAT ATT TGC ATT AGT ATT ATA   1333
Asp Asp Asp Asp Ile Lys Glu Leu Ile Ala Ile Asn Ala Asn Thr Asn Tyr
                410                     415                 420

TTT AAT AGG ATT TAT AAA ATA TAC CAT ATT ATC TAT TTT ACT AAA AAA TAA   1384
Lys Ile Pro Asn Ile Phe Tyr Val Met Asn Asp Ile Lys Ser Phe Phe Leu
        425                 430                 435

CAT AGA CAT AAA ATT AAT ACC AGA TTC TGG CAT TTT TAA ATT TTT ATT TGG   1435
Met Ser Met Phe Asn Ile Gly Ser Glu Pro Met Lys Leu Asn Lys Asn Pro
440                 445                     450                 455

                            < G1L                     G2R >
AAA TCT TCT AAT TTT ATT ATT CAT TATTTATTTA ATAA ATG TTT CTA GTT TAT   1488
Phe Arg Arg Ile Lys Asn Asn Met                 Met Phe Leu Val Tyr
            460                                 465
```

Fig. 2E

```
TTC AAT ACA TTT TTA ATA ATA ATT TTA TTA TTT GGT ATT ATA GGT ATT TAT    1539
Phe Asn Thr Phe Leu Ile Ile Ile Leu Leu Phe Gly Ile Ile Gly Ile Tyr
470                 475                 480                 485

ATA TTA ACA TTT GTG TTT AAT ATA GAT TTT TTA ATA AAT AAT AAT AAA ATA    1590
Ile Leu Thr Phe Val Phe Asn Ile Asp Phe Leu Ile Asn Asn Asn Lys Ile
            490                 495                 500

TAT ATA TTA TCA TAT AAC GCA ACT AAT ATA AAC AAT ATA AAT AAT TTA AAT    1641
Tyr Ile Leu Ser Tyr Asn Ala Thr Asn Ile Asn Asn Ile Asn Asn Leu Asn
    505                 510                 515                 520

TTA TAC GAT TAT TCA GAT ATT ATA TTT TTG ACA AAT TTT AAC ATA AAT AAT    1692
Leu Tyr Asp Tyr Ser Asp Ile Ile Phe Leu Thr Asn Phe Asn Ile Asn Asn
                525                 530                 535

AAT CTT TTA GTA ACA CAA GCT AAT AAT TTA CAA GAT ATA CCA ATA TTT AAT    1743
Asn Leu Leu Val Thr Gln Ala Asn Asn Leu Gln Asp Ile Pro Ile Phe Asn
        540                 545                 550

GTA AAT AAT ATT ATA TCT AAT CAA TAT AAT TTT TAT TCA GCG TCT AGT AAT    1794
Val Asn Asn Ile Ile Ser Asn Gln Tyr Asn Phe Tyr Ser Ala Ser Ser Asn
555                 560                 565                 570

AAT GTA AAT ATA TTA TTA GGA TTA AGA AAA ACA TTA AAT ATA AAT AGA AAT    1845
Asn Val Asn Ile Leu Leu Gly Leu Arg Lys Thr Leu Asn Ile Asn Arg Asn
            575                 580                 585
```

Fig. 2F

```
CCA TTT TTA TTA TTT AGA AAT ACA TCT CTA GCT ATA GTT TTC AAT AAT AAT   1896
Pro Phe Leu Leu Phe Arg Asn Thr Ser Leu Ala Ile Val Phe Asn Asn Asn
    590                 595                 600                 605

GAA ACT TTT CAC TGT TAT ATA AGT TCA AAT CAA AAT AGT GAT GTA TTA GAT   1947
Glu Thr Phe His Cys Tyr Ile Ser Ser Asn Gln Asn Ser Asp Val Leu Asp
                610                 615                 620

ATA GTA TCA CAT ATA GAA TTT ATG AAA TCT AGA TAT AAT AAA TAT GTA ATT   1998
Ile Val Ser His Ile Glu Phe Met Lys Ser Arg Tyr Asn Lys Tyr Val Ile
        625                 630                 635

ATA GGA GAA ATA CCC GTA AAT AAT AAT ATA TCT ATT AAT AAT ATA TTA AAT   2049
Ile Gly Glu Ile Pro Val Asn Asn Asn Ile Ser Ile Asn Asn Ile Leu Asn
640                 645                 650                 655

AAT TTT GCT ATT ATA ACT AAT GTG AGA TTA ATA GAT AAA TAT AAC TCT ATA   2100
Asn Phe Ala Ile Ile Thr Asn Val Arg Leu Ile Asp Lys Tyr Asn Ser Ile
            660                 665                 670

ATA TCA TTT TTA AAT ATC AAC GTA GGA ACA CTT TTT GTC ATA AAT CCA TAA   2151
Ile Ser Phe Leu Asn Ile Asn Val Gly Thr Leu Phe Val Ile Asn Pro
    675                 680                 685
TATTTAGTAA TAATCACTAA CATATTTTTT ATTAAAATGA ATAAAATATA TATTGTTATT     2211

GTCAATATTT TATATCATTT TACAGTC TTA TTT TTT TTT TTT GCT TTT AGG TAT     2265
                                  Lys Lys Lys Lys Ser Lys Pro Ile
                                  690                 695

AAT TTT ACC TTC TAA ACG TTT ATC TCC CCA AAC ATC TAC AGT AGA TGG TTT   2316
Ile Lys Gly Glu Leu Arg Lys Asp Gly Trp Val Asp Val Thr Ser Pro Lys
        700                 705                 710

ATT AGA TTC TGT GTT ATA CAC ATC TGC TGG ATT TGC GGC ATT TGT ATC CAA   2367
Asn Ser Glu Thr Asn Tyr Val Asp Ala Pro Asn Ala Ala Asn Thr Asp Leu
715                 720                 725                 730
```

Fig. 2G

```
ACC ATA ATA TCC AGG TCT ATA ATT ATC TTT AAA AAC TTG GGA TTG AGA TAC  2418
Gly Tyr Tyr Gly Pro Arg Tyr Asn Asp Lys Phe Val Gln Ser Gln Ser Val
            735                 740                 745

TTC TTC AGT TTT TAA ATT ATT AAA ATA TCC AAG ATT ATT TTT TTT TGA TGA  2469
Glu Glu Thr Lys Leu Asn Asn Phe Tyr Gly Leu Asn Asn Lys Lys Ser Ser
    750                 755                 760                 765

  < G3L                                      G4R >
AGA CAT AATTGATATT ATAATACTTT ATAGAT ATG TCA ATA TTT ATC TAC TAT     2522
Ser Met                                      Met Ser Ile Phe Ile Tyr Tyr
                                                     770

ATT TTC AAC AAT AGA TTT TAT ATA TAT AAA AGA ATG AAT ACT GTA CAA ATT  2573
Ile Phe Asn Asn Arg Phe Tyr Ile Tyr Lys Arg Met Asn Thr Val Gln Ile
775                 780                 785                 790

TTA GTT GTC ATA TTA ATA ACA ACA GCA TTA TCT TTT CTA GTT TTT CAA TTA  2624
Leu Val Val Ile Leu Ile Thr Thr Ala Leu Ser Phe Leu Val Phe Gln Leu
            795                 800                 805

TGG TAT TAT GCC GAA AAT TAC GAA TAT ATA TTA AGA TAT AAT GAT ACA TAT  2675
Trp Tyr Tyr Ala Glu Asn Tyr Glu Tyr Ile Leu Arg Tyr Asn Asp Thr Tyr
    810                 815                 820                 825

TCA AAT TTA CAA TTT GCG AGA AGC GCA AAT ATA AAT TTT GAT GAT TTA ACT  2726
Ser Asn Leu Gln Phe Ala Arg Ser Ala Asn Ile Asn Phe Asp Asp Leu Thr
                830                 835                 840

GTT TTT GAT CCC AAC GAT AAT GTT TTT AAT GTT GAA GAA AAA TGG CGC TGT  2777
Val Phe Asp Pro Asn Asp Asn Val Phe Asn Val Glu Glu Lys Trp Arg Cys
        845                 850                 855

GCT TCA ACT AAT AAT AAT ATA TTT TAT GCA GTT TCA ACT TTT GGA TTT TTA  2828
Ala Ser Thr Asn Asn Asn Ile Phe Tyr Ala Val Ser Thr Phe Gly Phe Leu
860                 865                 870                 875
```

Fig. 2H

```
AGT ACA GAA AGT ACT GGT ATT AAT TTA ACA TAT ACA AAT TCT AGA GAT TGT   2879
Ser Thr Glu Ser Thr Gly Ile Asn Leu Thr Tyr Thr Asn Ser Arg Asp Cys
            880                 885                 890

ATT ATA GAT TTA TTT TCT AGA ATT ATA AAA ATA GTA TAT GAT CCT TGT ACT   2930
Ile Ile Asp Leu Phe Ser Arg Ile Ile Lys Ile Val Tyr Asp Pro Cys Thr
    895                 900                 905                 910

GTC GAA ACA TCT AAC GAT TGT AGA TTA TTA AGA TTA TTG ATG GCC AAT ACA   2981
Val Glu Thr Ser Asn Asp Cys Arg Leu Leu Arg Leu Leu Met Ala Asn Thr
                915                 920                 925

TCA TAA ATACATTATA ATATTATTAT AATATCAATC ATAATTTTTA TATATATTTT        3037
Ser
                                                   G5R >
ATCTAAAAGG ACTTTTTATT TTTTATATAT TAATAATAAT AA ATG AGT AAC GTA CCT    3094
                                               Met Ser Asn Val Pro
                                                       930
TTA GCA ACC AAA ACA ATA AGA AAA TTA TCA AAT CGA AAA TAT GAA ATA AAG   3145
Leu Ala Thr Lys Thr Ile Arg Lys Leu Ser Asn Arg Lys Tyr Glu Ile Lys
    935                 940                 945                 950

ATT TAT TTA AAA GAT GAA AAT ACT TGT TTC GAA CGT GTA GTA GAT ATG GTA   3196
Ile Tyr Leu Lys Asp Glu Asn Thr Cys Phe Glu Arg Val Val Asp Met Val
                955                 960                 965
GTT CCA TTA TAT GAT GTG TGT AAT GAA ACT TCT GGT GTT ACT TTA GAA TCA   3247
Val Pro Leu Tyr Asp Val Cys Asn Glu Thr Ser Gly Val Thr Leu Glu Ser
        970                 975                 980

TGT AGT CCA AAT ATA GAA GTA ATT GAA TTA GAC AAT ACT CAT GTT AGA ATC   3298
Cys Ser Pro Asn Ile Glu Val Ile Glu Leu Asp Asn Thr His Val Arg Ile
985                 990                 995                 1000

AAA GTT CAC GGC GAT ACA TTA AAA GAA ATG TGT TTT GAA TTA TTG TTC CCG   3349
Lys Val His Gly Asp Thr Leu Lys Glu Met Cys Phe Glu Leu Leu Phe Pro
            1005                1010                1015
```

Fig. 21

```
TGT AAT GTA AAC GAA GCC CAA GTA TGG AAA TAT GTA AGT CGA TTA TTG CTA  3400
Cys Asn Val Asn Glu Ala Gln Val Trp Lys Tyr Val Ser Arg Leu Leu Leu
    1020                1025                1030                1035

GAT AAT GTA TCA CAT AAT GAC GTA AAA TAT AAA TTA GCT AAT TTT AGA CTG  3451
Asp Asn Val Ser His Asn Asp Val Lys Tyr Lys Leu Ala Asn Phe Arg Leu
                1040                1045                1050

ACT CTT AAT GGA AAA CAT TTA AAA TTA AAA GAA ATC GAT CAA CCG CTA TTT  3502
Thr Leu Asn Gly Lys His Leu Lys Leu Lys Glu Ile Asp Gln Pro Leu Phe
        1055                1060                1065

ATT TAT TTT GTC GAT GAT TTG GGA AAT TAT GGA TTA ATT ACT AAG GAA AAT  3553
Ile Tyr Phe Val Asp Asp Leu Gly Asn Tyr Gly Leu Ile Thr Lys Glu Asn
1070                1075                1080                1085

ATT CAA AAT AAT AAT TTA CAA GTT AAC AAA GAT GCA TCA TTT ATT ACT ATA  3604
Ile Gln Asn Asn Asn Leu Gln Val Asn Lys Asp Ala Ser Phe Ile Thr Ile
            1090                1095                1100

TTT CCA CAA TAT GCG TAT ATT TGT TTA GGT AGA AAA GTA TAT TTA AAT GAA  3655
Phe Pro Gln Tyr Ala Tyr Ile Cys Leu Gly Arg Lys Val Tyr Leu Asn Glu
    1105                1110                1115                1120

AAA GTA ACT TTT GAT GTA ACT ACA GAT GCA ACT AAT ATT ACT TTA GAT TTT  3706
Lys Val Thr Phe Asp Val Thr Thr Asp Ala Thr Asn Ile Thr Leu Asp Phe
                1125                1130                1135

AAT AAA TCT GTT AAT ATC GCA GTA TCA TTC CTT GAT ATA TAT TAC GAA GTT  3757
Asn Lys Ser Val Asn Ile Ala Val Ser Phe Leu Asp Ile Tyr Tyr Glu Val
        1140                1145                1150

AAT AAT AAT GAA CAA AAA GAT TTA TTA AAA GAT TTA CTT AAG AGA TAC GGT  3808
Asn Asn Asn Glu Gln Lys Asp Leu Leu Lys Asp Leu Leu Lys Arg Tyr Gly
1155                1160                1165                1170
```

Fig. 2J

```
GAA TTT GAA GTC TAT AAC GCA GAT ACT GGA TTA ATT TAT GCT AAA AAT CTA   3859
Glu Phe Glu Val Tyr Asn Ala Asp Thr Gly Leu Ile Tyr Ala Lys Asn Leu
            1175                1180                1185

AGT ATT AAA AAT TAT GAT ACT GTG ATT CAA GTA GAA AGG TTG CCA GTT AAT   3910
Ser Ile Lys Asn Tyr Asp Thr Val Ile Gln Val Glu Arg Leu Pro Val Asn
    1190                1195                1200                1205

TTG AAA GTT AGA GCA TAT ACT AAG GAT GAA AAT GGT CGC AAT CTA TGT TTG   3961
Leu Lys Val Arg Ala Tyr Thr Lys Asp Glu Asn Gly Arg Asn Leu Cys Leu
                1210                1215                1220

                            RM58
                            __________________________
ATG AAA ATA ACA TCT AGT ACA GAA GTA GAC CCC GAG TAT GTA ACT AGT AAT   4012
Met Lys Ile Thr Ser Ser Thr Glu Val Asp Pro Glu Tyr Val Thr Ser Asn
        1225                1230                1235

AAT GCT TTA TTG GGT ACG CTC AGA GTA TAT AAA AAG TTT GAT AAA TCT CAT   4063
Asn Ala Leu Leu Gly Thr Leu Arg Val Tyr Lys Lys Phe Asp Lys Ser His
1240                1245                1250                1255

TTA AAA ATT GTA ATG CAT AAC AGA GGA AGT GGT AAT GTA TTT CCA TTA AGA   4114
Leu Lys Ile Val Met His Asn Arg Gly Ser Gly Asn Val Phe Pro Leu Arg
            1260                1265                1270

TCA TTA TAT CTG GAA TTG TCT AAT GTA AAA GGA TAT CCA GTT AAA GCA TCT   4165
Ser Leu Tyr Leu Glu Leu Ser Asn Val Lys Gly Tyr Pro Val Lys Ala Ser
    1275                1280                1285                1290

GAT ACT TCG AGA TTA GAT GTT GGT ATT TAC AAA TTA AAT AAA ATT TAT GTA   4216
Asp Thr Ser Arg Leu Asp Val Gly Ile Tyr Lys Leu Asn Lys Ile Tyr Val
                1295                1300                1305

GAT AAC GAC GAA AAT AAA ATT ATA TTG GAA GAA ATT GAA GCA GAA TAT AGA   4267
Asp Asn Asp Glu Asn Lys Ile Ile Leu Glu Glu Ile Glu Ala Glu Tyr Arg
        1310                1315                1320
```

Fig. 2K

```
TGC GGA AGA CAA GTA TTC CAC GAA CGT GTA AAA CTT AAT AAA CAC CAA TGT   4318
Cys Gly Arg Gln Val Phe His Glu Arg Val Lys Leu Asn Lys His Gln Cys
1325                1330                1335                1340

AAA TAT ACT CCC AAA TGT CCA TTC CAA TTT GTT GTA AAC AGC CCA GAT ACT   4369
Lys Tyr Thr Pro Lys Cys Pro Phe Gln Phe Val Val Asn Ser Pro Asp Thr
            1345                1350                1355

ACG ATT CAC TTA TAT GGT ATT TCT AAT GTT TGT TTA AAA CCT AAA GTA CCC   4420
Thr Ile His Leu Tyr Gly Ile Ser Asn Val Cys Leu Lys Pro Lys Val Pro
    1360                1365                1370                1375

AAA AAT TTA AGA CTT TGG GGA TGG ATT TTA GAT TGC GAT ACT TCT AGA TTT   4471
Lys Asn Leu Arg Leu Trp Gly Trp Ile Leu Asp Cys Asp Thr Ser Arg Phe
                1380                1385                1390

ATT AAA CAT ATG GCT GAT GGA TCT GAT GAT TTA GAT CTT GAC GTT AGG CTT   4522
Ile Lys His Met Ala Asp Gly Ser Asp Asp Leu Asp Leu Asp Val Arg Leu
        1395                1400                1405

AAT AGA AAT GAT ATA TGT TTA AAA CAA GCC ATA AAA CAA CAT TAT ACT AAT   4573
Asn Arg Asn Asp Ile Cys Leu Lys Gln Ala Ile Lys Gln His Tyr Thr Asn
1410                1415                1420                1425

GTA ATT ATA TTA GAG TAC GCA AAT ACA TAT CCA AAT TGC ACA TTA TCA TTG   4624
Val Ile Ile Leu Glu Tyr Ala Asn Thr Tyr Pro Asn Cys Thr Leu Ser Leu
            1430                1435                1440

GGT AAT AAT AGA TTT AAT AAT GTA TTT GAT ATG AAT GAT AAC AAA ACT ATA   4675
Gly Asn Asn Arg Phe Asn Asn Val Phe Asp Met Asn Asp Asn Lys Thr Ile
    1445                1450                1455                1460

TCT GAG TAT ACT AAC TTT ACA AAA AGT AGA CAA GAC CTT AAT AAC ATG TCA   4726
Ser Glu Tyr Thr Asn Phe Thr Lys Ser Arg Gln Asp Leu Asn Asn Met Ser
                1465                1470                1475
```

Fig. 2L

```
TGT ATA TTA GGA ATA AAC ATA GGT AAT TCC GTA AAT ATT AGT AGT TTG CCT  4777
Cys Ile Leu Gly Ile Asn Ile Gly Asn Ser Val Asn Ile Ser Ser Leu Pro
        1480                1485                1490

GGT TGG GTA ACA CCT CAC GAA GCT AAA ATT CTA AGA TCT GGT TGT GCT AGA  4828
Gly Trp Val Thr Pro His Glu Ala Lys Ile Leu Arg Ser Gly Cys Ala Arg
1495                1500                1505                1510

GTT AGA GAA TTT TGT AAA TCA TTC TGT GAT CTT TCT AAT AAG AGA TTC TAT  4879
Val Arg Glu Phe Cys Lys Ser Phe Cys Asp Leu Ser Asn Lys Arg Phe Tyr
            1515                1520                1525

GCT ATG GCT AGA GAT CTC GTA AGT TTA CTA TTT ATG TGT AAC TAT GTT AAT  4930
Ala Met Ala Arg Asp Leu Val Ser Leu Leu Phe Met Cys Asn Tyr Val Asn
    1530                1535                1540                1545

ATT GAA ATT AAC GAA GCA GTA TGC GAA TAT CCT GGA TAT GTC ATA TTA TTC  4981
Ile Glu Ile Asn Glu Ala Val Cys Glu Tyr Pro Gly Tyr Val Ile Leu Phe
                1550                1555                1560

GCA AGA GCT ATT AAA GTA ATT AAT GAT TTA TTA TTA ATT AAC GGA GTA GAT  5032
Ala Arg Ala Ile Lys Val Ile Asn Asp Leu Leu Leu Ile Asn Gly Val Asp
        1565                1570                1575

AAT CTA GCA GGA TAT TCA ATT TCC TTA CCT ATA CAT TAT GGA TCT ACT GAA  5083
Asn Leu Ala Gly Tyr Ser Ile Ser Leu Pro Ile His Tyr Gly Ser Thr Glu
1580                1585                1590                1595

AAG ACT CTA CCA AAT GAA AAG TAT GGT GGT GTT GAT AAG AAA TTT AAA TAT  5134
Lys Thr Leu Pro Asn Glu Lys Tyr Gly Gly Val Asp Lys Lys Phe Lys Tyr
            1600                1605                1610

CTA TTC TTA AAG AAT AAA CTA AAA GAT TTA ATG CGT GAT GCT GAT TTT GTC  5185
Leu Phe Leu Lys Asn Lys Leu Lys Asp Leu Met Arg Asp Ala Asp Phe Val
    1615                1620                1625                1630
```

Fig. 2M

```
CAA CCT CCA TTA TAT ATT TCT ACT TAC TTT AGA ACT TTA TTG GAT GCT CCA   5236
Gln Pro Pro Leu Tyr Ile Ser Thr Tyr Phe Arg Thr Leu Leu Asp Ala Pro
                1635                1640                1645

CCA ACT GAT AAT TAT GAA AAA TAT TTG GTT GAT TCG TCC GTA CAA TCA CAA   5287
Pro Thr Asp Asn Tyr Glu Lys Tyr Leu Val Asp Ser Ser Val Gln Ser Gln
        1650                1655                1660

GAT GTT CTA CAG GGT CTG TTG AAT ACA TGT AAT ACT ATT GAT ACT AAT GCT   5338
Asp Val Leu Gln Gly Leu Leu Asn Thr Cys Asn Thr Ile Asp Thr Asn Ala
1665                1670                1675                1680

AGA GTT GCA TCA AGT GTT ATT GGA TAT GTT TAT GAA CCA TGC GGA ACA TCA   5389
Arg Val Ala Ser Ser Val Ile Gly Tyr Val Tyr Glu Pro Cys Gly Thr Ser
            1685                1690                1695

GAA CAT AAA ATT GGT TCA GAA GCA TTG TGT AAA ATG GCT AAA GAA GCA TCT   5440
Glu His Lys Ile Gly Ser Glu Ala Leu Cys Lys Met Ala Lys Glu Ala Ser
    1700                1705                1710                1715

AGA TTA GGA AAT CTA GGT TTA GTA AAT CGT ATT AAT GAA AGT AAT TAC AAC   5491
Arg Leu Gly Asn Leu Gly Leu Val Asn Arg Ile Asn Glu Ser Asn Tyr Asn
                1720                1725                1730

AAA TGT AAT AAA TAT GGT TAT AGA GGA GTA TAC GAA AAT AAC AAA CTA AAA   5542
Lys Cys Asn Lys Tyr Gly Tyr Arg Gly Val Tyr Glu Asn Asn Lys Leu Lys
        1735                1740                1745

ACA AAA TAT TAT AGA GAA ATA TTT GAT TGT AAT CCT AAT AAT AAT AAT GAA   5593
Thr Lys Tyr Tyr Arg Glu Ile Phe Asp Cys Asn Pro Asn Asn Asn Asn Glu
1750                1755                1760                1765

TTA ATA TCC AGA TAT GGA TAT AGA ATA ATG GAT TTA CAT AAA ATT GGA GAA   5644
Leu Ile Ser Arg Tyr Gly Tyr Arg Ile Met Asp Leu His Lys Ile Gly Glu
            1770                1775                1780
```

Fig. 2N

ATT TTT GCA AAT TAC GAT GAA AGT GAA TCT CCT TGC GAA CGA AGA TGT CAT 5695
Ile Phe Ala Asn Tyr Asp Glu Ser Glu Ser Pro Cys Glu Arg Arg Cys His
1785 1790 1795 1800

TAC TTG GAA GAT AGA GGT CTT TTA TAT GGT CCT GAA TAT GTA CAT CAC AGA 5746
Tyr Leu Glu Asp Arg Gly Leu Leu Tyr Gly Pro Glu Tyr Val His His Arg
1805 1810 1815

TAT CAA GAA TCA TGT ACG CCT AAT ACG TTT GGA AAT AAC ACA AAT TGT GTA 5797
Tyr Gln Glu Ser Cys Thr Pro Asn Thr Phe Gly Asn Asn Thr Asn Cys Val
1820 1825 1830

ACA AGA AAT GGT GAA CAA CAC GTA TAC GAA AAT AGT TGT GGA GAT AAT GCA 5848
Thr Arg Asn Gly Glu Gln His Val Tyr Glu Asn Ser Cys Gly Asp Asn Ala
1835 1840 1845 1850

ACA TGT GGA AGA AGA ACA GGA TAT GGA AGA AGA AGT AGG GAT GAA TGG AAT 5899
Thr Cys Gly Arg Arg Thr Gly Tyr Gly Arg Arg Ser Arg Asp Glu Trp Asn
1855 1860 1865

GAC TAT AGA AAA CCC CAC GTT TAT GAC AAT TGT GCC GAT GCA AAT AGT TCA 5950
Asp Tyr Arg Lys Pro His Val Tyr Asp Asn Cys Ala Asp Ala Asn Ser Ser
1870 1875 1880 1885

TCT TCA GAT AGC TGT TCA GAC AGT AGT AGT AGT AGT GAA TCT GAA TCT GAT 6001
Ser Ser Asp Ser Cys Ser Asp Ser Ser Ser Ser Ser Glu Ser Glu Ser Asp
1890 1895 1900

TCA GAT GGA TGT TGC GAC ACA GAT GCT AGT TTA GAT TCT GAT ATT GAA AAT 6052
Ser Asp Gly Cys Cys Asp Thr Asp Ala Ser Leu Asp Ser Asp Ile Glu Asn
1905 1910 1915

TGT TAT CAA AAT CCA TCA AAA TGT GAT GCA GGA TGC TAA ATGAAATTTA 6101
Cys Tyr Gln Asn Pro Ser Lys Cys Asp Ala Gly Cys
1920 1925 1930

Fig. 2O

```
ATATTATATA ATATTAACTT ACAAGTTATA AAAATCATTA AAATGATTTT TTAAAATGAT    6161

ATTATCGATA GTTGTGATAA TGTGCTCTTT TATTTTATTA ATTGCGATGA TTATAATATT    6221

ATCTTTTAGA TATATTTAAT ATTAATTATA AATCGACTGA CAATAATATT TATTC CTA     6279

TTC ATA ATA ATC ATC TGC TAT ATA TAT TAA TGT ATC ATT CTC TAT TAT AAA  6330
Glu Tyr Tyr Asp Asp Ala Ile Tyr Ile Leu Thr Asp Asn Glu Ile Ile Phe
            1935                1940                1945

TAT AGG TAT ATT GTC TTT ATC AAT CAT TAA TTT TGC TAC AGC TGT ATT ATC  6381
Ile Pro Ile Asn Asp Lys Asp Ile Met Leu Lys Ala Val Ala Thr Asn Asp
    1950                1955                1960                1965

TTT ATA TAC TAT ATT TGT GTC TTT GTT TAA TAA ACC TTT TAA TAT AGT GGC  6432
Lys Tyr Val Ile Asn Thr Asp Lys Asn Leu Leu Gly Lys Leu Ile Thr Ala
                1970                1975                1980

TCT ATC ATA ATC TTT ACA ATA TGA TAT GGG ATA TAA TTT TAT ATT AAT AAT  6483
Arg Asp Tyr Asp Lys Cys Tyr Ser Ile Pro Tyr Leu Lys Ile Asn Ile Ile
        1985                1990                1995

AAC ATT AGA TAC GTT CAT TTC TTT CAT TCT AGT TTT ACG TAT TGT GTC AAA  6534
Val Asn Ser Val Asn Met Glu Lys Met Arg Thr Lys Arg Ile Thr Asp Phe
2000                2005                2010                2015

AAT TAT TTC ATT TTC TGC TGG TTC TAT ATA TTT ATA TGT GTT ATG AAT AGA  6585
Ile Ile Glu Asn Glu Ala Pro Glu Ile Tyr Lys Tyr Thr Asn His Ile Ser
            2020                2025                2030

TTC GAT AGA TGA TGA TTT TAA TAA ATC AAA TAT AAC ATT TAT TTT ACC TTG  6636
Glu Ile Ser Ser Ser Lys Leu Leu Asp Phe Ile Val Asn Ile Lys Gly Gln
    2035                2040                2045                2050
```

Fig. 2P

```
TTT ATC TTT TAT AAT ATC TAA TAT TTC TTT ATC TAC AGA TTT TCT GTT GTT    6687
Lys Asp Lys Ile Ile Asp Leu Ile Glu Lys Asp Val Ser Lys Arg Asn Asn
                2055                2060                2065

GGT ATA TGA TAT TAA AAA ATG AAC GTT AAC ATA TCT ATA TTC TTG TGG TAA    6738
Thr Tyr Ser Ile Leu Phe His Val Asn Val Tyr Arg Tyr Glu Gln Pro Leu
        2070                2075                2080

                                  < G6L
ATC TTT ATG AGA ATT TAA TCT TAT AGA TCT                                6768
Asp Lys His Ser Asn Leu Arg Ile Ser Arg
2085                2090            2094
```

Fig. 3A

```
GAATTCAAGT TAAATAT TTA TAA ACA ACA ATC ATA TTT TTT TAA AGA ATC TAA        53
                       Leu Cys Cys Asp Tyr Lys Lys Leu Ser Asp Leu
                        1               5                  10

TAA ATT TTT TAA CAT TTT ATT ATT ATT TGA TAA TTG TTT ATT TAA TTC GTT      104
Leu Asn Lys Leu Met Lys Asn Asn Asn Ser Leu Gln Lys Asn Leu Glu Asn
             15                  20                  25

ATT GAT ATT AAC AAT ATT ATT TAT CAT TTT ACC TAT TTT TTT TTT TCT ATC      155
Asn Ile Asn Val Ile Asn Asn Ile Met Lys Gly Ile Lys Lys Lys Arg Asp
     30                  35                  40                  45

                         RM129
            ______________________________
TAC TAA CGA AAT ATC AGA TTT TGC ACC TTC AAT ATC AGA ATA ATA ATT ATC      206
Val Leu Ser Ile Asp Ser Lys Ala Gly Glu Ile Asp Ser Tyr Tyr Asn Asp
                 50                  55                  60

      < ORF Q1
ATT ATT TTG CAT TTATGAATAA AAATA TTA ATA TGA ATT ATT ATA ACA TAA         257
Asn Asn Gln Met                          Tyr Ser Asn Asn Tyr Cys Leu
         65                                          70

TCT ACA CAC AGG AAC ATA TAA ATC TTG TCC ACC TAT TTC AAT TAT TTG ATT      308
Arg Cys Val Pro Val Tyr Leu Asp Gln Gly Gly Ile Glu Ile Ile Gln Asn
     75                  80                  85                  90

TTT ATT ATG TTT TTT AAT TGT AAA AGA AGC ATC TTT ATA ACA AAA TTG ACA      359
Lys Asn His Lys Lys Ile Thr Phe Ser Ala Asp Lys Tyr Cys Phe Gln Cys
                 95                 100                 105

TAT AGC TTG TAA TTT TTT TAT TTT TTC TAC TTT AGG AAT TAA TTT TGA TAT      410
Ile Ala Gln Leu Lys Lys Ile Lys Glu Val Lys Pro Ile Leu Lys Ser Ile
        110                 115                 120
```

Fig. 3B

```
                                                      RM03
AGA ATT AAA TAT ATT TCT GTT AAA GTC ACA ATT TAA TCC AGC AAC AAT AAC     461
Ser Asn Phe Ile Asn Arg Asn Phe Asp Cys Asn Leu Gly Ala Val Ile Val
125                 130                 135                 140

TTT TTT TTT ATT ATT AGC CAT TTT ATC ACA AAA TTG TTC TAA ATC ATT TTC     512
Lys Lys Lys Asn Asn Ala Met Lys Asp Cys Phe Gln Glu Leu Asp Asn Glu
            145                 150                 155

TTC AAA AAA TTG ACA CTC ATC TAT GCC AAT AAT ATC ATA ATT ATC TAC GAT     563
Glu Phe Phe Gln Cys Glu Asp Ile Gly Ile Ile Asp Tyr Asn Asp Val Ile
    160                 165                 170                 175

ATT GAT TTC ATT AAT TAA ATT ATT TGT TTT AAT GTA TAA ATA TTC TTT ATT     614
Asn Ile Glu Asn Ile Leu Asn Asn Thr Lys Ile Tyr Leu Tyr Glu Lys Asn
                180                 185                 190

TAA TAT ATT TCC GTC ATG ATT TAT TAT ATT TTT ATT TAT AAA TCT ATT ATC     665
Leu Ile Asn Gly Asp His Asn Ile Ile Asn Lys Asn Ile Phe Arg Asn Asp
        195                 200                 205

TAT ATT ATG AGT TAT AAT TAC ACA TTT TTG ATT AGA TAA AAT ATA TCT ATT     716
Ile Asn His Thr Ile Ile Val Cys Lys Gln Asn Ser Leu Ile Tyr Arg Asn
210                 215                 220                 225
                                                       RM04
AAT TTT TCG CAT CAA TTC TGT TGT TTT GCC AGA AAA CAT AGG ACC AAT TAT     767
Ile Lys Arg Met Leu Glu Thr Thr Lys Gly Ser Phe Met Pro Gly Ile Ile
            230                 235                 240
        < ORF Q2
TAA TTC TAT CGA CAT TTTTTTTTAT TATTTGATAT ATTTTTTCAA AAAAAAATTA         822
Leu Glu Ile Ser Met
    245
                                    ORF Q3 >
ATCAATGAAA AAAAAATAAA ATTATCAAA ATG GAT TTA CTA AAT TCT GAT ATA ATT     878
                                Met Asp Leu Leu Asn Ser Asp Ile Ile
                                    250                 255
```

Fig. 3C

```
TTA ATA AAT ATT TTA AAA TAT TAT AAT TTA AAA AAA ATA ATA ATA AAC AGA    929
Leu Ile Asn Ile Leu Lys Tyr Tyr Asn Leu Lys Lys Ile Ile Ile Asn Arg
        260                 265                 270

GAT AAT GTT ATT AAT ATT AAT ATA TTA AAA AAA TTA GTT AAT TTA GAA GAA    980
Asp Asn Val Ile Asn Ile Asn Ile Leu Lys Lys Leu Val Asn Leu Glu Glu
275                 280                 285                 290

TTG CAT ATA ATA TAT TAT GAT AAT AAT ATT TTA AAT AAT ATT CCA GAA AAT   1031
Leu His Ile Ile Tyr Tyr Asp Asn Asn Ile Leu Asn Asn Ile Pro Glu Asn
            295                 300                 305

ATT AAA AGT TTA TAT ATT TCA AAT TTA AAT ATT ATT AAT TTA AAT TTT ATA   1082
Ile Lys Ser Leu Tyr Ile Ser Asn Leu Asn Ile Ile Asn Leu Asn Phe Ile
    310                 315                 320                 325

ACA AAA TTA AAA AAT ATA ACA TAT TTA GAT ATA TCT TAT AAC AAA AAT AGC   1133
Thr Lys Leu Lys Asn Ile Thr Tyr Leu Asp Ile Ser Tyr Asn Lys Asn Ser
                330                 335                 340

AAT ATA AGT AAT ATT ATA CTA CCA CAT TCT ATA GAA TTT TTA AAT TGT GAA   1184
Asn Ile Ser Asn Ile Ile Leu Pro His Ser Ile Glu Phe Leu Asn Cys Glu
        345                 350                 355

TCA TGT AAT ATA AAT GAC TAT AAT TTT ATT AAT AAT TTA GTA AAT TTA AAA   1235
Ser Cys Asn Ile Asn Asp Tyr Asn Phe Ile Asn Asn Leu Val Asn Leu Lys
360                 365                 370                 375

AAA TTA ATA ATA TCT AAA AAT AAA TTT GGT AAC TTT AAT AAT GTT TTT CCT   1286
Lys Leu Ile Ile Ser Lys Asn Lys Phe Gly Asn Phe Asn Asn Val Phe Pro
            380                 385                 390

ATT AGT ATA GTT GAG TTA AAT ATG GAA TCA ATA CAA ATA AAA GAT TAT AAA   1337
Ile Ser Ile Val Glu Leu Asn Met Glu Ser Ile Gln Ile Lys Asp Tyr Lys
    395                 400                 405                 410
```

Fig. 3D

```
TTT ATA GAA AAA TTA ATT AAT TTA AAA AAA TTA GAT ATA TCT TTC AAT GTT     1388
Phe Ile Glu Lys Leu Ile Asn Leu Lys Lys Leu Asp Ile Ser Phe Asn Val
                415                     420                 425

AAA AAA AAT AAT ATA CAT TTG ATA AAA TTT CCA AAA AGT ATA ACT CAT TTA     1439
Lys Lys Asn Asn Ile His Leu Ile Lys Phe Pro Lys Ser Ile Thr His Leu
        430                 435                 440

TGT GAT TAT CAA TCA TAT AAA GAA AAT TAT AAT TAT TTA AAA AAT TTA TCA     1490
Cys Asp Tyr Gln Ser Tyr Lys Glu Asn Tyr Asn Tyr Leu Lys Asn Leu Ser
445                 450                     455                 460

AAT ATA ATT GAA TAT GAA TTC                                             1511
Asn Ile Ile Glu Tyr Glu Phe
            465
```

AmEPV Hind III map:

| C | I | B | A | F | J | G | D | H | E | scale: 10 kb scale: 0.5 kb

Positions: 0 — G1L 1.4 kb — 931 (H) — G2R 0.7 kb — 4.51 kb — G3L 0.2 kb — G4R 0.5 kb — 4504 (B) — 307 bp — 4811 (B) — 80 bp — 4891 (B) — G5R 3.0 kb — 1.88 kb — 6768 (B) — G6L Amino Acid Homologies:
- G1L — Vaccinia ORF I7
- G4R — Capripoxvirus HM3
- G5R — Spheroidin
- G6L — Vaccinia NTPase I

Fig. 6A

```
      4044         .         .         .         .         .
AmEPV     AAAAGTTTGATAAATCTCATTTAAAAATTGTAATGCATAACAGAGGAAGT
          |||||||||||||||| |||||||||||||| |||||||| |||||||||
CbEPV   1 AAAAGTTTGATAAATCACATTTAAAAATTGTTATGCATAATAGAGGAAGT
          |||||||||||||||||||||||||||| |||||||| |||||||||||
CfEPV   1 AAAAGTTTGATAAATCACATTTAAAAATCGTTATGCACAATAGAGGAAGC

      4094         .         .         .         .         .
AmEPV     GGTAATGTATTTCCATTAAGATCATTATATCTGGAATTGTCTAATGTAAA
          ||||||||||| ||  | |||||| ||||| ||||||| |  || || ||
CbEPV  51 GGTAATGTATTCCCTATTAGATCACTATATTTGGAATTATTGAACGTCAA
          ||||||||||||||||||||||||||||||||||||||||||||||||||
CfEPV  51 GGTAATGTATTCCCTATTAGATCACTATATTTGGAATTATTGAACGTCAA

      4144         .         .         .         .         .
AmEPV     AGGATATCCAGTTAAAGCATCTGATACTTCGAGATTAGATGTTGGTATTT
          ||| ||||| || |||||||| ||||| || || |||||||||||| |||
CbEPV 101 AGGTTATCCTGTAAAAGCATCCGATACGTCTAGGTTAGATGTTGGTGTTT
          |||||||||||| |||||||||||||||||||||||||| ||||||||||
CfEPV 101 AGGTTATCCTGTTAAAGCATCCGATACGTCTAGGTTAGACGTTGGTGT

      4194         .         .         .         .         .
AmEPV     ACAAATTAAATAAAATTTATGTAGATAACGACGAAAATAAAATTATATTG
          | ||| |||||||||| ||| | ||||| || ||||||||||| || ||
CbEPV 151 ATAAACTAAATAAAATATATATTGATAATGATGAAAATAAAATAATTTTA
          ||||||||||||||||||||||||||||||||||||||||||||||||||
CfEPV 151 ATAAACTAAATAAAATATATATTGATAATGATGAAAATAAAATAATTTTA

      4244         .         .         . 4278
AmEPV     GAAGAAATTGAAGCAGAATATAGATGCGGAAGACA
          |||||||||||| | || |||||||| |||||| |
CbEPV 201 GAAGAAATTGAAACCGATTATAGATGTGGAAGAGA 235
          |||||||| ||||||||||||||||||||||||||
CfEPV 201 GAAGAAATCGAAACCGATTATAGATGTGGAAGAGA 235
```

Fig. 6B

```
          323       .         .         .         .         .
AmEPV       KFDKSHLKIVMHNRGSGNVFPLRSLYLELSNVKGYPVKASDTSRLDVGIY
            |||||||||||||||||||||:||||||| ||||||||||||||||||:|
CbEPV     1 KFDKSHLKIVMHNRGSGNVFPIRSLYLELLNVKGYPVKASDTSRLDVGVY
            ||||||||||||||||||||||||||||||||||||||||||||||||||
CfEPV     1 KFDKSHLKIVMHNRGSGNVFPIRSLYLELLNVKGYPVKASDTSRLDVGVY

          373       .         .         399
AmEPV       KLNKIYVDNDENKIILEEIEAEYRCGR
            ||||||:|||||||||||||.:|||||
CbEPV       KLNKIYIDNDENKIILEEIETDYRCGR  77
            |||||||||||||||||||||||||||
CfEPV       KLNKIYIDNDENKIILEEIETDYRCGR  77
```

Fig. 6C

```
          211        221
AmEPV       KFKYLFLKNK
            ||||||||||
CbEPV     1 KFKYLFLKNK  10

          682         691
AmEPV       KSVNIAVSFLD
            |||||||||||
CbEPV     1 KSVNIAVSFLD  11

          726         736
AmEPV       KYLVDSSVQSQ
            |||||||||||
CbEPV     1 KYLVDSSVQSQ  11
```

Fig. 7A

G I I Q K L E S E N W P M D L I
6769 TCCTATTATTTGTTTTAATTCTGATTCATTCCACGGCATATCTAATATAA

I I D N I C K F S I G E S G A Y S
6819 TTATATCATTAATACATTTGAATGATATGCCTTCAGATCCAGCGTAAGAA

F I C V K V K K G N N N E Y N N Y
6869 AATATGCAAACTTTTACTTTTTTACCATTATTATTTTCATAATTATTATA

E N L E N D R T K L T K S S Y E
6919 TTCGTTTAATTCATTATCTCTAGTTTTTAAAGTTTTGCTAGAATATTCAA

I Y S I N F C N F Y C K L S S I G
6969 TATAAGAAATATTAAAACAATTAAAATAACATTTTAAACTTGATATTCCT

E F N V L P E F I L V K G R S N L
7019 TCAAAATTAACTAAAGGTTCAAATATTAATACTTTTCCTCTCGAATTTAA

I I K C T E I Y K C S Y Q Y L I
7069 AATTATTTTACAAGTTTCTATATATTTACACGAATATTGATATAATATAT

N Y N N I D T I P L N T K I K I N
7119 TATAATTATTTATATCAGTGATTGGTAAATTAGTTTTTATTTTTATATTA

D N K F S E I F S E S F N I N K T
7169 TCATTTTTAAAACTTTCAATAAAAGATTCAGAGAAATTAATATTTTTTGT

F E S F E A L K R K I M D N Y E
7219 AAACTCGGAAAATTCAGCAAGTTTTCTTTTAATCATATCATTATATTCTA

I N D L D G K I K L D Y F A F S S
7269 TATTATCTAAATCTCCTTTTATTTTAAGATCATAAAAAGCAAATGAAGAT

I L R R M T K L G G L E T K Y D Y
7319 ATTAATCTTCTCATAGTTTTTAAACCACCTAATTCAGTTTTATAATCATA

K E A M N Y L K S Q E D S M I I
7369 TTTTTCTGCCATATTATATAATTTAGATTGCTCATCTGACATAATTATAT

N H Y F I N K K A Y G D I Y N T E
7419 TATGATAAAATATATTTTTTTTGCATATCCATCTATATAATTTGTTTCT

T L S D A E I L R K Y S C I A L L
7469 GTTAAACTATCTGCTTCTATTAATCTTTTATAAGAACATATAGCTAATAA

T E R L E K F N I L K G N N I Y
7519 TGTTTCTCTTAATTCCTTAAAATTAATTAACTTTCCATTATTTATATATT

E E K I N M V N P R L L G I L N N
7569 CTTCTTTTATATTCATAACATTTGGTCTAAGTAAACCTATTAAATTATTA

Fig. 7B

```
      F  E  S  I  N  N  T  V  P  T  A  S  M  C  L  I  K
7619  AATTCAGAAATATTATTAGTTACTGGAGTAGCGGACATACATAATATTTT

       N  N  E  F  N  A  L  K  I  L  K  K  Y  I  P  T
7669  ATTATTTTCGAAATTTGCTAATTTTATTAATTTTTTATAAATAGGAGTAA

      F  N  R  E  N  N  D  K  K  V  T  R  S  I  L  K  H
7719  AATTTCTTTCGTTATTATCTTTTTTAACAGTTCTTGATATTAATTTATGA

      V  E  D  I  I  I  L  L  R  S  K  K  N  L  S  S  E
7769  ACTTCGTCTATTATTATTAGTAATCTACTTTTTTTATTAAGAGAACTTTC

       I  S  R  Y  I  N  N  F  K  D  L  S  S  S  S  D
7819  TATAGATCTATATATATTATTAAATTTATCTAAACTAGATGACGAATCAT

      Y  Y  I  F  K  I  N  S  T  D  S  I  Y  S  R  I  T
7869  AATATATAAATTTTATATTACTGGTATCTGATATATATGATCTTATAGTA

      N  L  W  P  D  I  Y  L  S  K  K  I  F  I  L  I  I
7919  TTTAACCAAGGATCTATGTATAATGATTTTTTAATAAATATTAAAATTAT

       W  R  P  F  L  E  K  I  Y  K  I  I  Y  V  A  T
7969  CCATCTTGGAAATAATTCTTTTATATATTTTATAATATACACAGCAGTTA

      L  T  K  G  M  G  T  D  W  F  L  L  M  S  N  L  N
8019  ATGTTTTTCCCATACCAGTATCCCAAAATAATAACATACTATTCAAATTT

       K  L  G  I  F  I  R  S  V  F  Y  Q  Y  D  Q  L  T
8069  TTTAATCCTATGAATATTCTACTTACAAAATATTGATAATCTTGTAATGT

       I  E  T  N  T  I  N  N  M  I  K  N  P  L  H  Q
8119  AATTTCAGTATTTGTAATATTATTCATAATTTTATTAGGCAAATGTTGTG

      T  K  D  L  A  Y  N  I  H  K  G  V  I  S  D  L  A
8169  TTTTATCAAGTGCATAATTTATATGTTTACCAACAATAGAATCTAATGCA

      < AmEPV NPH I
       F  M
8219  AACATTTAGTTATATAAAAAAATAATATTTATATTAACTTAAGATGTTTCA

8269  TTAATTTTATGTCTGTGATGTGGAGTTAAAACCCAAGATATTGATATATC

8319  TATATCATTAATTCTTCTTTTGAATCTATGTCTATCAATCGCAAATTTAT

8369  CCCAGTATAATTTTCGAGTTTGTTTTGCAGCATATAACCAAACATACATA

8419  ATGTGGAGTTTTGGTGGTTCGGATGAAAAGCGTACTTTT        8457
```

ENTOMOPOXVIRUS EXPRESSION SYSTEM

CROSS-REFERENCE TO A RELATED APPLICATION

This application is a continuation of application Ser. No. 08/544,332, filed Oct. 17, 1995, now U.S. Pat. No. 5,935,777; which is a continuation-in-part of application Ser. No. 08/107,755, filed on Nov. 22, 1993 now U.S. Pat. No. 5,721,352; and is also a continuation-in-part of U.S. application Ser. No. 07/991,867, filed Dec. 7, 1992, now U.S. Pat. No. 5,476,781; which was a continuation-in-part of International Application No. PCT/US92/00855, filed Feb. 12, 1992, now U.S. Pat. No. 5,721,352; which is a continuation-in-part of U.S. application Ser. No. 07/827,685, filed Jan. 30, 1992, now abandoned; which is a continuation-in-part of U.S. application Ser. No. 07/657,584, filed Feb. 19, 1991, now abandoned.

This invention was made with Government support under Grant No. R01 AI15722-12 awarded by the National Institutes of Health and NIH Training Grant T32 AI-07110. The Government has certain rights in this invention.

FIELD OF THE INVENTION

This invention relates generally to the field of recombinantly-produced proteins and specifically to novel, recombinant Entomopoxvirus genes, proteins, protein regulatory sequences and their uses in expressing heterologous genes in transformed hosts.

BACKGROUND OF THE INVENTION

Poxviruses are taxonomically classified into the family Chordopoxvirinae, whose members infect vertebrate hosts, e.g., the Orthopoxvirus vaccinia, or into the family Entomopoxvirinae. Very little is known about members of the Entomopoxvirinae family other than the insect host range of individual members. One species of Entomopoxvirus (EPV) is the *Amsacta moorei* Entomopoxvirus (AmEPV), which was first isolated from larvae of the red hairy caterpillar *Amsacta moorei* (Roberts and Granados [1968] *J. Invertebr. Pathol.* 12:141–143). AmEPV is the type species of genus B of EPVs and is one of three known EPVs which will replicate in cultured insect cells (R. R. Granados et al. [1976] "Replication of *Amsacta moorei* Entomopoxvirus and *Autographa californica* Nuclear Polyhedrosis Virus in Hemocyte Cell Lines from *Estigmene acrea*," in *Invertebrate Tissue Culture Applications in Medicine, Biology, and Agriculture*, E. Kurstak and K. Maramorosch (ed.), Academic Press, New York, pp. 379–389; T. Hukuhara et al. [1990] *J. Invertebr. Pathol.* 56:222–232; and Sato, T. [1989] "Establishment of Eight Cell Lines from Neonate Larvae of Torticids (Lepidoptera), and Their Several Characteristics Including Susceptibility to Insect Viruses," in *Invertebrate Cell Systems Applications*, J. Mitsuhashi (ed.), Vol. II, CRC Press, Inc., Boca Raton, Fla., pp. 187–198).

AmEPV is one of the few insect poxviruses which can replicate in insect cell culture; AmEPV is unable to replicate in vertebrate cell lines. The AmEPV double-stranded DNA genome is about 225 kb and is unusually A+T rich (18.5% G+C) (W. Langridge, H. R., et al. [1977] *Virology* 76:616–620). Recently, a series of restriction maps for AmEPV were published (Hall, R. L., et al. [1990] *Arch. Virol.* 110:77–90). No DNA homology to vaccinia has been detected (Langridge, W. H. [1983] *J. Invertebr. Pathol.* 42:77–82; Langridge, W. H. [1984] *J. Invertebr. Pathol.* 43:41–46).

The viral replication cycle of AmEPV resembles that of other poxviruses except for the appearance of occluded virus late in infection. For AmEPV, once a cell is infected, both occluded and extracellular virus particles are generated. The mature occlusion body particle, which is responsible for environmentally protecting the virion during infection, consists of virus embedded within a crystalline matrix consisting primarily of a single protein, spheroidin. Spheroidin, the major structural protein of AmEPV, has been reported to be 110 kDa in molecular weight and to consist of a high percentage of charged and sulfur-containing amino acids (Langridge and Roberts [1982] *J. Invertebr. Pathol.* 39:346–353).

Another insect virus is the baculovirus. Like baculoviruses, a characteristic feature of entomopoxviruses is the amalgamation of virions within environmentally stable occlusion bodies. It is this occluded form of the virus that is primarily responsible for dissemination to other insects. While the major protein (polyhedrin) of baculovirus occlusions is quite similar between viruses, it has been reported that the major occlusion body protein (spheroidin) of two group B entomopoxviruses, *Amsacta moorei* (AmEPV) and *Choristoneura biennis* (CbEPV) is quite different both in terms of amino acid sequence and coding capacity of the corresponding spheroidin genes (115 and 47 kDa for AmEPV and CbEPV, respectively).

The entomopoxviruses and the role of occlusion bodies have recently been reviewed by Arif and Kurstak (Arif, B. M., E. Kurstak, E. [1991 ] "The entomopoxviruses," In *Viruses of Invertebrates* (E. Kurstak, Ed.), pp. 179–195, Marcel Dekker, Inc., New York) and Goodwin et al. (Goodwin, R. H., R. J. Milner, C. D. Beaton [1991] "Entomopoxvirinae," In *Atlas of Invertebrate Viruses* (J. R. Adams and J. R. Bonami, Eds.), pp. 259–285, CRC Press, Inc., Boca Raton). The gene which encodes the AmEPV spheroidin, a 115 kDa protein, has been identified and sequenced (Hall, R. L., R. W. Moyer [1991] *J. Virol.* 65, 6516–6527; Banville, M., F. Dumas, F., S. Trifiro, B. Arif, C. Richardson [1992] J. Gen. Virol. 73, 559–566). The AmEPV gene was also mapped and found to be located at the 3' end of a nucleoside triphosphate phosphohydrolase gene (NPH I or NTPase I, Hall and Moyer [1991], supra). The spheroidin gene of *Choristoneura biennis* entomopoxvirus (CbEPV) has been reported to be derived from a gene capable of encoding a 47 kDa protein (Yuen, L., J. Dionne, B. Arif, C. Richardson [1990] *Virology* 175:427–433.). A comparison of the sequence of the two spheroidins shows no relationship between the two encoded proteins.

We have investigated the spheroidin genes of *Choristoneura biennis, Choristoneura fumiferana*, and *Amsacta moorei* viruses. Our results indicate, in contrast to published results, that the initial Choristoneura EPV spheroidin assignment is likely incorrect and that the Choristoneura spheroidin is instead a highly conserved homolog of the AmEPV spheroidin.

The use of viruses and virus proteins in eukaryotic host-vector systems has been the subject of a considerable amount of investigation and speculation. Many existing viral vector systems suffer from significant disadvantages and limitations which diminish their utility. For example, a number of eukaryotic viral vectors are either tumorigenic or oncogenic in mammalian systems, creating the potential for serious health and safety problems associated with resultant gene products and accidental infections. Further, in some eukaryotic host-viral vector systems, the gene product itself exhibits antiviral activity, thereby decreasing the yield of that protein.

In the case of simple viruses, the amount of exogenous DNA which can be packaged into a simple virus is limited. This limitation becomes a particularly acute problem when the genes used are eukaryotic. Because eukaryotic genes usually contain intervening sequences, they are too large to fit into simple viruses. Further, because they have many restriction sites, it is more difficult to insert exogenous DNA into complex viruses at specific locations.

Vaccinia virus has recently been developed as an eukaryotic cloning and expression vector (Mackett, M., et al. [1985] *DNA Cloning*, Vol. II, ed. D. M. Glover, Oxford: IRL Press, pp. 191–212; Panicali, D., et al. [1982] *Proc. Natl. Acad. Sci. USA*, 88:5364–5368). Numerous viral antigens have been expressed using vaccinia virus vectors (Paoletti, E., et al. [1984] *Proc. Natl. Acad. Sci. USA* 81:193–197; Piccine, A., et al. [1986] *BioEssays* 5:248–252) including, among others, HBsAg, rabies G protein and the gp120/gp41 of human immunodeficiency virus (HIV). Regulatory sequences from the spruce budworm EPV have been used previously with vaccinia (Yuen, L., et al. [1990] *Virology* 175:427–433).

Additionally, studies with vaccinia virus have demonstrated that poxviruses have several advantageous features as vaccine vectors. These include the ability of poxvirus-based vaccines to stimulate both cell-mediated and humoral immunity, minimal cost to mass produce vaccine and the stability of the lyophilized vaccine without refrigeration, ease of administration under non-sterile conditions, and the ability to insert at least 25,000 base pairs of foreign DNA into an infectious recombinant, thereby permitting the simultaneous expression of many antigens from one recombinant.

There exists a need in the art for additional viral compositions and methods for use in expressing heterologous genes in selected host cells, and in performing other research and production techniques associated therewith. In addition, it is noted that the host range of entomopoxviruses is restricted to specific insect hosts which differ from the host range of the baculovirus. Thus, for environmental control of certain pests provision of recombinant entomopoxviruses is desirable.

BRIEF SUMMARY OF THE INVENTION

This invention pertains to novel vectors useful for producing proteins via the expression of an heterologous gene in a novel expression system. More particularly, this invention relates to methods for incorporating a selected heterologous gene (also referred to as exogenous DNA) into a poxvirus genome to produce a recombinant expression vector capable of expression of the selected gene in a host cell.

The expression systems described herein utilize novel structural and/or regulatory DNA elements from Entomopoxvirus genomes. For example, according to the subject invention, the entomopoxvirus spheroidin gene and/or the thymidine kinase gene can be used as the location for the insertion of exogenous DNA. These Entomopoxvirus genes have been discovered to be attractive sites for insertion of heterologous genes because it is possible to transfer the strongly expressed spheroidin gene, or the thymidine kinase gene, as an expression cassette, not only in insect cells, but for use in vertebrate poxviruses such as vaccinia and swinepox virus.

Another aspect of the subject invention pertains to the use of the entomopoxvirus spheroidin or thymidine kinase gene regulatory sequences in other virus vector systems to enhance the performance of those systems. Thus, the subject invention further pertains to the use of regulatory elements from entomopoxvirus to construct novel chimeric vaccines and expression systems which are functional across genera of mammalian poxviruses.

As one aspect, the invention provides novel Entomopoxvirus polynucleotide sequences, free from other viral sequences with which the Entomopoxvirus sequences are associated in nature. Specifically, the subject invention provides nucleotide sequences of Entomopoxvirus spheroidin and thymidine kinase genes, including flanking sequences and regulatory sequences. In particular embodiments, the spheroidin DNA sequence is that which occurs in the *Choristoneura biennis, Choristoneura fumiferana*, or *Amsacta moorei* Entomopoxviruses. Also specifically exemplified is the *Amsacta moorei* Entomopoxvirus thymidine kinase nucleotide sequence. As explained more fully herein, fragments and variants of the exemplified sequences are within the scope of the subject invention. Fragments and variants can be any sequence having substantial homology with the exemplified sequences so long as the fragment or variant retains the utility of the exemplified sequence. One specific type of variant pertains to spheroidin or tk genes from Entomopoxviruses other than those specifically exemplified herein. As described herein, for example, the current inventors have discovered that the spheroidin genes are highly conserved among different species of Entomopoxvirus. Specifically exemplified herein are three different Entomopoxviruse spheroidin genes having a high degree of homology. Other such spheroidin variants or tk variants from other Entomopoxviruses could be readily located and used by the ordinarily skilled artisan having the benefit of the subject application.

As another aspect, the present invention provides recombinant polynucleotide sequences comprising a sequence encoding an Entomopoxvirus spheroidin protein and/or its regulatory sequences, or a variant or fragment of the spheroidin sequence, linked to a second polynucleotide sequence encoding a heterologous gene. One embodiment of such a polynucleotide sequence provides a spheroidin promoter sequence operably linked to a heterologous gene to direct the expression of the heterologous gene in a selected host cell. Another embodiment provides a sequence encoding a spheroidin protein linked to the heterologous gene in a manner permitting expression of a fusion protein. Still another embodiment provides the heterologous gene inserted into a site in a spheroidin gene so that the heterologous gene is flanked on both termini by spheroidin sequences.

Yet a further aspect of the invention provides a recombinant polynucleotide sequence encoding an Entomopoxvirus tk gene and/or its regulatory sequences, or a variant or fragment thereof, linked to a second polynucleotide sequence encoding a heterologous gene. One embodiment of this polynucleotide sequence provides the tk promoter sequence operably linked to the heterologous gene to direct the expression of the heterologous gene in a selected host cell. Another embodiment provides the sequence encoding the tk protein linked to the heterologous gene in a manner permitting expression of a fusion protein. Still another embodiment provides the heterologous gene inserted into a site in the tk gene so that the heterologous gene is flanked on both termini by tk sequences.

Another aspect of the invention pertains to Entomopoxvirus spheroidin polypeptides, fragments thereof, or analogs thereof, optionally fused to a heterologous protein or peptide. Also provided is an Entomopoxvirus tk polypeptide, fragments thereof, or analogs thereof, optionally linked to a heterologous protein or peptide.

Yet another aspect of the invention is provided by recombinant polynucleotide molecules which comprise one or more of the polynucleotide sequences described above. This molecule may be an expression vector or shuttle vector. The molecule may also contain viral sequences originating from a virus other than the Entomopoxvirus which contributed a spheroidin or tk polynucleotide sequence, e.g., vaccinia.

In another aspect, the present invention provides a recombinant virus comprising a polynucleotide sequence as described above. Also provided are host cells infected with one or more of the described recombinant viruses.

The present invention also provides a method for producing a selected polypeptide comprising culturing a selected host cell infected with a recombinant virus, as described above, and recovering said polypeptide from the culture medium.

In another aspect, the invention provides a method for screening recombinant host cells for insertion of heterologous genes comprising infecting the cells with a recombinant virus containing a polynucleotide molecule comprising the selected heterologous gene sequence linked to an incomplete spheroidin or tk polynucleotide sequence or inserted into and interrupting the coding sequences thereof so that the heterologous gene is flanked at each termini by an Entomopoxvirus spheroidin or tk polynucleotide sequence. The absence of occlusion bodies formed by the expression of a spheroidin protein in the spheroidin-containing cell indicates the integration of the heterologous gene. Alternatively, the absence of the thymidine kinase function, i.e., resistance to methotrexate or a nucleotide analogue of methotrexate, formed by the integration of the inactive thymidine kinase sequence indicates the insertion of the heterologous gene.

In another aspect, the invention provides a shuttle vector system that facilitates expression of heterologous genes in insect or mammalian cells.

Other aspects and advantages of the present invention are described further in the following detailed description of embodiments of the present invention.

BRIEF DESCRIPTION OF THE SEQUENCES

SEQ ID NO. 1 is the DNA sequence of the *Amsacta moorei* Entomopoxvirus spheroidin gene and flanking sequences (shown in FIGS. 2 and 7).

SEQ ID NO. 2 is the amino acid sequence encoded by the G1L ORF (shown right to left in FIG. 2).

SEQ ID NO. 3 is the amino acid sequence encoded by the G2R ORF (shown in FIG. 2).

SEQ ID NO. 4 is the amino acid sequence encoded by the G3L ORF (shown right to left in FIG. 2).

SEQ ID NO. 5 is the amino acid sequence encoded by the G4R ORF (shown in FIG. 2).

SEQ ID NO. 6 is the deduced amino acid sequence of the spheroidin protein (shown as G5R ORF in FIG. 2).

SEQ ID NO. 7 is the amino acid sequence encoded by the partial G6L ORF (shown right to left in FIG. 2).

SEQ ID NO. 8 is the DNA sequence of the *Amsacta moorei* Entomopoxvirus thymidine kinase (tk) gene (Q2 ORF) and flanking sequences (shown in FIG. 3).

SEQ ID NO. 9 is a small peptide of 66 amino acids potentially encoded by ORF Q1 (shown right to left in FIG. 3).

SEQ ID NO. 10 is the deduced amino acid sequence of the tk protein (from Q2 ORF; shown right to left in FIG. 3).

SEQ ID NO. 11 is the amino acid sequence encoded by Q3 ORF (shown in FIG. 3).

SEQ ID NO. 12 is the synthetic oligonucleotide designated RM58.

SEQ ID NO. 13 is the synthetic oligonucleotide designated RM82.

SEQ ID NO. 14 is the synthetic oligonucleotide designated RM83.

SEQ ID NO. 15 is the synthetic oligonucleotide designated RM92.

SEQ ID NO. 16 is the synthetic oligonucleotide designated RM118.

SEQ ID NO. 17 is the synthetic oligonucleotide designated RM165.

SEQ ID NO. 18 is the synthetic oligonucleotide designated RM03.

SEQ ID NO. 19 is the synthetic oligonucleotide designated RM04.

SEQ ID NO. 20 is the synthetic oligonucleotide designated RM129.

SEQ ID NO. 21 is the spheroidin gene coding sequence (G5L ORF) spanning nucleotides #3080 through #6091 of SEQ ID NO. 1.

SEQ ID NO. 22 is a fragment of the spheroidin gene spanning nucleotides #2781 through 3199 of SEQ ID NO. 1 which is likely to contain the promoter sequence.

SEQ ID NO. 23 is the G2R ORF (shown in FIG. 2).

SEQ ID NO. 24 is the G4R ORF (shown in FIG. 2).

SEQ ID NO. 25 is the G1L ORF (shown in FIG. 2).

SEQ ID NO. 26 is the G3L ORF (shown in FIG. 2).

SEQ ID NO. 27 is the partial G6L ORF (shown in FIG. 2).

SEQ ID NO. 28 is the tk gene coding sequence (Q2 ORF) spanning nucleotides #234 through #782 of SEQ ID NO. 8.

SEQ ID NO. 29 is a fragment flanking the tk gene spanning nucleotides #783 through #851 of SEQ ID NO. 8.

SEQ ID NO. 30 is a fragment spanning nucleotides #750 through #890 of SEQ ID NO. 8 which is likely to contain the promoter sequence.

SEQ ID NO. 31 is the Q1 ORF (shown in FIG. 3).

SEQ ID NO. 32 is the Q3 ORF (shown in FIG. 3).

SEQ ID NO. 33 is a fragment included within the sequence spanning nucleotides #2274 through #6182 of SEQ ID NO. 1 containing the entire spheroidin open reading frame and some flanking sequences.

SEQ ID NO. 34 is a polypeptide cleavage product according to the subject invention.

SEQ ID NO. 35 is a polypeptide cleavage product according to the subject invention.

SEQ ID NO. 36 is a polypeptide cleavage product according to the subject invention.

SEQ ID NO. 37 is the peptide sequence encoded by the RM58 probe.

SEQ ID NO. 38 is a nucleotide fragment spanning nucleotides #4883 through #4957 of SEQ ID NO. 1.

SEQ ID NO. 39 is a nucleotide fragment spanning nucleotides #3962 through #4012 of SEQ ID NO. 1.

SEQ ID NO. 40 is a nucleotide fragment spanning nucleotides #4628 through #4651 of SEQ ID NO. 1.

SEQ ID NO. 41 is the partial AmEPV NPH I nucleotide sequence (shown in FIG. 7).

SEQ ID NO. 42 is the partial AmEPV NPH I amino acid sequence (shown right to left in FIG. 7).

SEQ ID NO. 43 is the CbEPV nucleotide sequence shown in part A of FIG. 6.

SEQ ID NO. 44 is the CbEPV amino acid sequence shown in part B of FIG. 6.

SEQ ID NO. 45 is the CfEPV nucleotide sequence shown in part A of FIG. 6.

SEQ ID NO. 46 is the CfEPV amino acid sequence shown in part B of FIG. 6.

SEQ ID NO. 47 is the CbEPV amino acid sequence corresponding to amino acids 211 to 221 of AmEPV (shown in part C of FIG. 6).

SEQ ID NO. 48 is the CbEPV amino acid sequence corresponding to amino acids 682 to 691 of AmEPV (shown in part C of FIG. 6).

SEQ ID NO. 49 is the CbEPV amino acid sequence corresponding to amino acids 726–736 of AmEPV (shown in part C of FIG. 6).

SEQ ID NO. 50 is the synthetic oligonucleotide designated RM206.

SEQ ID NO. 51 is the synthetic oligonucleotide designated RM212.

SEQ ID NO. 52 is the synthetic oligonucleotide designated RM58.

SEQ ID NO. 53 is the synthetic oligonucleotide designated RM75.

SEQ ID NO. 54 is the synthetic oligonucleotide designated RM76.

SEQ ID NO. 55 is the synthetic oligonucleotide designated RM78.

SEQ ID NO. 56 is the synthetic oligonucleotide designated RM79.

SEQ ID NO. 57 is the synthetic oligonucleotide designated RM87.

SEQ ID NO. 58 is the synthetic oligonucleotide designated RM91.

SEQ ID NO. 59 is the synthetic oligonucleotide designated RM93.

SEQ ID NO. 60 is the synthetic oligonucleotide designated RM95.

SEQ ID NO. 61 is the synthetic oligonucleotide designated RM169.

SEQ ID NO. 62 is the synthetic oligonucleotide designated RM170.

SEQ ID NO. 63 is the synthetic oligonucleotide designated RM282.

SEQ ID NO. 64 is the synthetic oligonucleotide designated RM283.

SEQ ID NO. 65 is the synthetic oligonucleotide designated pTk1.

SEQ ID NO. 66 is the synthetic oligonucleotide designated pTk2.

SEQ ID NO. 67 is the synthetic oligonucleotide designated pTk3.

SEQ ID NO. 68 is the synthetic oligonucleotide designated pTk4.

SEQ ID NO. 69 is the synthetic oligonucleotide designated pU.

SEQ ID NO. 70 is the synthetic oligonucleotide designated pU2.

SEQ ID NO. 71 is the synthetic oligonucleotide designated pU20.

SEQ ID NO. 72 is the synthetic oligonucleotide designated pD 1.

SEQ ID NO. 73 is the synthetic oligonucleotide designated pD2.

SEQ ID NO. 74 is the complete AmEPV NPH I (G6L ORF) nucleotide sequence (shown in FIGS. 2 and 7).

SEQ ID NO. 75 is the complete AmEPV NPH I amino acid sequence (shown right to left in FIGS. 2 and 7).

SEQ ID NO. 76 is the AmEPV nucleotide sequence (shown in part A of FIG. 6).

SEQ ID NO. 77 is the AmEPV amino acid sequence (shown in part B of FIG. 6).

SEQ ID NO. 78 is the RM58 binding site found in the spheroidin gene.

BRIEF DESCRIPTION OF THE DRAWINGS

FIG. 1 is a physical map of AmEPV illustrating restriction fragments thereof and showing the spheroidin gene (SEQ ID NO. 21) just to the right of site #29 in the HindIII-G fragment.

FIGS. 2A–2P provide the AmEPV DNA sequence of the *Amsacta moorei* Entomopoxvirus spheroidin gene and flanking sequences (SEQ ID NO. 1), the deduced amino acid sequences of the spheroidin protein (SEQ ID NO. 6), and five additional open reading frames (ORFs) (SEQ ID NOs. 23–27). The complete sequence of the G6 ORF is not shown in this figure but is provided in SEQ ID NO. 74.

FIGS. 3A–3D provide the DNA sequence of the *Amsacta moorei* Entomopoxvirus thymidine kinase (tk) gene and flanking sequences (SEQ ID NO. 8), the deduced amino acid sequences of the tk protein (SEQ ID NO. 10), and two additional ORFs.

FIGS. 6A, 6B and 6C show sequences of corresponding regions of the spheroidin-like gene of S CbEPV and CfEPV and the spheroidin of AmEPV. FIG. 6A shows the AmEPV spheroidin sequence (SEQ ID NO. 76) and PCR product sequences derived from CbEPV (SEQ ID NO. 43) and CfEPV (SEQ ID NO. 45) DNA using RM58 (SEQ ID NO. 52) as the sequencing primer for the 1 kb PCR products resulting from the AmEPV spheroidin specific primer pair RM58-RM118 (Table 2) and either CbEPV or CfEPV DNA. The alignment of the Choristoneura EPV sequences with bases 4044–4278 of AmEPV spheroidin is shown. The predicted amino acid sequences from the sequences shown in FIG. 6A are shown in FIG. 6B (SEQ ID Nos. 44, 46, and 77). Identity is shown by vertical lines and two degrees of conserved changes are indicated by periods and colons. FIG. 6C shows CbEPV spheroidin amino acid sequences (SEQ ID NOs. 47–49) derived from protein microsequencing of 3 lys-c endoprotease fragments. Corresponding AmEPV spheroidin sequence and amino acid position numbers are shown.

FIGS. 7A and 7B show the sequence of the 5' end of the AmEPV NPH I gene (SEQ ID NO. 41) including the deduced amino acids (SEQ ID NO. 42). The base numbers represent the extension of the sequence shown in FIG. 2, which includes the partial AmEPV NPH I (NTPase I) gene (SEQ ID NO. 27). The sequence in FIG. 1 ends at base 6768. The base numbers correspond to those in FIG. 8.

DETAILED DESCRIPTION OF THE INVENTION

Figure 4:
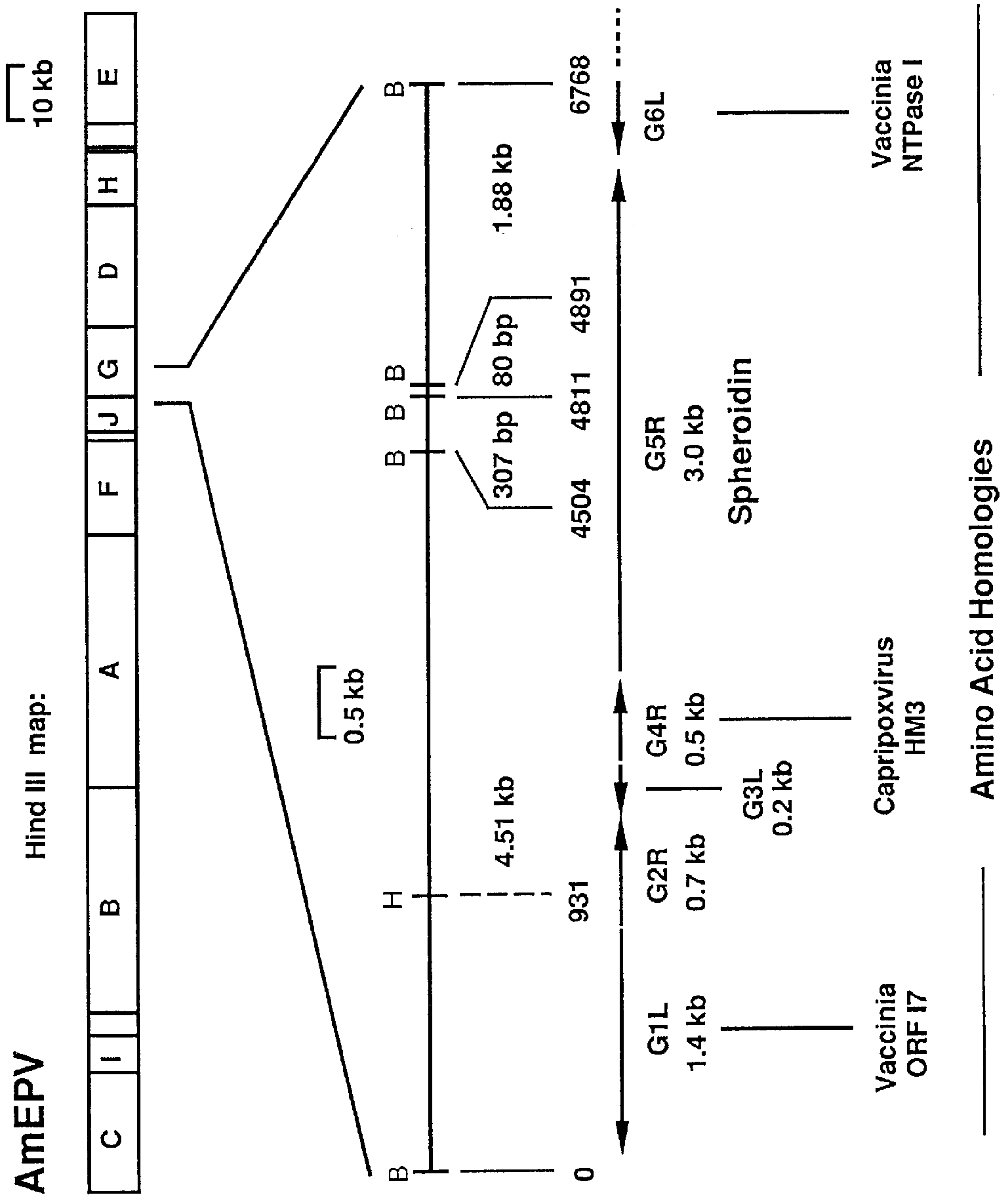
FIG. 4 is a schematic map of an AmEPV fragment illustrating the orientation of the spheroidin ORF on the physical map and indicating homologies.

The present invention provides novel Entomopoxvirus (EPV) polynucleotide sequences free from association with other viral sequences with which they are naturally associated. Recombinant polynucleotide vectors comprising the sequences, recombinant viruses comprising the sequences, and host cells infected with the recombinant viruses are also disclosed herein. These compositions are useful in methods of the invention for the expression of heterologous genes and production of selected proteins in both insect and mammalian host cells.

Novel polynucleotide sequences of the invention encode EPV spheroidin genes and/or flanking sequences, including sequences which provide regulatory signals for the expression of the gene. The invention also provides novel polynucleotide sequences encoding an EPV thymidine kinase (tk) gene and/or its flanking sequences. The polynucleotide sequences of this invention may be either RNA or DNA sequences. More preferably, the polynucleotide sequences of this invention are DNA sequences.

Specifically disclosed by the present invention are spheroidin polynucleotide sequences obtainable from the *Amsacta moorei* Entomopoxvirus (AmEPV), *Choristoneura biennis* Entomopoxvirus (CbEPV), and *Choristoneura fumiferana* Entomopoxvirus (CfEPV). Also specifically exemplified is a tk polynucleotide sequence obtained from AmEPV. While these species are exemplified for practice of the methods and compositions of this invention, utilizing the techniques described herein, substantially homologous sequences may be obtained by one of ordinary skill in the art from other Entomopoxvirus species.

The AmEPV spheroidin DNA sequence, including flanking and regulatory sequences, is reported in FIG. 2 as spanning nucleotides #1 through 6768 (SEQ ID NO. 1). Within this sequence, the spheroidin gene coding sequence spans nucleotides #3080 through #6091 (SEQ ID NO. 21). A fragment which contains the promoter sequences spans nucleotides #2781 through #3199 (SEQ ID NO. 22). More specifically, we show herein that the spheroidin promoter extends beyond the ATG translational start codon and that the promoter is a powerful transcriptional initiator of foreign gene expression. Other regions of that sequence have also been identified as putative coding regions for other structural or regulatory genes associated with spheroidin. These other fragments of interest include the following sequences: the G2R ORF, which is nucleotides #1472 through #2151 (SEQ ID NO. 23) encoding the amino acid sequence shown in SEQ ID NO. 3; the G4 ORF, which is nucleotides #2502 through #2987 (SEQ ID NO. 24) encoding the amino acid sequence shown in SEQ ID NO. 5; and the following sequences transcribed left to right on FIG. 2: the G1L ORF, which is nucleotides #65 through #1459 (SEQ ID NO. 25) encoding the amino acid sequence shown in SEQ ID NO. 2; the G3L ORF, which is nucleotides #2239 through #2475 (SEQ ID NO. 26) encoding the amino acid sequence shown in SEQ ID NO. 4; and the G6 ORF, which includes nucleotides #6277 through #6768 (SEQ ID NO. 27) encoding the amino acid sequence shown in SEQ ID NO. 7. These ORFs are identified in FIG. 2. It should be noted that the full length of the G6 ORF extends beyond nucleotide #6768, is shown in SEQ ID NO. 1 and SEQ ID NO. 41, and is discussed more fully below.

The AmEPV ORF G4R (SEQ ID NO. 24) which encodes G4R (SEQ ID NO. 5) is immediately upstream of the spheroidin gene has significant homology to the capripoxvirus HM3 ORF. A homolog of the HM3 ORF is found in vaccinia virus just upstream of a truncated version of the cowpox virus ATI gene. Therefore, the microenvironments in this region are similar in the two viruses. Two other ORFs relate to counterparts in vaccinia virus. These ORFs include the 17 ORF of the vaccinia virus HindIII-I fragment (17) (Schmitt, J. F. C., et al. [1988] *J. Virol.* 62:1889–1897) which relates to the AmEPV G1L ORF (SEQ ID NO. 25) and the NTPase I (NPH I) ORF of the HindIII-D fragment which relates to the AmEPV G6L ORF (SEQ ID NO. 27) (Broyles, S. S., et al. [1987] *J. Virol.* 61:1738–1742; and Rodriguez, J. F., et al. [1986] *Proc. Natl. Acad. Sci. USA* 83:9566–9570). The genomic location of the AmEPV ORFs compared with that of the vaccinia virus ORFs suggests that the arrangement of essential "core genes," which are centrally located and colinear in many, if not all, of the vertebrate poxviruses on a more macroscopic scale, is quite different in the insect virus.

As set out in detail in the accompanying examples below, the spheroidin gene of AmEPV was identified through direct microsequencing of the protein, and the results were used for the design of oligonucleotide probes. Transcription of the spheroidin gene is inhibited by cycloheximide, suggesting it is a late gene. Consistent with this prediction are the observations that spheroidin transcripts were initiated within a TAAATG motif (See FIG. 2, nucleotide #3077–3082) and that there is a 5' poly(A) sequence, both characteristic of late transcripts.

The isolation and sequencing of the CbEPV and CfEPV spheroidin genes are also described in detail below.

The AmEPV thymidine kinase (tk) DNA sequence, including flanking and regulatory sequences, is reported in FIG. 3, as spanning nucleotides #1 through #1511 (SEQ ID NO. 8). Within this sequence, the tk gene coding sequence spans nucleotides #234 through #782 (SEQ ID NO. 28) (transcribed right to left on FIG. 3). Another fragment of interest may include nucleotides #783 through #851 (SEQ ID NO. 29) of that sequence or fragments thereof. A fragment likely to contain the promoter regions spans nucleotides #750 through #890 (SEQ ID NO. 30). Other regions of that sequence have also been identified as putative coding regions for other structural or regulatory genes associated with tk. These other fragments of interest include the following sequences (transcribed left to right on FIG. 3: ORF Q1, which is nucleotides #18 through #218 (SEQ ID NO. 31) encoding the amino acid sequence shown in SEQ ID NO. 9; and ORF Q3, which is nucleotides #852 through #1511 (SEQ ID NO. 32) encoding the amino acid sequence shown in SEQ ID NO. 11.

The location of the AmEPV tk gene maps in the EcoRI-Q fragment near the left end of the physical map of the AmEPV genome (FIG. 1) (see also, Hall, R. L., et al. [1990] *Arch. Virol.* 110:77–90, incorporated herein by reference). Because of the orientation of the gene within the AmEPV genome, transcription of the gene is likely to occur toward the terminus. There are believed to be similar tk genes, or variations thereof, in other systems, including mammalian systems. As set out in detail in the examples below, the tk gene of AmEPV was identified through direct microsequencing of the protein, and the results were used for the design of oligonucleotide probes.

The term "polynucleotide sequences" when used with reference to the invention can include the entire EPV spheroidin or tk genes with regulatory sequences flanking the coding sequences. The illustrated AmEPV sequences are also encompassed by that term. Also included in the definition are fragments of the coding sequences with flanking regulatory sequences. The definition also encompasses the regulatory sequences only, e.g., the promoter sequences, transcription sites, termination sequences, and other regulatory sequences.

Sequences of the invention may also include all or portions of the spheroidin or tk genes linked in frame to a heterologous gene sequence. Additionally, polynucleotide sequences of the invention may include sequences of the spheroidin or tk genes into which have been inserted a foreign or heterologous gene sequence, so that the EPV sequences flank the heterologous gene sequence.

Polynucleotide sequences of this invention also include sequences which are capable of hybridizing to the sequences of FIGS. 2 and 3, under stringent conditions. Also sequences capable of hybridizing to the sequences of FIGS. 2 and 3 under non-stringent conditions may fall within this definition providing that the biological or regulatory characteristics of the sequences of FIGS. 2 and 3, respectively, are retained. Examples of stringent and non-stringent conditions of hybridization are conventional (see, e.g., Sambrook et al. [1989] *Molecular Cloning. A Laboratory Manual*, 2d edition, Cold Spring Harbor Laboratory, Cold Spring Harbor, N.Y.).

Similarly, polynucleotide sequences of this invention also include variants, including allelic variations (naturally-occurring base changes in the EPV species population which may or may not result in an amino acid change) of DNA sequences encoding the spheroidin or tk protein sequences or other ORFs or regulatory sequences illustrated in FIGS. 2 and 3. Similarly, DNA sequences which encode spheroidin or tk proteins of the invention but which differ in codon sequence due to the degeneracies of the genetic code or variations in the DNA sequences which are caused by point mutations or by induced modifications to, for example, enhance a biological property or the usefulness of a desired polynucleotide sequence encoded thereby are also encompassed in the invention.

Utilizing the sequence data in FIGS. 2 or 3, as well as the denoted characteristics of spheroidin or thymidine kinase, it is within the skill of the art to obtain other DNA sequences encoding these polypeptides. For example, the structural gene may be manipulated by varying individual nucleotides, while retaining the same amino acid(s), or varying the nucleotides, so as to modify the amino acids, without loss of utility. Nucleotides may be substituted, inserted, or deleted by known techniques, including, for example, in vitro mutagenesis and primer repair.

The structural gene may be truncated at its 3'-terminus and/or its 5'-terminus. It may also be desirable to ligate a portion of the polypeptide sequence to a heterologous coding sequence, and thus to create a fusion peptide.

The polynucleotide sequences of the present invention may be prepared by a variety of techniques well known to those skilled in the art. The sequences may be prepared synthetically or can be derived from viral RNA or from available cDNA-containing plasmids by chemical and genetic engineering techniques or combinations thereof which are standard in the art.

The Entomopoxvirus proteins—spheroidin, thymidine kinase and their respective regulatory sequences, as described herein—may be encoded by polynucleotide sequences that differ in sequence from the sequences of FIGS. 2 and 3 due to, for example, natural allelic or species variations. Thus, the terms spheroidin or tk polypeptides also refer to any of the naturally occurring sequences and various analogs, e.g., processed or truncated sequences or fragments, including the mature spheroidin or tk polypeptides and mutant or modified polypeptides or fragments that retain the same utility and preferably have homology to FIG. 2 or 3, respectively, of at least 75%, more preferably 90%, and most preferably 95%.

Another aspect of the present invention is provided by the proteins encoded by the EPV spheroidin and tk polynucleotide sequences. Putative amino acid sequences of the two EPV proteins as well as additional putative proteins encoded by the ORFs of these sequences which are identified in FIGS. 2 and 3, respectively. EPV spheroidin has no significant amino acid homology to any previously reported protein, including the polyhedrin protein of baculovirus. We have found that both spheroidin and tk are nonessential proteins, which makes them desirable as sites for insertion of exogenous DNA.

Comparison of the AmEPV tk amino acid sequence with other tk genes reveals that the AmEPV tk gene is not highly related to any of the vertebrate poxvirus tk genes (43.4 to 45.7%). The relatedness of the vertebrate tk proteins to AmEPV is still lower (39.3 to 41.0%), while African Swine Fever (ASF) showed the least homology of all the tk proteins tested (31.4%). Although ASF has many similarities to poxviruses, and both ASF and AmEPV infect vertebrate hosts, the tk genes indicate little commonality and/or indication of common origin stemming from invertebrate hosts.

The spheroidin and thymidine kinase polypeptide sequences may include isolated naturally-occurring spheroidin or tk amino acid sequences identified herein or deliberately modified sequences which maintain the biological or regulatory functions, or other utility, of the AmEPV polypeptides, respectively identified in FIGS. 2 and 3. Therefore, provided that the utilities of these polypeptides are retained in whole or part despite such modifications, this invention encompasses the use of all amino acid sequences disclosed herein as well as variants thereof retaining spheroidin or tk utility. Similarly, proteins or functions encoded by the other spheroidin or tk ORFs may include sequences containing amino acid modifications but which retain their regulatory or other biological functions, or other utility.

Examples of such modifications include polypeptides with amino acid variations from the natural amino acid sequence of Entomopoxvirus spheroidin or thymidine kinase; in particular, conservative amino acid replacements. Conservative replacements are those that take place within a family of amino acids that are related in their side chains. Genetically encoded amino acids are generally divided into four families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on biological activity, especially if the replacement does not involve an amino acid at an active site of the polypeptides.

As used herein, the term "polypeptide" refers to a polymer of amino acids and does not refer to a specific length of the product; thus, peptides, oligopeptides, and proteins are included within the definition of polypeptide. The phrase "polypeptide and variants thereof" includes post-expression modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The proteins or polypeptides of the present invention may be expressed in host cells and purified from the cells or media by conventional means (Sambrook et al., supra).

This invention also relates to novel viral recombinant polynucleotide molecules or vectors, which permit the expression of heterologous genes in a selected host cell. Such a polynucleotide vector of the invention comprises the polynucleotide sequence encoding all or a portion of the spheroidin or tk gene, the RNA polymerase from a selected poxvirus, and the polynucleotide sequence encoding a desired heterologous gene. Preferably, the sequence includes the regulatory region, and most preferably, the promoter region, of either the EPV spheroidin or tk gene. In addition, the source of the polymerase is not limited to EPV; rather, any poxvirus RNA polymerase may be utilized.

Therefore, the viral vectors may contain other viral elements contributed by another poxvirus, either vertebrate or invertebrate, with the only EPV sequences being provided by the presence of the EPV spheroidin or tk gene sequences, or fragments thereof. Numerous conventional expression viral vectors and expression systems are known in the art. Particularly desirable vectors systems are those of vertebrate or invertebrate poxviruses. The Entomopoxvirus spheroidin and tk gene regulatory sequences may be used in other virus vector systems which contain a poxvirus RNA polymerase to enhance the performance of those systems, e.g., in vaccinia vectors. Methods for the construction of expression systems, in general, and the components thereof, including expression vectors and transformed host cells, are within the art. See, generally, methods described in standard texts, such as Sambrook et al., supra. The present invention is therefore not limited to any particular viral expression system or vector into which a polynucleotide sequence of this invention may be inserted, provided that the vector or system contains a poxvirus RNA polymerase.

The vectors of the invention provide a helper independent vector system, that is, the presence or absence of a functional spheroidin or tk gene in a poxvirus contributing elements to the vector, e.g., contributing the RNA polymerase, does not affect the usefulness of the resulting recombinant viral vector. Because both spheroidin and tk are non-essential genes, the viral vectors of this invention do not require the presence of any other viral proteins, which in helper-dependent systems are contributed by additional viruses to co-infect the selected host cell.

Selected host cells which, upon infection by the viral vectors will permit expression of the heterologous gene, include insect and mammalian cells. Specifically, if the viral vector comprises the EPV spheroidin or tk gene sequences of the invention inserted into any member of the family Entomopoxvirinae, e.g., EPVs of any species, the host cell will be limited to cells of insects normally infected by EPVs. If the viral vector comprises the EPV spheroidin or tk gene sequences of the invention inserted into a vertebrate poxvirus, such as vaccinia or swinepox, the host cells may be selected from among the mammalian species normally infected by the wild-type vertebrate poxvirus. Most desirably, such mammalian cells may include human cells, rodent cells and primate cells, all known and available to one of skill in the art.

According to one aspect of the subject invention, therefore, vectors of the present invention may utilize a fragment of the polynucleotide sequence of EPV spheroidin, particularly the promoter and ancillary regulatory sequences which are responsible for the naturally high levels of expression of the gene. Desirably, spheroidin sequences may be found within the sequence of FIG. 2 (SEQ ID NO. 1), more particularly within the region of nucleotides #2781 through 3199 (SEQ ID NO. 22). Smaller fragments within that region may also provide useful regulatory sequences. The desired spheroidin promoter sequence can be utilized to produce large quantities of a desired protein by placing it in operative association with a selected heterologous gene in viral expression vectors capable of functioning in either a vertebrate or invertebrate host cell.

As used herein, the term "operative association" defines the relationship between a regulatory sequence and a selected protein gene, such that the regulatory sequence is capable of directing the expression of the protein in the appropriate host cell. One of skill in the art is capable of operatively associating such sequences by resort to conventional techniques.

Where the spheroidin polynucleotide sequence in the vector contains all or a portion of the spheroidin coding sequence in association with, or linked to, the heterologous gene, the resulting protein expressed in the host cell may be a fusion protein consisting of all or a portion of the spheroidin protein and the heterologous protein. Where the spheroidin polynucleotide sequence in the vector does not contain sufficient coding sequence for the expression of a spheroidin protein or peptide fragment, the heterologous protein may be produced alone.

In an analogous manner, the promoter and regulatory sequences of tk (FIG. 3 SEQ ID NO. 8) may be employed in the construction of an expression vector to drive expression of a heterologous protein, or a fusion protein, in a selected known expression system. These tk regulatory sequences are desirably obtained from the sequence of FIG. 3 (SEQ ID NO. 8), particularly in the fragment occurring between nucleotide #750 through 890 (SEQ ID NO. 30). Smaller fragments within that region may also provide useful regulatory sequences.

An advantage of the use of the novel EPV spheroidin or tk promoter sequences of this invention is that these regulatory sequences are capable of operating in a vertebrate poxvirus (e.g., vaccinia)-mammalian cell expression vector system. For example, the strong spheroidin promoter can be incorporated into the vaccinia virus system through homologous recombination. Unlike the promoter for the baculovirus polyhedrin gene, the promoter for the EPV spheroidin gene can be utilized directly in the vaccinia or swinepox virus expression vector.

To construct a vector according to the present invention, the spheroidin or tk polynucleotide sequence may be isolated and purified from a selected Entomopoxvirus, e.g., AmEPV, and digested with appropriate restriction endonuclease enzymes to produce a fragment comprising all or part of the spheroidin or tk gene. Alternatively such a fragment may be chemically synthesized.

Still alternatively, the desired AmEPV sequences may be obtained from bacterial cultures containing the plasmids pRH512, pMEGtk-1 or pRH7. The construction of the plasmid pRH512 is described in the examples below. This plasmid contains the 4.51 kb BglII fragment AmEPV DNA sequence inserted into a BamHI site in the conventional vector pUC9. The plasmid pRH7 was constructed by digesting AmEPV genomic DNA, obtained as described in Example 1, with Bsp1286I, and the resulting fragments with HaeII. T4 DNA polymerase is employed to blunt end the AmEPV DNA and the fragment containing the spheroidin gene is ligated to the large fragment of a SmaI digested pUC9 fragment. This fragment contains the entire spheroidin open reading frame and some flanking sequence, included within the nucleotide sequence spanning #2274–6182 (SEQ ID NO. 33) of FIG. 2. The construction of plasmid pMEGtk-1 comprising the regulatory sequences of the tk gene as well as the structural gene is described below in the Example 8. It was constructed by inserting the EcoRI-Q fragment of AmEPV into the conventional vector pUC18.

Bacterial cultures containing plasmids pRH512, pMEG tk-1, and pRH7 have been deposited in the American Type Culture Collection, 12301 Parklawn Drive, Rockville, Md., USA. The deposited cultures are as follows:

| Culture | Accession No. | Deposit Date |
|---|---|---|
| *E. coli* SURE strain (Stratagene) pMEG-tk1 | ATCC 68532 | February 26, 1991 |
| *E. coli* SURE strain (Stratagene) pRH512 | ATCC 68533 | February, 26 1991 |
| *E. coli* SURE strain (Stratagene) pRH7 | ATCC 68902 | January 28, 1992 |

The plasmids can be obtained from the deposited bacterial cultures by use of standard procedures, for example, using cleared lysate-isopycnic density gradient procedures, and the like.

These ATCC deposits were made under conditions that assure that access to the cultures will be available during the pendency of this patent application to one determined by the Commissioner of Patents and Trademark to be entitled thereto under 37 CFR 1.14 and 35 USC 122. The deposits will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least 30 (thirty) years after the date of deposit or for the enforceable life of any patent which may issue disclosing the cultures. The depositor acknowledges the duty to replace the deposit (s) should the depository be unable to furnish a sample when requested, due to the condition of a deposit. All restrictions on the availability to the public of the subject culture deposits will be irrevocably removed upon the granting of a patent disclosing them.

The molecular biology procedures referred to herein in describing construction of the vectors of this invention are standard, well-known procedures. The various methods employed in the preparation of the plasmid vectors and transformation or infection of host organisms are well-known in the art. These procedures are all described in, for example, Sambrook et al., cited above. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

Because the AmEPV genome has no known unique restriction sites into which selected genes may be effectively introduced in a site-specific manner so as to be under the control of the spheroidin or tk promoter sequences, such restriction sites must be introduced into desired sites in the selected EPV polynucleotide sequence. For example, the unique BstB1 site located at nucleotide #3172 downstream from the start of the spheroidin gene is the closest site to genetically engineer a usable insertion sequence for cloning. Therefore, restriction sites closer to the initiating Met of the spheroidin gene must be deliberately inserted.

Methods for the insertion of restriction sites are known to those of skill in the art and include, the use of an intermediate shuttle vector, e.g., by cloning the EPV sequence into the site of an appropriate cloning vehicle. It will be recognized by those skilled in the art that any suitable cloning vehicle may be utilized provided that the spheroidin or tk gene and flanking viral DNA may be functionally incorporated.

A spheroidin shuttle vector may be constructed to include elements of the spheroidin structural gene, a cloning site located or introduced in the gene to enable the selected heterologous gene to be properly inserted into the viral genome adjacent to, and under the control of, the spheroidin promoter, and flanking viral DNA linked to either side of the spheroidin gene to facilitate insertion of the spheroidin-foreign gene-flanking sequence into another expression vector. The presence of flanking viral DNA also facilitates recombination with the wild type Entomopoxvirus, allowing the transfer of a selected gene into a replicating viral genome.

The shuttle vectors may thereafter be modified for insertion of a selected gene by deleting some or all of the sequences encoding for spheroidin or tk synthesis near the respective transcriptional start sites. Examples of such sites in spheroidin are nucleotides #3077 and 3080 and in tk includes nucleotide #809. Conventional procedures are available to delete spheroidin or tk coding sequences.

As an alternative to or in addition to the restriction site, a variety of synthetic or natural oligonucleotide linker sequences may be inserted at the site of the deletion. A polynucleotide linker sequence, which may be either a natural or synthetic oligonucleotide, may be inserted at the site of the deletion to allow the coupling of DNA segments at that site. One such linker sequence may provide an appropriate space between the two linked sequences, e.g., between the promoter sequence and the gene to be expressed. Alternatively, this linker sequence may encode, if desired, a polypeptide which is selectively cleavable or digestible by conventional chemical or enzymatic methods. For example, the selected cleavage site may be an enzymatic cleavage site, including sites for cleavage by a proteolytic enzyme, such as enterokinase, factor Xa, trypsin, collegenase and thrombin. Alternatively, the cleavage site in the linker may be a site capable of being cleaved upon exposure to a selected chemical, e.g. cyanogen bromide or hydroxylamine. The cleavage site, if inserted into a linker useful in the sequences of this invention, does not limit this invention. Any desired cleavage site, of which many are known in the art, may be used for this purpose. In another alternative, the linker sequence may encode one or a series of restriction sites.

It will be recognized by those skilled in the art who have the benefit of this disclosure that linker sequences bearing an appropriate restriction site need not be inserted in place of all or a portion of the spheroidin structural sequence, and that it would be possible to insert a linker in locations in the Entomopoxvirus genome such that both the sequence coding for the selected polypeptide and the spheroidin structural sequence would be expressed. For instance, the sequence coding for the selected polypeptide could be inserted into the tk gene in place of all or a portion of the tk structural sequence and under the transcriptional control of the tk promoter.

Polymerase chain reaction (PCR) techniques can also be used to introduce convenient restriction sites into the EPV DNA, as well as to amplify specific regions of the EPV DNA. These techniques are well known to those skilled in this art. See, for example, *PCR Protocols: A Guide to Methods and Applications*, M. A. Innis, D. H. Gelfand, J. J. Sninsky, and T. J. White, (1990).

By use of these techniques, a variety of alternative modified shuttle vectors into which a selected gene or portion thereof may be incorporated may be suitably utilized in the present invention. Specific examples of such constructs and their use in the production of recombinant entomopoxvirus and vaccinia viruses are provided herein.

As one embodiment of the invention, therefore, the polynucleotide sequence, described above, may be used as a shuttle vector to transfer a selected heterologous gene to a selected virus. In this embodiment, the polynucleotide sequence encoding the EPV spheroidin gene or EPV tk gene, or a fragment thereof, is linked to a heterologous gene. The polynucleotide sequence further contains a flanking region on either side of the spheroidin-heterologous gene or tk-heterologous gene to enable ready transfer into a selected virus. This resulting construct is termed a cassette. Such a flanking region may be derived from EPV, or alternatively, may be complementary to the target virus. For example, if it is desirable to insert a selected heterologous gene into a vaccinia virus to create a recombinant virus, one would utilize flanking regions complementary to the targeted vaccinia virus. Similarly if the heterologous gene is inserted within the EPV spheroidin or tk gene, so that the selected EPV regulatory sequence and heterologous gene are flanked by the EPV gene's own sequences, this cassette may be used for transfer into a wild type EPV having homologous sequences to the flanking sequences.

The insertion or linkage of the foreign gene into the tk or spheroidin sequences of the present invention or the linkage of flanking sequences foreign to the spheroidin or tk genes may be accomplished as described above. The vectors of the subject invention may use cDNA clones of foreign genes, because poxvirus genes contain no introns, presumably as a consequence of a totally cytoplasmic site of infection.

In accordance with standard cloning techniques, any selected gene may be inserted into the vector at an available restriction site to produce a recombinant shuttle vector. Virtually any gene of interest could be inserted into the vectors described herein in order to obtain high expression of the desired protein. The spheroidin gene product may be useful as a particulate biological carrier for foreign gene antigens. Thus, a foreign gene fused to the spheroidin gene may be useful as a method to produce a foreign protein attached to an effective vaccine carrier. Restriction sites in the fragment may thereafter be removed so as to produce a preferred spheroidin or tk shuttle vector, having one or more cleavage or cloning sites located in the 3' direction downstream from the spheroidin promoter sequence. Thus, the present invention is not limited by the selection of the heterologous gene.

Alternatively, a vector of this invention may comprise a heterologous gene which is inserted into all or a portion of the EPV spheroidin or tk protein encoding sequence to interrupt the protein's natural processing. However, when the vector is transferred to another virus which contains a wild-type spheroidin or tk gene, expression of the inserted heterologous gene is obtained. Thus, the Entomopoxvirus spheroidin gene (FIG. 2; SEQ ID NO. 1) and/or the tk gene (FIG. 3; SEQ ID NO. 8) can be used as the location for the insertion of exogenous (heterologous) DNA in any of the above-mentioned expression systems. A shuttle vector so constructed may be useful as a marker for research and production techniques for identifying the presence of successfully integrated heterologous genes into the selected expression system.

The tk gene is a particularly desirable site for insertion of a selected heterologous gene. Unlike spheroidin, tk is produced early in infection and in lesser quantities. Additionally, many poxviruses possess tk genes which may be sufficiently homologous to the EPV tk to provide easy recombination. For example, in vaccinia virus expression systems for mammalian cells, the vaccinia tk gene is a common insertion site. Therefore, the use of this gene is particularly desirable for construction of a shuttle vector to shuttle selected genes directly between vector systems. More specifically, a foreign gene may be desirably inserted into the EPV tk gene sequence between nucleotide #460 and #560 (See FIG. 3).

Insertion of cassettes containing foreign genes into wild-type poxviruses can be accomplished by homologous recombination. The homologous recombination techniques used to insert the genes of interest into the viruses of the invention are well known to those skilled in the art. The shuttle vectors, when co-infected into host cells with a wild-type virus, transfer the cassette containing the selected gene into the virus by homologous recombination, thereby creating recombinant virus vectors.

Expression of a selected gene is accomplished by infecting susceptible host insect cells with the recombinant viral vector of this invention in an appropriate medium for growth. An EPV expression vector is propagated in insect cells or insects through replication and assembly of infectious virus particles. These infectious vectors can be used to produce the selected gene in suitable insect cells, thus facilitating the efficient expression of the selected DNA sequence in the infected cell. If the EPV spheroidin gene (or tk gene)-heterologous gene fragment is inserted into a vertebrate poxvirus by the same methods as described above, the recombinant virus may be used to infect mammalian cells and produce the heterologous protein in the mammalian cells.

For example, a gene inserted into the tk site of a vaccinia virus system could be transferred directly to the tk locus of an Entomopoxvirus vector of the subject invention or vice versa. This shuttling could be accomplished, for example, using homologous recombination. Similarly insertion of a selected gene into the spheroidin gene or tk gene in a viral vector permits the gene to be shuttled into other viruses having homologous spheroidin or tk sequences, respectively.

The following description illustrates an exemplary vector of this invention, employing the gene coding for human β-interferon (IFN-β) synthesis as the heterologous gene. A DNA fragment containing the IFN-β gene is prepared conventionally with restriction enzyme digested or blunt ended termini and cloned into a suitable site in the AmEPV spheroidin gene, into which a restriction site has been engineered by the methods described above.

The insertion of the IFN-β gene produces a hybrid or fused spheroidin-IFN-β gene capable of producing a fused polypeptide product if only a portion of the spheroidin gene was deleted as described above. If the entire spheroidin structural sequence was deleted, only interferon will be produced. Further, the hybrid gene may comprise the spheroidin promoter, the IFN-β protein coding sequences, and sequences encoding a portion of the polypeptide sequence of the spheroidin protein, provided all such coding sequences are not deleted from the particular shuttle vector utilized.

The resulting shuttle vector contains the AmEPV spheroidin gene sequence coupled to the IFN-β gene. The hybrid spheroidin-IFN-β gene of the recombinant shuttle vector is thereafter transferred into the genome of an appropriate Entomopoxvirus, such as the preferred Entomopoxvirus AmEPV, to produce a recombinant viral expression vector capable of expressing the gene encoding for β-interferon in a host insect cell. Transfer of the hybrid gene to a wild-type virus is accomplished by processes which are well known to those skilled in the art. For example, appropriate insect cells may be infected with the wild type Entomopoxvirus. These infected cells are then transfected with the shuttle vector of the subject invention. These procedures are described, for example, in *DNA Cloning: A Practical Approach*, Vol. II, Edited by D. M. Glover, Chapter 7, 1985. A person skilled in the art could choose appropriate insect cells to be used according to the subject invention. By way of example, salt marsh caterpillars and cultured gypsy moth cells can be used.

During replication of the AmEPV DNA after transfection, the hybrid gene is transferred to the wild-type AmEPV by homologous recombination between the recombinant shuttle vector and AmEPV DNA. Accordingly, a mixture is produced comprising wild-type, nonrecombinant EPVs and recombinant EPVs capable of expressing the IFN-β gene.

While transfection is the preferred process for transfer of the hybrid gene into the EPV genome, it will be understood by those skilled in the art that other procedures may be suitably utilized so as to effect the insertion of the gene into the EPV genome and that recombination may be accomplished between the recombinant shuttle vector and other strains of EPV (or other poxviruses) so long as there is sufficient homology between the sequence of the hybrid gene and the corresponding sequence of the other strain to allow recombination to occur.

The preferred recombinant AmEPV expression vector, comprising a hybrid spheroidin-IFN-β gene incorporated into the AmEPV genome, can thereafter be selected from the mixture of nonrecombinant and recombinant Entomopoxviruses. The preferred, but by no means only, method of selection is by screening for plaques formed by host insect cells infected with viruses that do not produce viral occlusions. Selection may be performed in this manner because recombinant EPV viruses which contain the spheroidin or tk protein coding sequences interrupted by the heterologous gene are defective in the production of viral occlusions due to the insertional inactivation of the spheroidin gene.

Also, the selection procedure may involve the use of the β-galactosidase gene to facilitate color selection. This procedure involves the incorporation of the *E. coli* β-galactosidase gene into the shuttle vector and is well known to those skilled in the art. This technique may be of particular value if the exogenous DNA is inserted into the tk gene so that the spheroidin gene is still expressed. It will be recognized by those skilled in the art that alternative selection procedures may also be utilized in accordance with the present invention.

Accordingly, the DNA from a recombinant virus is thereafter purified and may be analyzed with appropriate restriction enzymes, or PCR technology, to confirm that the recombinant AmEPV vector has an insertion of the selected gene in the proper location.

The vectors and methods provided by the present invention are characterized by several advantages over known vectors and vector systems. Advantageously, such EPV viral vectors of the present invention are not oncogenic or tumorigenic in mammals. Also, the regulatory signals governing *Amsacta moorei* Entomopoxvirus (AmEPV) gene expressions are similar to those of vaccinia. Therefore, it is possible to transfer the strongly expressed spheroidin gene, or the thymidine kinase gene, as an expression cassette, not only in insect cells, but for use in vertebrate poxviruses such as vaccinia and swinepox virus.

Based on reported data with vaccinia, herpes and baculovirus vector systems, which suggest that up to 30 kb can be transferred without disrupting the vector viability, the normal limitation on the amount of exogenous DNA which can be packaged into a virus is not anticipated to be encountered when using the novel EPV vectors and methods of the subject invention.

Another advantage is that for the novel vectors of the subject invention, the transcription and translation of foreign proteins is totally cytoplasmic. Still another advantage lies in the expression power of the EPV spheroidin regulatory sequences, which when in operative association with a heterologous gene in a vector of this invention, can be used to produce high levels of heterologous protein expression in the selected host cell.

The EPV vectors of this invention and methods for employing them to express selected heterologous proteins in insect or mammalian cells, as described above, are characterized by the advantage of replication in insect cells, which avoids the use of mammalian viruses, thereby decreasing the possibility of contamination of the product with mammalian virus. The expression system of this invention is also a helper independent virus expression vector system. These two characteristics are shared by known baculovirus expression systems. However, as shown in Table 1, the EPV expression vector system (EEVS) using the vectors of this invention has some important distinguishing features compared to the baculovirus expression systems (BEVS).

TABLE 1

Differences between EEVS and BEVS

| | EEVS | EEVS |
|---|---|---|
| Site of replication: | cytoplasm | nucleus |
| Virus family: | *Poxviridae* | *Baculoviridae* |
| Sites for insertion of foreign genes: | spheroidin & thymidine kinase (tk) | polyhedrin & p10 |
| Shuttle possibilities between vertebrate and insect systems: | (Orthopoxviruses) (Leporipoxviruses) (Suipoxviruses) (Avipoxviruses) | No mammalian counterparts. Baculovirus is not known to contain a tk gene. Polyhedrin is not found in mammalian systems. |

The present invention also provides a method for screening recombinant host cells for insertion of heterologous genes by use of the recombinant viral polynucleotide molecules of this invention. The viral molecules containing the selected heterologous gene sequence linked to the polynucleotide sequence encoding less than all of the Entomopoxvirus spheroidin protein. The heterologous gene may be linked to the spheroidin or tk regulatory sequences in the absence of the complete coding sequences, or it may be inserted into the spheroidin or tk gene coding sequences, thus disrupting the coding sequence. The cell infected with the recombinant vector is cultured under conditions suitable for expression of the heterologous protein, either unfused or as a fusion protein with a portion of the spheroidin sequence. The absence of occlusion bodies which would ordinarily be formed by the expression of the intact spheroidin protein indicates the integration of the heterologous gene.

If the viral vector similarly contained either incomplete or interrupted EPV tk encoding sequence, the absence of thymidine kinase function (e.g., resistance to methotrexate or an analogue thereof) formed by the integration of the inactive thymidine kinase sequence indicates the insertion of the heterologous gene. Alternatively, if a parent virus is deleted of part of its tk or spheroidin gene, and is thereafter mixed with a viral vector containing intact tk or spheroidin fused to the foreign gene, recombinants would express the methotrexate resistance or produce occlusion bodies, respectively, thus indicating integration of the active tk or spheroidin genes and the foreign gene.

The above-described selection procedures provide effective and convenient means for selection of recombinant Entomopoxvirus expression vectors.

Another embodiment of the present invention involves using novel EPV expression systems of the subject invention for insect control. Control of insect pests can be accomplished by employing the vectors and methods of the invention as described above. For example, a gene coding for an selected insect toxin may be inserted into the viral expression vector under the control of the spheroidin or tk regulatory sequences or within either of the two genes for purposes of recombination into a selected virus having homologous flanking regions.

Genes which code for insect toxins are well known to those skilled in the art. An exemplary toxin gene isolated from *Bacillus thuringiensis* (*B. t.*) can be used according to the subject invention. *B. t.* genes are described, for example, in U.S. Pat. Nos. 4,775,131 and 4,865,981. Other known insect toxins may also be employed in this method.

The resulting EPV vector containing the toxin gene is applied to the target pest or its surroundings. Advantageously, the viral vector will infect the target pest, and large quantities of the toxin will be produced, thus resulting in the control of the pest. Particularly large quantities of the toxin protein can be produced if the regulatory sequences of the Entomopoxvirus spheroidin gene are used to express the toxin.

Alternatively, the spheroidin gene can be left intact and the toxin gene inserted into a different Entomopoxvirus gene such as the tk gene. In this construct, the toxin will be produced by the system and then effectively coated or encapsulated by the natural viral production of spheroidin. This system thus produces a toxin which will advantageously persist in the environment to prolong the availability to the target pest.

In addition to the novel Entomopoxvirus expression vectors and methods for their use described herein, the subject invention pertains to the use of novel regulatory elements from Entomopoxvirus to construct novel chimeric vaccinia and swinepox vaccines and expression systems which are functional across genera of mammalian poxviruses. The polynucleotide sequences of the invention can also be used with viral vaccines, e.g., known vaccinia virus vaccines, to enhance the effectiveness of these vaccines. Such vaccines have been described for use in controlling rabies and other infectious diseases in mammals. Specifically, it is anticipated that the introduction of the EPV spheroidin promoter sequences into known viral vectors which are used to express selected proteins in a mammalian host in vivo may enable the powerful spheroidin promoter to increase expression of the protein in the viral vaccine. This aspect of the invention provides a significant improvement over other expression systems, including the baculovirus expression system (BEVS).

The following examples illustrate the compositions and procedures, including the best mode, for practicing the invention. These examples, should not be construed as limiting. All percentages are by weight and all solvent mixture proportions are by volume unless otherwise noted. The restriction enzymes disclosed herein can be purchased from Bethesda Research Laboratories, Gaithersburg, Md., or New England Biolabs, Beverly, Mass. The enzymes are used according to the instructions provided by the supplier. Klenow fragment of DNA polymerase, T4 polynucleotide kinase, and T4 DNA ligase were obtained from New England Biolabs and Promega.

EXAMPLE 1

Preparation of AmEPV DNA

The replication of AmEPV has been described previously (Goodwin, R. H., et al. [1990] *J. Invertebr. Pathol.* 56:190–205). The gypsy moth (*Lymantria dispar*) cell line IPLB-LD-652 (Insect Pathology Laboratory, Agricultural Research Service, U.S. Department of Agriculture, Beltsville, Md.) is maintained at 26 to 28° C. in EX-CELL 400 (JRH Biosciences, Lenexa, Kans.) supplemented with 10% fetal bovine serum, 100 U of penicillin, and 100 $\mu$g of streptomycin per ml. Other insect cell lines are well known to those skilled in the art and can be used according to the subject invention.

The AmEPV inoculum for cell culturing was from an AmEPV-infected, freeze-dried *E. acrea* larva stored at −70°

C. (Hall, R. L., et al. [1990] *Arch. Virol.* 110:77–90). The larva was crushed and macerated in 5 ml of EX-CELL 400 (with penicillin and streptomycin but without fetal bovine serum) to which 0.003 g of cysteine-HCl had been added to prevent melanization. The debris was pelleted at 200×g for 5 minutes, and the supernatant was passed through a 0.45-$\mu$m-pore-size filter.

The gypsy moth cells were infected with AmEPV by addition of the inoculum to a preconfluent monolayer of cells (about 0.1 to 1 PFU per cell), with occasional agitation of the dish during the first day. Infected cells were harvested 5 to 6 days postinfection.

AmEPV DNA was prepared from the infected cells by one of two methods. The first method involved in situ digestion of infected cells embedded within agarose plugs, after which the released cellular and viral DNAs were separated by pulsed-field electrophoresis (Bio-Rad CHEF-II-DR system). IPLB-LD-652 cells were infected with first-cell-culture-passage AmEPV. Infected cells were harvested 6 days postinfection by centrifugation at 200×g for 5 minutes, rinsed, and resuspended in modified Hank's phosphate-buffered saline (PBS), which contained 15 g of glucose per liter, but no $Ca^{2+}$ or $Mg^{2+}$.

For embedding of the infected cells in agarose plugs, 1% SeaPlaque GTG agarose (prepared in modified Hank's PBS and equilibrated at 37° C.) was mixed 1:1 with infected cells to yield $5\times10^6$ cells per ml in 0.5% agarose. Digestion to release DNA was done by gentle shaking of the inserts in 1% Sarkosyl-0.5 M EDTA-1 mg of proteinase K per ml at 50° C. for 2 days (Smith, C. L., et al. [1987] *Methods Enzymol.* 151:461–489). The CHEF-II-DR parameters for DNA separation were 180 V, a pulse ratio of 1, 50 initial and 90 second final pulse times, and a run time of 20 to 25 hours at 4° C. The separating gel was 1% SeaKem GTG agarose in 0.5× TBE buffer (Sambrook et al., supra). Viral DNA bands were visualized by ethidium bromide staining and electroeluted (Allington, W. B., et al. [1978]*Anal. Biochem.* 85:188–196). The recovered DNA was used for plasmid cloning following ethanol precipitation.

The second method of viral DNA preparation used the extracellular virus found in the infected-cell-culture supernatant. The supernatant from 10-day-postinfection cell cultures was clarified by centrifugation at 200×g for 5 minutes. Virus was collected from the supernatant by centrifugation at 12,000×g. Viral pellets were resuspended in 6 ml of 1×TE. DNase I and RNase A (10 and 20 $\mu$g/ml final concentrations, respectively) were added, and the mixture was incubated at 37° C. for 30 minutes. The mixture was heated to 50° C. for 15 minutes. SDS and proteinase K (1% and 200 $\mu$g/ml, respectively) were then added. The sample was incubated to 50° C. overnight and extracted three times with buffer-saturated phenol and once with SEVAG (Sambrook et al., supra). The DNA was ethanol precipitated and resuspended in 1×TE (pH 8).

For routine virus quantitation, 1 ml of an appropriate virus dilution (prepared in unsupplemented EX-CELL 400) was added to a preconfluent monolayer of cells in a 60 mm culture dish, with intermittent agitation over a 5 hour adsorption period at 26 to 28° C. The virus inoculum was removed, and 5 ml of a 0.75% SeaPlaque agarose (FMC BioProducts, Rockland, Me.) overlay prepared with 2× EX-CELL 400 and equilibrated at 37° C. was added to the monolayer. Plaques were visualized after 5 days of incubation at 26° C. by inspection with a stereomicroscope.

The DNA prepared according to either method was then cut with a variety of restriction endonuclease enzymes, e.g., BamHI, EcoRI, HindIII, PstI and XhoI, generating the various fragments which appear on the physical map of FIG. 1. Hereafter, reference to each restriction fragment will refer to the enzyme and the applicable letter, e.g., BamHI-A through BamHI-E, EcoRI-A through EcoRI-S, etc.

EXAMPLE 2

Production of Spheroidin Polypeptide

To localize the spheroidin gene, a purified preparation of occlusion bodies (OBs) from infected caterpillars was solubilized and subjected to sodium dodecyl sulfate-polyacrylamide gel electrophoresis (SDS-PAGE) (Laemmli, J. K. [1970] *Nature* (London) 227:680–685) with a 4% acrylamide stacking gel and a 7.5% separating gel. The acrylamide used to prepare spheroidin for protein microsequencing was deionized with AG501X8 resin (Bio-Rad, Richmond, Calif.). The gels were polymerized overnight at 4° C. For sample preparation, 2×Laemmli sample buffer consisting of 125 mM Tris-HCl (pH 6.8), 4% SDS (w/v), 10% β-mercaptoethanol (v/v), and 20% glycerol (v/v) was used.

OB suspension samples were diluted 1:1 with 2×Laemmli sample buffer and boiled for 5 minutes. Several lanes of an OB protein preparation were separated electrophoretically. The spheroidin protein (113 kDa) was the predominant protein of the purified OBs. Spheroidin within SDS-polyacrylamide gels was tested for glycosylation by periodic acid-Schiff staining (Zacharius, R. M., et al. [1969] *Anal. Biochem.* 30:149–152).

Following electrophoretic separation, several lanes in the unstained gel were transferred to an Immobilon polyvinylidene difluoride (PVDF) membrane with a Bio-Rad TransBlot apparatus at 90 V for 2 hours in a buffer consisting of 10 mM morpholinepropanesulfonic acid (pH 6.0) and 20% methanol. Spheroidin was visualized on the PVDF membrane by Coomassie blue staining.

The region of the PVDF membrane containing spheroidin was excised from the membrane, and direct protein microsequencing was done with an Applied Biosystems gas-phase sequencer. Microsequencing of the intact protein was unsuccessful, presumably because the N terminus of the protein was blocked.

Cyanogen bromide cleavage was performed on samples of spheroidin eluted from the PVDF membrane to generate internal peptide fragments for sequencing. Major polypeptides of 15, 9, 8, and 6.2 kDa were produced.

EXAMPLE 3

Sequencing, Hybridizations

All DNA sequencing was done by the dideoxy chain termination method (Sanger, F., et al. [1977] *Proc. Natl. Acad. Sci. USA* 74:5463–5467) with [α-$^{35}$S]dATP and Sequenase (U.S. Biochemical, Cleveland, Ohio). Standard sequencing reactions with Sequenase were carried out in accordance with the instructions of the supplier, U.S. Biochemical.

A reliable amino acid sequence was obtained from the 9, 8, and 6.2 kDa polypeptides produced as described in Example 2. The 8 and 9 kDa polypeptides represented overlapping partial CNBr cleavage products which together yielded the longest continuous amino acid sequence: Met-Ala-(Asn or Arg)-Asp-Leu-Val-Ser-Leu-Leu-Phe-Met-(Asn or Arg)-(?)-Tyr-Val-(Asn?)-Ile-Glu-Ile-Asn-Glu-Ala-Val-(?)-(Glu?) (SEQ ID NO. 34). The amino acid sequence obtained from the 6.2 kDa fragment was Met-Lys-Ile-Thr-Ser-Ser-Thr-Glu-Val-Asp-Pro-Glu-Tyr-Val-(Thr or Ile)-Ser-(Asn?) (SEQ ID NO. 35). A partial sequence for the 15 kDa fragment was also obtained: (Asn?)-Ala-Leu-Phe-(Phe?)(Asn?)-Val-Phe (SEQ ID NO. 36). The question marks in the above sequences indicated undetermined or unconfirmed amino acids. All sequences were ultimately located within the spheroidin gene sequence.

EXAMPLE 4

Plasmid pRH512

A BglII AmEPV DNA library was prepared by digesting the genomic AmEPV DNA with BglII according to manufacturer's instructions. Plasmid pUC9 (GIBCO; Bethesda Research Labs) was BamHI-digested and phosphatase-treated. The genomic BglII cut AmEPV was shotgun cloned into the BamHI site of pUC9. *Escherichia coli* SURE (Stratagene, La Jolla, Calif.) was transformed by electroporation with a Bio-Rad Gene Pulser following the instructions provided by the manufacturer with the shotgun ligation, containing a variety of recombinant plasmids. Mini-preparations of plasmids were made by a conventional alkaline lysis procedure (Sambrook et al, supra). These plasmids were cut with EcoRI-SalI to release the insert and run on a gel. The resulting plasmid DNA was southern blotted to a nylon membrane, producing a number of clones.

Among the fragments produced from the restriction enzyme digestions of the genomic DNA was a 4.4 BglII fragment and an EcoRI-D fragment. In order to locate a desirable clone from among those produced above, the sequence derived from the 6.2 kDa CNBr fragment was used to design a degenerate oligonucleotide for use as a hybridization probe to locate the spheroidin gene in a clone. The nucleotide sequence of this probe called RM58 (SEQ ID NO. 12) was GA5GT7GA6CC7GA5TA6GT, where 5 represents A or G, 6 represents C or T, and 7 represents A, G, C, or T. The peptide sequence of the probe was: Glu-Val-Asp-Pro-Glu-Tyr-Val (SEQ ID NO. 37).

The DNA probe was radiolabeled either with [$\alpha$-$^{32}$P] dCTP by the random oligonucleotide extension method (Feinberg, A. P., et al. [1983] *Anal. Biochem.* 132:6–13) or with [$\gamma$-$^{32}$P]ATP and T4 polynucleotide kinase (Sambrook et al., supra). These same procedures were used for all other oligonucleotide probes described below. Both types of probes were purified by passage through spun columns of Sephadex G-50.

Southern transfer was done with Hybond-N (Amersham); the transferred DNA was fixed to the membrane by UV cross-linking. Southern hybridization was performed both with transferred DNA including the restriction fragments described above, as well as the BglII library of AmEPV DNA cloned into BamHI-digested plasmid pUC9 as described above. Hybridization with the oligonucleotide probe was done at 37 or 45° C. with BLOTTO (Sambrook et al., supra) and was followed by two washes at room temperature with 0.3 M NaCl-0.06 M Tris (pH 8)-2 mM EDTA for 5 minutes.

The RM58 probe (SEQ ID NO. 12) hybridized to the 4.4 kb BglII fragment and the EcoRI-D fragment of AmEPV DNA (See FIG. 1). A plasmid produced by the shotgun cloning, recombinant pRH512 (a BglII 4.56 kb fragment inserted into the BamHI site of pUC9 which contains about 1.5 kb of the 5' end of the spheroidin gene) was also identified by this hybridization with the RM58 oligonucleotide (SEQ ID NO. 12).

The 4.51 kb pRH512 BglII insert was isolated, radiolabeled as described above, and hybridized back to various AmEPV genomic digests as follows. The DNA—DNA hybridization was done at 65° C. with BLOTTO (Sambrook et al., supra) and was followed by two washes at room temperature with 0.3 M NaCl-0.06 M Tris (pH 8)-2 mM EDTA for 5 minutes, two washes for 15 minutes each at 65° C. but with 0.4% SDS added, and two washes at room temperature with 0.03 M NaCl-0.06 M Tris (pH 8)-0.2 mM EDTA. Hybridization was observed to the BamHI-A, EcoRI-D, HindIII-G and -J, PstI-A, and XhoI-B fragments of AmEPV DNA. The results of these hybridizations indicated that the 4.51 kb fragment in pRH512 was substantially identical to the 4.4 kb fragment produced by BglII digestion of genomic DNA.

The 4.51 kb BglII insert of pRH5 12 was thereafter sequenced by two procedures. One is the double-stranded plasmid sequencing method (Hattori, M., et al. [1986] *Anal. Biochem.* 152:232–238) performed with "miniprep" (Sambrook et al., supra) DNA and 1 pmol of universal, reverse, or custom-designed oligonucleotide primer in each sequencing reaction. Nested exonuclease II deletions (Henikoff, S. [1987] *Methods Enzymol.* 155:156–165) were used to sequence plasmid pRH512 according to this method. Deletions were made from the universal primer end. For making these deletions, the DNA was cut with EcoRI, filled in with $\alpha$-thiophosphate dNTPs (Putney, S. D., et al. [1981] *Proc. Natl. Acad. Sci. USA* 78:7350–7354) by use of the Klenow fragment of *E. coli* DNA polymerase, cut with SmaI, and treated with exonuclease III. Samples were removed every 30 seconds, re-ligated, and used to transform *E. coli* SURE cells by electroporation. Sequencing reactions were carried out with the universal primer.

When a primer complementary to that sequence was prepared and used to sequence back through the RM58 binding site (bases 3983 to 4002) (SEQ ID NO. 78), the generated sequence, when translated, yielded the amino acid sequence generated from microsequencing the 6.2 kDa CNBr polypeptide fragment.

A second sequencing method was performed using a combination of M12 shotgun sequencing with standard and universal and reverse M13 primers into M13 phage to permit single-stranded sequencing as follows. Plasmid pRH512 was sonicated to produce random fragments, repaired with bacteriophage T4 DNA polymerase, and these fragments were shotgun cloned into SmaI-cut M13mp19 (GIBCO). Plaque lifts were screened with a radiolabeled probe prepared from the 4.5 kb insert found in pRH512 to identify appropriate clones for shotgun single stranded sequencing (see, e.g., Sambrook et al., supra). Sequencing of the BglII insert of pRH512 isolated it to nucleotides #0 to 4505, thus extending the sequence 5' and 3' to the spheroidin gene (FIG. 2).

EXAMPLE 5

Obtaining Additional AmEPV Sequence

A DraI AmEPV DNA library was prepared by digesting genomic DNA with DraI. These DraI fragments were shotgun cloned into SmaI-digested, phosphatase-treated vector M13mp19. Preparations of M13 virus and DNA were made by standard procedures (Sambrook et al., supra). Ligation and heat shock transformation procedures were performed conventionally (Sambrook et al., supra), resulting in the shotgun cloned fragments being transformed into the bacterial strain, *E. coli* UT481 (University of Tennessee) or the SURE strain.

Standard PCR (Innis et al, supra) with 400 ng of genomic AmEPV DNA as a template was used to prepare a probe to identify a 586 bp DraI clone from nitrocellulose filter replicas (plaque lifts) (Micron Separations, Inc.) of the M13 shotgun library of DraI-cut AmEPV fragments. This was done to isolate a clone spanning a central unsequenced region of the spheroidin gene. The standard PCR primers used for this reaction were RM92 (SEQ ID NO. 15) (GCCTGGTTGGGTAACACCTC) and RM118 (SEQ ID NO. 16) (CTGCTAGATTATCTACTCCG). This sequencing revealed that there was a single HindIII site at base 931 and that the 2' end of the spheroidin open reading frame (ORF) was truncated (FIG. 2).

The technique of inverse polymerase chain reaction (PCR) (Innis, M. A., et al., [1990] *PCR protocol, a guide to methods and applications*, Academic Press, Inc. San Diego, Calif.) was used with ClaI-digested AmEPV DNA fragments which were ligated into a circle, to prepare a probe to identify clones containing a flanking sequence or to verify the absence of an intervening sequence between adjacent clones. The primers used in inverse PCR were RM82 and RM83, which were taken from the pRH512 sequence. The sequence of RM82 (SEQ ID NO. 13) was TTTCAAATTAACTGGCAACC and that of RM83 (SEQ ID NO. 14) was GGGATGGATTTTAGATTGCG.

The specific PCR reaction conditions for 34 cycles were as follows: 30 seconds at 94° C. for denaturation, 30 seconds at 37° C. for annealing, and 1.5 minutes at 72° C. for extension. Finally, the samples were incubated at 72° C. to 8.5 minutes to complete extensions. The concentration of each primer was 1 $\mu$M.

The resulting 2.2 kb inverse PCR product was digested with ClaI, and a 1.7 kb fragment was gel purified. The 1.7 kb PCR fragment was sequenced with RM83 as a primer. Additional PCR primers were made to the new sequence as it was identified. The sequencing process employed Sequenase, 5 pmol of each primer, and 10 to 50 ng of template. Prior to being sequenced, the PCR products were chloroform extracted and purified on spun columns (Sambrook et al., supra) of Sephacryl S-400. The DNA sequence was assembled and aligned, and consensus sequence was produced (Staden, R. [1982] *Nucleic Acids Res.* 10:4731–4751). Both strands were completely sequenced; the PCR product sequence was verified by conventional sequence.

The relevant ClaI sites of the 1.7 kb PCR fragment are at positions 3485 and 6165. This fragment was radiolabeled and used as a probe to locate additional clones, i.e., pRH827 (307 bp), pRH85 (1.88 kb), and pRH87 (1.88 kb) from the Bgm fragment library. Plasmids pRH85 and pRH87 were sequenced using the same nested exonuclease II deletions and sequencing procedure, as described above for pRH512. Sequencing of the inverse PCR products with custom-designed primers confirmed that plasmids pRH85 and pRH87 represented the same 1.88 kb BglII DNA insert in opposite orientations, but also revealed a missing 80 bp between pRH827 and pRH85. This 80 bp DNA fragment was identified in the DraI fragment, as extending from bases 4543 to 5128 cloned into M13.

The orientation of the spheroidin ORF on the physical map is shown in FIG. 1. It is interesting to note that the 1.7 kb inverse PCR fragment only hybridized to the AmEPV HindIII-G fragment. The amino acid sequence derived from the 8 and 9 kDa overlapping CnBr-generated polypeptides is found from nucleotide positions 4883 to 4957 (SEQ ID NO. 38). That derived from the 6.2 kDa polypeptide is found from nucleotides 3962 to 4012 (SEQ ID NO. 39), and that derived from the 15 kDa polypeptide is found from nucleotides 4628 to 4651 (SEQ ID NO. 40). Therefore, all sequences obtained from protein microsequencing were ultimately found to lie within the spheroidin ORF.

EXAMPLE 6

Spheroidin Gene Transcription

The start site for spheroidin gene transcription was determined. A primer complementary to the spheroidin gene sequence beginning 65 bp downstream of the predicted initiating methionine was prepared and used for a series of primer extensions.

A. Preparation of RNA and Primer Extension Reactions.

Six 150 mm dishes of subconfluent cells were prepared. The culture media were aspirated, and 2 ml of viral inoculum was added to each dish. The virus concentration was about 0.1 to 1 PFU per cell. The dishes were occasionally agitated during a 3 hour adsorption period. At the end of this period, the cells were rinsed with 5 ml of modified PBS. The media were replaced, and the infected cells were incubated for 72 hours at 27° C. Total RNA from the infected cells was isolated by the guanidinium thiocyanate-cesium chloride procedure (Chirgwin, J. M., et al. [1979] *Biochemistry* 18:5294–5299).

Primer extension reactions were carried out with primer RM165 (SEQ ID NO. 17), a 35-base oligonucleotide (GTTCGAAACAAGTATTTTCATCTTTT AAATAAATC) beginning and ending 100 and 65 bp downstream, respectively, of the initiating methionine codon found in the TAAATG motif. The primer was end labeled with [$\gamma$-$^{32}$P] ATP and T4 polynucleotide kinase and purified on a "spun column" (Sambrook et al., supra). For annealing, 40 $\mu$g of total infected-cell RNA and $10^6$ cpm of radiolabeled primer were coprecipitated with ethanol. The pellet was resuspended in 25 $\mu$l of hybridization buffer (80% formamide, 40 mM piperazine-N,N'-bis(2-ethanesulfonic acid) (pH 6.4), 400 mM NaCl, 1 mM EDTA (pH 8.0)], denatured at 72° C. for 15 minutes, and incubated at 30° C. for 18 hours.

For primer extension, the RNA-primer hybrids were ethanol precipitated, resuspended, and used for five individual reactions. Each reaction contained 8 $\mu$g of total infected-cell RNA, 50 mM Tris-HCl, (pH 8.3), 50 mM KCl, 10 mM dithiothreitol, 10 mM $MgCl_2$, 4 U of avian myeloblastosis virus reverse transcriptase (Life Sciences), 8 U of RNasin (Promega), 0.25 mM each deoxynucleoside triphosphate (dNTP), and the appropriate dideoxynucleoside triphosphate (ddNTP), except for a control reaction, which contained no ddNTP. The dNTP/ddNTP ratios were 4:1, 5:1, 5:1, and 2:1, for the C, T, A, and G reactions, respectively. The reactions were carried out at 42° C. for 30 minutes.

One microliter of chase buffer (4 $\mu$l of 5 mM dNTP mixture and 1 $\mu$l of 20-U/$\mu$l reverse transcriptase) was added to each reaction mixture, which was then incubated for an additional 30 minutes at 42° C. Reaction products were separated on a sequencing gel (8% acrylamide containing 7 M urea) and visualized by autoradiography. Complementarity was observed until the AAA of the upstream TAAATG motif, indicating that transcription of the gene initiates within the TAAATG element of the proposed late promoter element. Immediately upstream is a 5' tract of noncoded poly(A) on the transcripts. The average length of the poly(A) is greater than 6 bp.

EXAMPLE 7

Analysis of Spheroidin Sequence

The spheroidin ORF (G5R) (SEQ ID NO. 21) (was initially identified by sequencing back through the RM58 oligonucleotide primer binding region (SEQ ID NO. 78) as described above. Examination of the AmEPV spheroidin gene sequence (ORF G5R) revealed a potential ORF of 3.0 kb capable of encoding 1,003 amino acids or a protein of about 115 kDa (SEQ ID NO. 6). The ORF consists of 29% G+C, in contrast to the 18.5% reported for the entire AmEPV genome (Langridge, W. H. R., R. F. Bozarth, D. W. Roberts [1977] Virology 76:616–620). Inspection of the 92 bases upstream of the initiating ATG revealed only 7 G or C residues. Also detected was the presence of known vertebrate poxvirus regulatory sequences within the 92 bp 5' of the spheroidin ORF. Included are three TTTT TNT early gene termination signals and TAAATG, which presumably represents a late transcription start signal used to initiate transcription and translation of the spheroidin gene. Several adjacent translation termination codons are also present within the 92 bp upstream of the spheroidin ORF.

Analysis of the sequence upstream of the spheroidin gene revealed four additional potential ORFs, G1L (SEQ ID NO. 25), G2R (SEQ ID NO. 23), G3L (SEQ ID NO. 26), and G4R (SEQ ID NO. 24), discussed above. The putative amino acid sequences of these ORFs are reported in FIG. 2 (SEQ ID NO. 2, 3, 4 and 5, respectively). No significant homologies were found for the small potential polypeptides encoded by ORF G2R (SEQ ID NO. 23) or G3L (SEQ ID NO. 26). ORF G1L (SEQ ID NO. 25), however, exhibited a significant degree of homology to ORF 17 found within the HindIII-I fragment of vaccinia virus, whose function is unknown. ORF G4R (SEQ ID NO. 24) showed homology to ORF HM3 of capripoxvirus. In vaccinia virus, the ORF HM3 homolog was found very near the site of an incomplete ATI gene. The partial G6L ORF (SEQ ID NO. 27) to the right of the spheroidin gene exhibited good homology to vaccinia virus NTPase I. Much better homology (78.4% identity over 162 amino acids) was found between the partial G6L ORF (SEQ ID NO. 27) and NPH I of CbEPV (Yuen, L., et al. [1991] *Virol.* 182:403–406).

EXAMPLE 8

Isolation and Sequencing of the AmEPV EcoRI-Q Fragment Containing the tk Gene Sequencing of the EcoRI-Q fragment of genomic AmEPV of Example 1 was performed using techniques described above for spheroidin. The sequencing showed 1511 bp containing two complete and one partial ORF. Analysis of the DNA sequence of ORF Q2 (SEQ ID NO. 28) indicates the sites where the identifying degenerate oligonucleotides (RM03 SEQ ID NO. 18 and RM04 SEQ ID NO. 19) might hybridize. Two oligonucleotides, RM03 and RM04, based on different but strongly conserved regions of the tk genes of several poxviruses and vertebrates (Upton, C., et al. [1986] *J. Virol.* 60:920–927; Boyle, D. B., et al. [1987] *Virology* 156:355–365) were prepared by the methods referred to above. RM03 was the 32-fold degenerate oligonucleotide (SEQ ID NO. 18) GA(T/C)GA(G/A)GG(G/A) GG(G/A)CA(G/A)TT(C/T)TT corresponding to the amino acid residues in the vaccinia tk protein from the aspartic acid at position 82 to the phenylalanine at position 87. RM04 (SEQ ID NO. 19) was (GGNCCCATGTT(C/T)TCNGG with 32-fold degeneracy and corresponded to the region from the glycine at position 11 to the glycine at position 16 in vaccinia. These probes were radiolabeled as described above for the RH58 probe.

The AmEPV thymidine kinase (tk) gene was identified by hybridization with the degenerate oligonucleotide probes RM03 and RM04 to a Southern blot of the EcoRI-digested EPV DNA. The EcoRI band of interest (EcoRI-Q) was isolated, purified, and ligated into a pUC18 vector (GIBCO), previously digested with EcoRI and treated with calf intestinal alkaline phosphatase. Recombinant clones were identified by the size of the insert and by hybridization to the radioactive labeled oligonucleotide probes.

One such clone was called pMEGtk-1. The recombinant clones containing the EcoRI-Q fragment oriented in both directions relative to the pUC1 8 vector sequences were used for sequencing. Sequential nested deletions were generated by the method of Henikoff, cited above, as described for pRHS 12. These clones were used for sequencing the entire EcoRI-Q fragment.

Subsequently, these oligonucleotides and another, RM129 is a non-degenerate oligonucleotide GGTGCAAAATCT-GATATTTC (SEQ ID NO. 20) prepared from the ORF Q1, were employed as sequencing primers to confirm their positioning as indicated in ORF Q2 (SEQ ID NO. 28). ORF Q2 potentially encodes for a protein of 182 amino acids (21.2 kDa) (SEQ ID NO. 10). ORF Q3 potentially encodes a polypeptide of at least 68 amino acids but is incomplete (SEQ ID NO. 11) and is transcribed in the opposite direction from ORF Q2. ORF Q1 (SEQ ID NO. 31) potentially encodes a small peptide of 66 amino acids (7.75 kDa) (SEQ ID NO. 9).

Further analysis of the EcoRI-Q fragment reveals several other points. First, the A+T content is very high (80%). For ORF Q2, the 100 nucleotides upstream of the start codon for translation are 90% A+T. Some potential poxvirus transcription signals were found between ORFs Q1 and Q2. The five bases immediately preceding the start codon for ORF Q1 are TAAATG which comprise a consensus late poxvirus promoter. A potential poxvirus early transcription termination signal sequence (TTTTTAT) is located 2 nt past the translation stop codon of Q2.

The deduced amino acid sequence for the tk encoded by the ORF Q2 of the EcoRI-Q fragment can be compared to the tk genes for the poxviruses swine pox (Schnitzlein, W. M., et al. [1991] *Virol.* 181:727–732; Feller, J. A., et al. [1991] *Virol.* 183:578–585); fowlpox (Boyle et al., supra; Binns, M. M., et al. [1988] *J. Gen. Virol.* 69:1275–1283); vaccinia (Weir, J. P.,et al. [1983] *J. Virol.* 46:530–537; Hruby, D. E., et al. [1983] *Proc. Natl. Acad. Sci. USA* 80:3411–3415); variola and monkeypox (Esposito, J. J., et al. [1984] *Virol.* 135:561–567); capripoxvirus (Gershon, P. D., et al. [1989] *J. Gen. Virol.* 70:525–533); Shope fibroma virus (Upton et al., supra); the cellular thymidine kinases of humans (Bradshaw, H. D., et al. [1984] *Mol. Cell. Biol.* 4:2316–2320; Flemington, E., et al. [1987] *Gene* 52:267–277); the tk of mouse (Lin, P. F., et al. [1985] *Mol Cell. Biol.* 5:3149–3156); the tk of chicken (Kwoh, T. J., et al. [1984] *Nucl. Acids Res.* 12:3959–3971); ASF (Blasco, R., et al. [1990] *Virol.* 178:301–304; Martin Hernandez, A. M., et al. [1991] *J. Virol.* 65:1046–1052).

EXAMPLE 9

Expression of the AmEPV tk Gene in a Vaccinia Virus

The AmEPV tk gene was tested functionally by cloning the gene into a vaccinia virus strain $tk^-$ mutant, as follows.

The EcoRI-Q fragment of AmEPV, described above, was inserted in both possible orientations into shuttle plasmid pHGN3.1 (Bloom, D. D., et al. [1991] *J. Virol.* 65:1530–1542) which had been isolated from bacterial cells by the alkaline lysis method. This EcoRI-Q DNA fragment contains the AmEPV tk open reading frame (ORF) (SEQ ID NO. 28). The cloning was performed conventionally. The resulting plasmid was designated pHGN3.1/EcoRI-Q.

The plasmid was transfected by Lipofectin (GIBCO) as described specifically below into mammalian cells infected with vaccinia virus. The cells were either rat $tk^-$, human 143 $tk^{31}$ , or CV-1 cell lines onto which the vaccinia virus VSC8 was propagated. These cells were maintained in Eagle's Minimal Essential Medium with Earle's salts (Massung et al. [1991] *Virol.* 180:347–354, incorporated by reference herein).

The VSC8 vaccinia strain (Dr. Bernard Moss) contains the β-galactosidase gene driven by the vaccinia $P_{11}$ promoter ($P_{11}$-Lac Z cassette) inserted into the viral tk gene. While VSC8 contains an inactive tk gene due to the insertion of the β-galactosidase, portions of the vaccinia tk sequence remain. VSC8 is thus $tk^-$ and, upon staining with X-Gal (5-bromo-4-chloro-3-indoyl-β-D-galactopyranoside), will form blue plaques (β-galactosidase positive).

Cells were grown to 80% confluence ($4\times10^6$ per 60 mm dish). Lipofectin solution (20 μg of Lipofectin in 50 μl of $dH_2O$) was added to 10 μg plasmid DNA (pHGN3.1/AmEPV EcoRI-Q) in 50 μl of $dH_2O$ and incubated for 15 minutes at room temperature. After a 2 hour period of viral adsorption (m.o.i. of 2, 37° C.), the monolayers were washed three times with serum-free OptiMEM. Three milliliters of serum-free OptiMEM was then added to each 60 mm dish. The Lipofectin/DNA mixture was slowly added dropwise with gentle swirling and incubated an additional 12 to 18 hours at 37° C. Fetal bovine serum was then added (10% final) and the infected cells were harvested at 48 hours postinfection.

Recombinant viruses, containing the EcoRI-Q fragment inserted into the hemagglutinin (HA) gene of vaccinia, were identified by hybridization of AmEPV EcoRI-Q fragments, radioactively labeled by procedures described above, to replicas of nitrocellulose "lifts" of virus plaques from the infected monolayer. Potential recombinants were isolated from replica filters and plaque-purified several times before testing.

The tk of AmEPV exhibits some degree of homology with the tk of vaccinia. To confirm that insertion of the AmEPV tk gene was within the HA gene of vaccinia rather than within residual tk sequences remaining in VSC8, the recombinants were examined by a series of Southern hybridizations to HindIII digests of the various viruses. When DNA from wild-type virus was hybridized to a vaccinia virus tk probe, hybridization was observed exclusively within the ≈5 kb HindIII-J fragment of AmEPV.

When either VSC8 or either of the AmEPV tk containing recombinants was examined using the vaccinia tk probe, hybridization occurred instead to an ≈8 kb fragment consistent with insertion of the 3.1 kb β-galactosidase cassette into the TK gene of the HindIII-J fragment. Hybridization of the HindIII digests of the same three viruses to radiolabeled AmEPV EcoRI-Q DNA resulted in hybridization to a large-molecular-weight DNA fragment in the recombinant containing the AmEPV TK gene, which we have shown corresponds to the HindIII-A fragment. These results suggest that insertion of the AmEPV TK gene into vaccinia occurred within the HA gene contained within the large (>23 kb) HindIII-A fragment of the virus as expected. Identical results were observed for VSC8::TKII. It is also interesting to note the lack of hybridization of the vaccinia virus (VV) and AmEPV TK probes to the heterologous poxvirus TK genes under these conditions, even though there is significant sequence homology between the vaccinia and the AmEPV TK genes.

Plaque-purified vaccinia recombinants were tested for growth on human 143 $TK^-$ cells in the presence of methotrexate. Under these conditions, only $TK^+$ virus will grow and produce plaques. Both recombinants (VSC8::AmEPV TKI and VSC8::AmEPV TKII) representing the two orientations of the AmEPV EcoRI-Q fragment gave plaques in the presence of methotrexate. All plaques from both recombinant viruses which grew in the presence of methotrexate also stained blue upon staining with X-Gal, suggesting that the $TK^+$ phenotype of these recombinants is most likely due to a functional TK gene contained within the AmEPV EcoRI-Q fragment. Since functionality is independent of the orientation of the AmEPV EcoRI-Q fragment, it is plausible that an AmEPV TK gene promoter contained within the EcoRI-Q fragment may function in vaccinia.

EXAMPLE 7

Orientation of the TK Gene Within the AmEPV Genome

In order to determine the orientation of the Q1, Q2, Q3 ORFs (SEQ ID Nos.31, 28, and 32, respectively) within the EcoRI-Q fragment relative to the genome, a DNA primer-mediated extension reaction was performed. The EcoRI-Q fragment is contained within the PstI-F fragment. An oligonucleotide identical in sequence to bases 182–163 (RM129, SEQ ID NO. 20) was prepared and hybridized to a heat-denatured PstI digest of genomic AmEPV DNA. The partial hybrid was then extended with the Klenow fragment of *E. coli* DNA polymerase in the presence of radiolabeled substrates. Extension will terminate at the end of the PstI-F fragment.

The radiolabeled product was then hybridized to an EcoRI digest of AmEPV DNA. If orientation of the gene is such that the tk ORF reads toward the end of the genome, hybridization would be expected to the EcoRI-E fragment; whereas if the gene is read toward the center of the genome, hybridization would be expected to the EcoRI-I fragment.

The results indicate hybridization not only to the EcoRI-E fragment, but also to the EcoRI-A fragment. These results infer that the orientation of the tk gene is with reading toward the left end of the genome. Hybridization of the run-off extension product also to the EcoRI-A fragment is consistent with the presence of an inverted terminal repetition, common in poxviruses, with identical sequences residing in both the EcoRI-A and the EcoRI-E fragments.

The optimal growth temperature for AmEPV in the laboratory is 28° C., whereas that of the vertebrate poxviruses is 37° C. As described herein, when the AmEPV DNA fragment containing the entire tk gene was cloned into the $tk^-$ strain of vaccinia virus, the recombinant virus was capable of growing at 37° C. in the presence of methotrexate (Sigma), indicative of a $tk^+$ phenotype. This example demonstrates that the Entomopoxvirus tk gene can be successfully transferred into mammalian expression systems, and that AmEPV tk is functionally active over a considerable temperature range.

EXAMPLE 10

Isolation and Sequencing of CbEPV and CfEPV Spheroidin Genes

Viruses and cell culture. Choristoneura EPVs, CbEPV and CfEPV, occlusion bodies (OBs) were obtained from Dr. Basil M. Arif, Forest Pest Management Institute, Sault Ste. Marie, Ontario, Canada, and can be obtained from other sources as well. The AmEPV OBs were the same as those used previously (Hall and Moyer, 1991). The gypsy moth cell line, IPLB-LD-652, used for AmEPV replication was maintained in EX-CELL 401 (JRH Biosciences, Lenexa, Kans.) supplemented with 10% fetal bovine serum. Wild type cowpox virus, Brighton red strain, was produced in CV-1 cells cultured in Eagle's MEM with Earle's salts.

SDS-PAGE. occlusion body solubilization, and total cell protein preparation. Sodium dodecyl sulfate-polyacrylamide gel electrophoresis (SDS-PAGE) of proteins was with a 4% acrylamide stacking gel and a 7.5% separating gel. For sample preparation, 2× Laemmli sample buffer consisting of 125 mM Tris-HCl (pH 6.8), 4% SDS (wt/vol), 10% β-mercaptoethanol (vol/vol), 20% glycerol (vol/vol), and 0.05% bromphenol blue (wt/vol) was used. Quantitation of OBs was achieved by counting a diluted suspension in a hemocytometer. The OB suspension (varying from $8\times10^6$ to $1\times10^8$ OBs/ml) usually prepared in 1×TE (10 mM Tris-HCl, 1 mM EDTA, pH 8.0), was diluted 1:1 with the 2× Laemmli sample buffer and immediately boiled for 5 or 10 min. For studies designed to assay for spheroidin degradation, the OBs plus sample buffer were left at room temperature for various time periods before boiling. After electrophoretic separation, the proteins were visualized by Coomassie blue staining.

The preparation of total uninfected or infected cell protein for SDS-PAGE utilized a 2× lysis buffer consisting of 160 mM Tris-HCl (pH 9), 4% SDS (wt/vol), 4% β-mercaptoethanol (vol/vol), 10% glycerol (vol/vol), 5 M urea, 20 mM EDTA (pH 8), and 0.01% bromphenol blue (wt/vol). Cells were scraped from a 150 mm diameter culture dish using a rubber policeman and centrifuged at 1000×g for 5 min at 4° C. Cells were washed in appropriate cold phosphate buffered saline (PBS) and recentrifuged. Insect cells were harvested in Hank's PBS which contained 15 g glucose per liter. The cell pellets were resuspended in a final volume of 500 μl of PBS which contained 5 μl each per ml of PMSF (phenylmethyl sulfonyl fluoride, 0.1 M stock in 95% ethanol) and aprotinin (0.3 mg/ml stock). The cells were probe sonicated on ice for 15 sec., five hundred microliters of 2×lysis buffer was added, and the preparation sonicated as before. Samples were stored at −70° C. and boiled before loading on an SDS-PAGE gel.

Preparation of EPV DNAs. CfEPV DNA was obtained from Dr. Basil M. Arif, Forest Pest Management Institute, Sault Ste. Marie, Ontario, Canada. CbEPV DNA used in the polymerase chain reaction (PCR) studies was prepared directly from occlusion bodies by the agarose in situ method (Hall and Hink, 1990) and extracted by "freeze-squeeze" (Sambrook et al., 1989). AmEPV DNA was prepared from infected LD-652 cell culture by concentrating extracellular virus which was then treated with DNase I and RNase A prior to dissolution of the occlusion bodies by SDS and proteinase K digestion (Gruidl et al., 1992).

PCR Primers and Reactions. PCR, product purification, and dideoxy sequencing were done as described previously (Hall and Moyer, 1991) except that the specific reaction conditions for 34 cycles were 1 min at 94° C. for denaturation, 1 min at 37° C. for annealing, and 2 min at 72° C. for extension. Finally, samples were incubated at 72° C. for 9 min to complete extensions. Typically, 50 to 100 ng of template DNA was used in the PCRs. Custom oligonucleotide primers RM82, RM83, RM92 and RM118 (SEQ ID NOs. 13–16) were described previously (Hall and Moyer, 1991). Sequences of these and other AmEPV spheroidin specific PCR primers (5' to 3', base pair numbers from Hall and Moyer, 1991) are summarized in Table 2.

TABLE 2

PCR reactions used in checking *Choristoneura* EPV DNA for a homolog of the AmEPV spheroidin gene

| AmEPV spheroidin specific primer pair[1] | Expected Product Size (bp) | Appropriate Size Product Observed CbEPV | CfEPV |
|---|---|---|---|
| 12 - 9 | 314 | – | – |
| 12 - 8 | 599 | + | + |
| 12 - 6 | 828 | – | – |
| 12 - 3 | 1047 | – | – |
| 12 - 4 | 1184 | – | – |
| 1 - 4 | 290 | + | + |
| 12 -11 | 1444 | – | + |
| 1 - 11 | 549 | + | + |
| 2 - 11 | 307 | + | + |
| 12 - 15 | 1542 | – | – |
| 1 - 15 | 648 | + | + |
| 2 - 15 | 378 | + | + |
| 12 - 13 | 1944 | – | – |
| 1 - 13 | 1050 | + | + |
| 2 - 13 | 807 | + | + |
| 5 - 13 | 632 | – | + |
| 7 - 13 | 595 | + | + |
| 14 - 13 | 426 | + | + |
| 10 - 13 | 259 | – | + |

Figure 5:
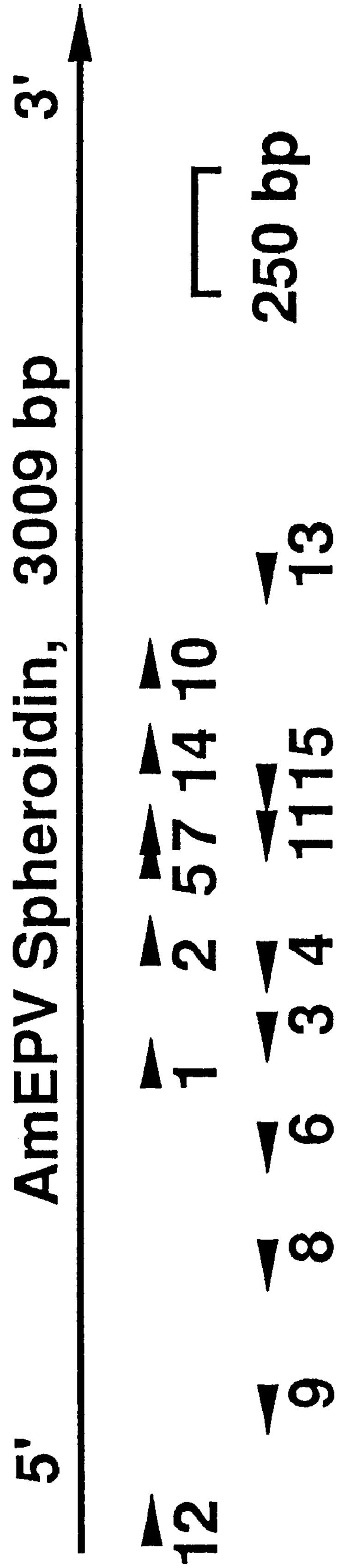
FIG. 5 shows the location of the AmEPV spheroidin specific oligonucleotide primers used in PCR to identify an AmEPV spheroidin-like gene in Choristoneura EPV DNAs. The arrowheads over the numbers in the diagram represent oligonucleotide primers. The arrowhead base shows the approximate starting point of the primer, and the 5' to 3' direction is shown by the direction of the arrowhead. Primers from the upper line were paired with various primers from the lower line as shown in Table 2 for PCR reactions. The sequences of the primers are shown in Table 2.

[1]Primer numbers correspond to those in FIG. 5 and the sequences (5' to 3') are shown below:
1. RM58 - GAAGTNGATCCNGAATATGT SEQ ID NO. 52
2. RM75 - GAAAATAAAATTATATTGGA SEQ ID NO. 53
3. RM76 - AGACAATTCCAGATATAATG SEQ ID NO. 54
4. RM78 - CCGCATCTATATTCTGCTTC SEQ ID NO. 55
5. RM79 - GTTTAAAACCTAAAGTACCC SEQ ID NO. 56
6. RM82 - TTTCAAATTAACTGGCAACC SEQ ID NO. 13
7. RM83 - GGGATGGATTTTAGATTGCG SEQ ID NO. 14
8. RM87 - GTTGCATCTGTAGTTACATC SEQ ID NO. 57
9. RM91 - TCTAGCAATAATCGACTTAC SEQ ID NO. 58
10. RM92 - GCCTGGTTGGGTAACAACTC SEQ ID NO. 15
11. RM93 - CATTTCTATTAAGCCTAACG SEQ ID NO. 59
12. RM95 - GTACCTTTAGCAACCAAAAC SEQ ID NO. 60
13. RM118 - CTGCTAGATTATCTACTCCG SEQ ID NO. 16
14. RM169 - AATTGCACATTATCATTGGG SEQ ID NO. 61
15. RM170 - ATTACCCAATGATAATGTGC SEQ ID NO. 62

Primer RM206 (AGATGATGATTAAAGTGTGG) (SEQ ID NO. 50) was from bases 2379 through 2398 and RM212 (GATAATGATACTCCGGTTGC) (SEQ ID NO. 51) from bases 2077 through 2096 of the CbEPV NPH I sequence (Yuen et al., 1991).

Cloning and double strand plasmid sequencing. BglII clones in both orientations (1.06 kb and 1.78 kb) covering the unsequenced 5' end of the AmEPV NPH I gene were selected from an AmEPV BglII fragment library (Hall and Moyer, 1991) by hybridization with an AmEPV 13 kb HindIII fragment probe. Plasmids were cloned in the *Escherichia coli* SURE strain (Stratagene, La Jolla, Calif.). Plasmids were sequenced by use of exonuclease III deletions and dideoxy sequencing as described (Hall and Moyer, 1991). Both strands were completely sequenced.

Radiolabeled probes, Southern blotting, and hybridization. Random oligolabeling of DNA for probes, Southern transfer and hybridization (at 65° C. with BLOTTO) were as described previously (Hall and Moyer, 1991).

Protein microsequencing. Lys-c endoprotease digestion of the 115 kDa protein of CbEPV OBs purified and recovered from SDS-PAGE gels was used to generate internal peptide fragments for sequencing on a gas phase sequencer.

Antibody preparation and immunoblotting. A preparation of total occlusion body antigens was prepared by solubilizing purified AmEPV occlusion bodies purified from infected cell cultures. Rabbits were then intradermally injected with 100–200 μg of antigen per rabbit in Freund's complete adjuvant. One month later, the rabbits were boosted with about 500 μg each of the same antigen in incomplete adjuvant. After an additional 3 weeks, the rabbits were boosted with 200 μg of antigen in incomplete adjuvant.

Eleven days later, the immune serum was collected. This serum is referred to as occlusion body antisera. Monospecific spheroidin antibodies were prepared from this serum based on immunoaffinity of individual antibodies for purified spheroidin (Harlow and Lane, 1988). Samples of the sera were adsorbed to a nitrocellulose blot prepared from a preparative SDS-PAGE gel of solubilized AmEPV occlusion bodies. The section of the blot containing the 115 kDa AmEPV spheroidin and bound antibodies was then excised. The monospecific AmEPV spheroidin antibodies were eluted using 100 mM glycine, pH 2.5. After neutralization and dilution, the monospecific spheroidin antibodies were used to probe Western blots.

For immunoblotting, duplicate samples run on SDS-PAGE gels were prepared. One-half of the gel was stained with Coomassie blue, and the other half (containing prestained molecular mass markers) was transferred to nitrocellulose membrane in Tris-glycine buffer (Harlow and Lane, 1988) using the BioRad Trans Blot at 250 mA for 3 hours. The blot was blocked for 2 hr using BLOTTO (0.5% nonfat dry milk in TBS: 0.01 M Tris, pH8, 0.15 M NaCl). Dilutions of the antibody were prepared in BLOTTO and adsorbed to the blot overnight. The blot was washed 3 times in TBS at room temperature, and the secondary antibody (goat anti-rabbit conjugated to alkaline phosphatase) at a 1:1000 dilution was adsorbed to the blot for 1½ hr. The blot was washed with TBS as previously. Secondary antibody reactions and color development was as described (Harlow and Lane, 1988).

SDS-PAGE of solubilized occlusion bodies. When purified occlusion bodies of CbEPV, CfEPV and AmEPV are solubilized in Laemmli sample buffer, boiled immediately, and analyzed on SDS-PAGE gels, Coomassie blue staining shows the major protein to be about 115 kDa in each case. The Choristoneura EPVs show a second 47 kDa protein in lesser amounts. Other minor proteins were also observed.

The purported CbEPV spheroidin gene has a coding capacity of 47 kDa (Yuen et al., 1990) despite the fact that the observed size of the corresponding spheroidin appears to be 115 kDa, which is similar to that observed for the AmEPV spheroidin. This discrepancy has been explained by suggesting that the CbEPV spheroidin exists as relatively unstable dimers, which dissociate under a variety of conditions to monomers of 47 kDa (Yuen et al., 1990). The AmEPV spheroidin of 115 kDa, however, shows no such propensity for dissociation.

Prior to dissolution, occlusion bodies are stable and routinely stored at 4° C. in buffer. The only discernible difference in methods of occlusion body solubilization and preparation is the incubation time in SDS buffer before boiling. The relative instability of the various spheroidins was evaluated by incubating the occlusion bodies of all three EPVs at room temperature for up to two hours in SDS solubilizing buffer before boiling the samples. While some degradation of the 115 kDa protein was observed for the CfEPV OB preparation, little if any degradation of the CbEPV or AmEPV preparations was observed. The CfEPV 115 kDa protein was degraded to a variety of smaller proteins but not in a fashion suggesting a relationship to the 47 kDa protein. Whether the OB suspension was in 1×TE (10 mM Tris, 1 mM EDTA, pH8) or in deionized water prior to dissolution has no effect on the subsequent degradation CfEPV occlusion bodies.

Discovery of an AmEPV spheroidin gene homolog in CbEPV and CfEPV. Selected oligonucleotide primers derived from within various regions of the AmEPV spheroidin gene were selected as appropriate primer pairs for PCR to look for the spheroidin gene in CbEPV and CfEPV. The relative positions of these primers within the spheroidin gene are shown in FIG. 5. Table 2 lists the specific primer pairs and sequences, the expected size of the PCR products based on the AmEPV spheroidin sequences, and the results when these primers were used in conjunction with CbEPV or CfEPV templates. From Table 2, for CbEPV template 10 out 19 primer pairs resulted in an appropriate size product expected if the two genes were similar. For CfEPV this was 13 out of 19 primer pairs. We chose one of the products (I kb) generated from CfEPV DNA by primer pair 1–13 (in Table 2) for further analyses.

This PCR product was radiolabeled and used as a probe for a blot containing restriction fragments of both CfEPV and AmEPV DNAs. All hybridizations to CfEPV showed predominant, specific hybridization signals. The CfEPV derived probe also shows appropriate, discrete hybridizations to AmEPV DNA; i.e., a 13 kb HindIII fragment, a 20 kb EcoRI fragment, a 4.5 kb BglII fragment, and a 4.5 kb BstBI fragment. This pattern of hybridization to AmEPV is that expected for hybridization to the AmEPV spheroidin gene.

Partial sequence of a spheroidin-like gene in CbEPV or CfEPV. Further indications of the existence for an AmEPV spheroidin gene homolog in the genome Choristoneura EPVs come from PCR product sequencing of the 1 kb Choristoneura PCR products (primer pair 1–13; Table 2). The resulting sequences derived from the CbEPV (SEQ ID NO. 43) or CfEPV DNA (SEQ ID NO. 45) with a comparison to the AmEPV sequence (SEQ ID NO. 76) is shown in FIG. 6A. When the deduced amino acid sequence of this region is compared (FIG. 6B; SEQ ID Nos. 44, 46, and 77), a very high degree of homology is found between all three viruses.

The spheroidin-like gene in CbEPV and CfEPV is expressed. Samples of the CbEPV ≈115 kDa protein were isolated from SDS-polyacrylamide gels, and treated with lys-c endoprotease to generate peptides for microsequencing. Three of the resulting peptides were analyzed, and the amino acid sequence was compared to the spheroidin of AmEPV. The CbEPV sequences obtained were homologous to three corresponding regions of the AmEPV spheroidin (FIG. 6C; SEQ ID NOs. 47–49). These results demonstrate that the Choristoneura viruses not only contain a spheroidin-like gene, but that gene is expressed to yield a polypeptide within occlusion bodies of similar size and sequence to the previously-identified spheroidin protein of AmEPV.

We have also addressed the question of whether the AmEPV spheroidin homolog in CbEPV and CfEPV is expressed by a Western blot analysis of the proteins of CbEPV and CfEPV using antibody derived against either AmEPV occlusion bodies or monospecific sera against AmEPV spheroidin. Sera directed against purified AmEPV occlusion bodies recognize proteins of ≈115 kDa in both CbEPV and AmEPV. Stronger signals are observed in the AmEPV samples as expected. An AmEPV protein of 38 kDa is also recognized in the samples. Weak binding is also observed to the abundantly expressed protein of the vertebrate cowpox virus which was used as a control. When immunoaffinity purified, monospecific AmEPV spheroidin sera is used, the 115 kDa protein of CbEPV also cross-reacts. Similar results were obtained with CfEPV. These results also support the conclusion that the two Choristoneura viruses and AmEPV encode a very similar major occlusion body protein of 115 kDa which in AmEPV corresponds to the spheroidin gene.

Co-linearity of AmEPV, CbEPV, and CfEPV maps in the spheroidin region. We have shown that the gene adjacent to the 3' terminus of the AmEPV spheroidin gene is NPH I (NTPase I) in polarity opposite to that of the spheroidin gene. A NPH I gene from CbEPV has been sequenced (Yuen et al., 1991).

The 5' end sequence of the NPH I (or NTPase I) gene of AmEPV (SEQ ID NO. 41) is presented in FIG. 7. The 3' end sequence of this gene is provided in FIG. 1 (SEQ ID NO. 27) and the nucleotide numbering system depicted in FIG. 7 results from appending the 5' end of the sequence to the sequence provided in FIG. 1.

When the complete coding sequence (SEQ ID NO. 74) and deduced amino acid (SEQ ID NO. 75) sequence of the AmEPV NPH I gene was compared to the already published CbEPV NPH I gene (Yuen et al., 1991), the two genes show 89% amino acid and 86% nucleotide identity. Both proteins have a deduced 648 amino acids, with the major difference being that AmEPV has deleted amino acid number 127 and has one extra amino acid at the very end of the sequence. Both genes show the typical poxvirus late gene promoter sequence motif, TAAATG, at the beginning of the open reading frame as well as the A+T rich sequence upstream of the gene. Of the 30 bases preceding the starting ATG, only a single G differentiates the AmEPV and CbEPV. The intergenic region between the spheroidin and NPH I genes begins to diverge immediately following the NPH I open reading frame (ORF) at the downstream 3' end.

Figure 8:
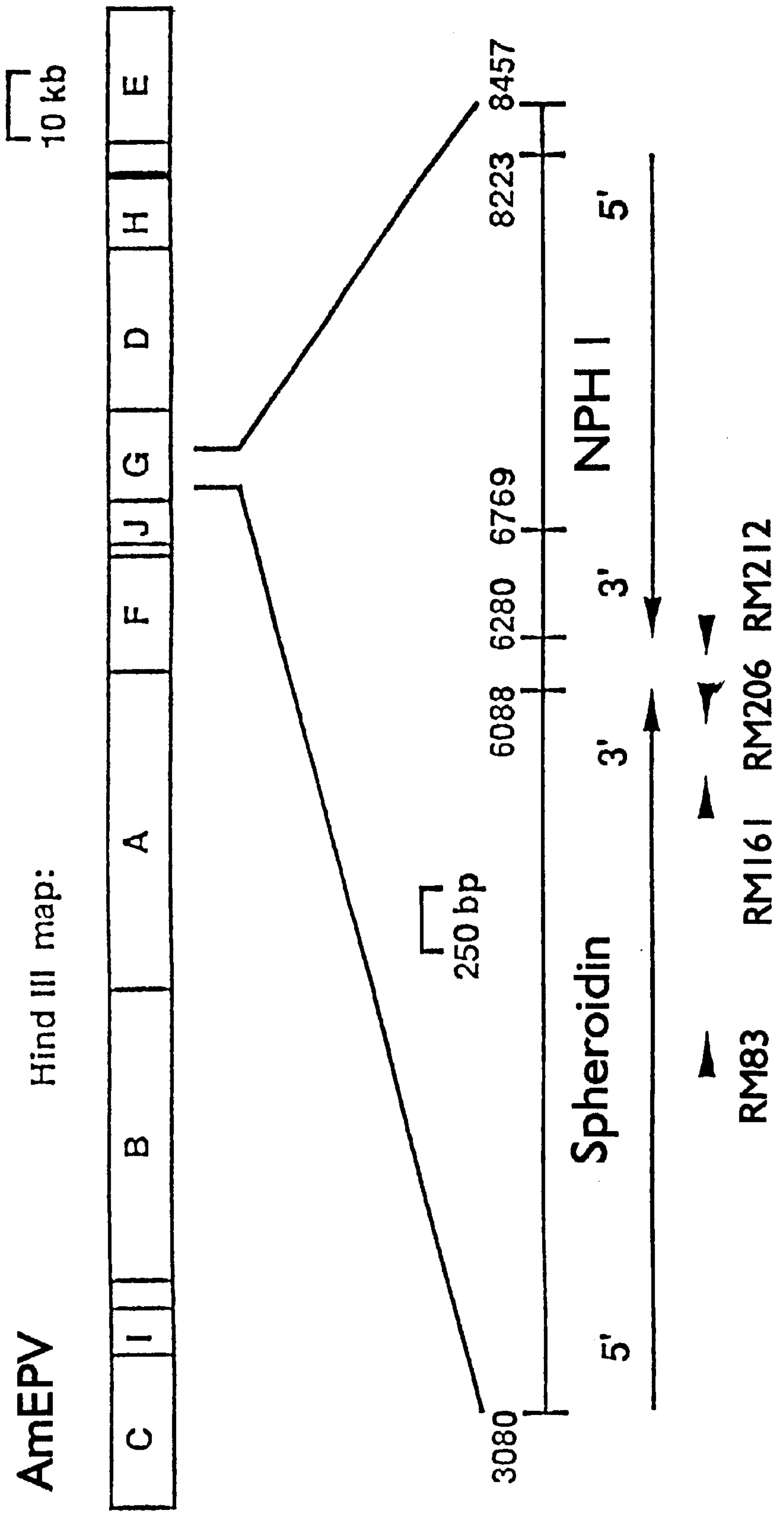
FIG. 8 shows the spheroidin and NPH I gene orientations in AmEPV, and the locations of primers used in PCR reactions. The arrowheads over the numbers in the figure represent oligonucleotide primers. The arrowhead base shows the approximate starting point of the oligo and 5' to 3' is shown by the direction of the arrowhead. RM83 (SEQ ID NO. 14) and RM161 are AmEPV spheroidin specific primers. Primer RM212 (SEQ ID NO. 51) is from the 3' end of the CbEPV NPH I gene and RM206 (SEQ ID NO. 50) is just downstream of the CbEPV NPH I gene but within the published CbEPV sequence (Yuen et al. [1991], supra).

The proximity of the spheroidin and NPH I genes in both Choristoneura viruses was tested by performing a series of PCR reactions using the PCR primers shown in FIG. 8 which were designed based on the AmEPV gene arrangement and were used with either CfEPV or CbEPV. Primers RM206 (SEQ ID NO. 50) and RM212 (SEQ ID NO. 51) are described above in this example, RM83 (SEQ ID NO. 14) and RM161 (SEQ ID NO. 79) in Table 2. Primer pair RM161-RM212 failed to give a PCR product with CbEPV DNA indicating sequence differences between CbEPV and CfEPV in the RM161 primer binding region. However, the other three reactions generated PCR products ranging in size from ≈1–2.5 kb, indicating that the NPH I and spheroidin genes are adjacent and arranged similarly to AmEPV. Based on the PCR products, the intergenic distance between the Choristoneura spheroidin and NPH I genes appears to be at least about 450 bp longer than the same region in AmEPV. The increased size of this intergenic region is large enough to perhaps allow for a small ORF to be present between the two genes in the Choristoneura viruses. However, PCR product sequencing of the RM83-RM212 and the RM161-RM206 PCR products using RM206 as the primer failed to show any ORF of significant size.

Our results suggest that the published Choristoneura EPV gene identified by Yuen et al. (1990) as the spheroidin gene, is incorrect. Our evidence shows instead that the spheroidin gene of Choristoneura EPVs is virtually identical to that of AmEPV (FIG. 6), i.e., encodes a 115 kDa protein and is expressed. Hence this protein is highly conserved amongst all three viruses.

The AmEPV spheroidin gene found in the Choristoneura EPV genomes and the NPH I genes were found to be immediately adjacent to each other and in opposite polarity in all three viruses. Although the intergenic distance between the two genes is somewhat different between the two Choristoneura viruses and AmEPV, it would appear that the genes in this region of the viral DNA are co-linear.

We have shown that the linear conserved core of genes found in vertebrate poxviruses is not maintained in AmEPV. Based on the data presented here, it appears that the entomopoxviruses have evolved and maintained a common core of co-linear genes, different from their vertebrate counterparts.

EXAMPLE 12

Production of a Recombinant AmEPV which Expresses an Heterologous Gene Inserted into the AmEPV Thymidine Kinase Gene An heterologous gene was inserted into the AmEPV Tk gene via homologous recombination, and recombinant virus expressing the heterologous gene was obtained as follows. Unless otherwise noted, for plaque assays, C11-3 ($Tk^-$ cells produced as described below), were used in a 50:50 mixture of Excell:TC100 medium. The overlay used for detection of LacZ expression used only TC100 medium.

A plasmid, pTk::ATI-LacZ was prepared by using PCR and primers for the Tk gene with EcoRI ends. The PCR reaction was run on the full length clone of the EcoRI-Q fragment (pMEGtk-1, ATCC No 68532) described in Example 8, using primers RM282, SEQ ID NO. 63, and RM283, SEQ ID NO. 64, in about 100 $\mu$L 10 mM Tris, pH 7.76, 0.4 mM EDTA. This resulted in the amplification of a fragment from base 253 to base 780 (about 527 base pairs) of the GenBank AAVTHYKIN locus, with internal EcoRI sites at each blunt end. The fragment also has a unique internal PacI site almost exactly in the middle of the fragment such that digestion with PacI results in the production of two sub-fragments of about 250 bp each. The fragment was digested with EcoRI, and ligated into EcoRI digested pBluescript II to produce plasmid pBSTK. The pBSTK plasmid was transformed into *E. coli* and clones carrying the recombinant plasmid were identified using the standard IPTG/X-gal method. The Tk gene fragment was then excised from the pBSTK plasmid with BamHI and AccI. In addition, pBR322 was digested with BamHI and AccI, and the 2.5 Kb fragment containing the ampicillin resistance gene and the origin of replication was gel purified. The BamHI-AccI Tk gene fragment and the pBR322 BamHI-AccI fragments were then ligated to generate plasmid pRTK. An aliquot of this plasmid was digested with BamHI and AccI to confirm the presence of the BamHI-AccI Tk gene fragment. The pRTK plasmid was then digested with PacI to linearize the plasmid and PacI ends were blunted and treated with calf intestinal phosphatase to prevent self-ligation. The plasmid construct pSC11, provided by Dr. Bernard Moss of the NIH, was digested with XhoI and PstI, the 3.1 kb fragment was isolated and ligated to the ATI promoter which was produced by PCR of cowpox virus DNA, Brighton Red Strain, using a 5'-primer which produced a KpnI site and a 3'-primer which produced an XhoI site. The ATI-LacZ cassette was then digested with KpnI and PstI and the 3.4 kb fragment was gel-purified. This fragment was blunt-ended and ligated into the blunt ended, linearized pRTK vector to produce the pTK::ATI-LacZ vector having about 250 bp of Tk sequence flanking each end of the ATI-LacZ gene cassette. Recombinant plasmids were identified by PCR with primers specific for the ATI promoter, and the recombinants were confirmed by additional PCR reactions using primers specific for the Tk and LacZ sequences.

Insect cells (LD652 gypsy moth) infected with AmEPV were then transfected with the pTK::ATI-LacZ construct.

The cells were grown in the commercially available TC100 medium (GIBCO). Virus that recombined with the plasmid DNA was then selected by overlaying infected cells, plated at 10-fold serial dilutions of the transfection mixture, with agarose containing X-gal and selecting blue plaques for expansion and further characterization. Out of about 80 plaques total, we were able to select one blue plaque by this method, demonstrating that the LacZ gene presented in the context of the pTK::ATI-LacZ plasmid was taken up by the virus infected cells, and that homologous recombination of the ATI-LacZ cassette into the AmEPV had occurred. Using completely analogous methods to those described above, any expression cassette can be introduced into the Entomopoxvirus genome and expressed in insect cells. Because the ATI promoter is a mammalian (cowpox virus) vector, this experiment also demonstrates the ease with which a gene cassette constructed for mammalian expression can be adapted for expression by recombinant Entomopoxvirus in insect cells.

Figure 9:
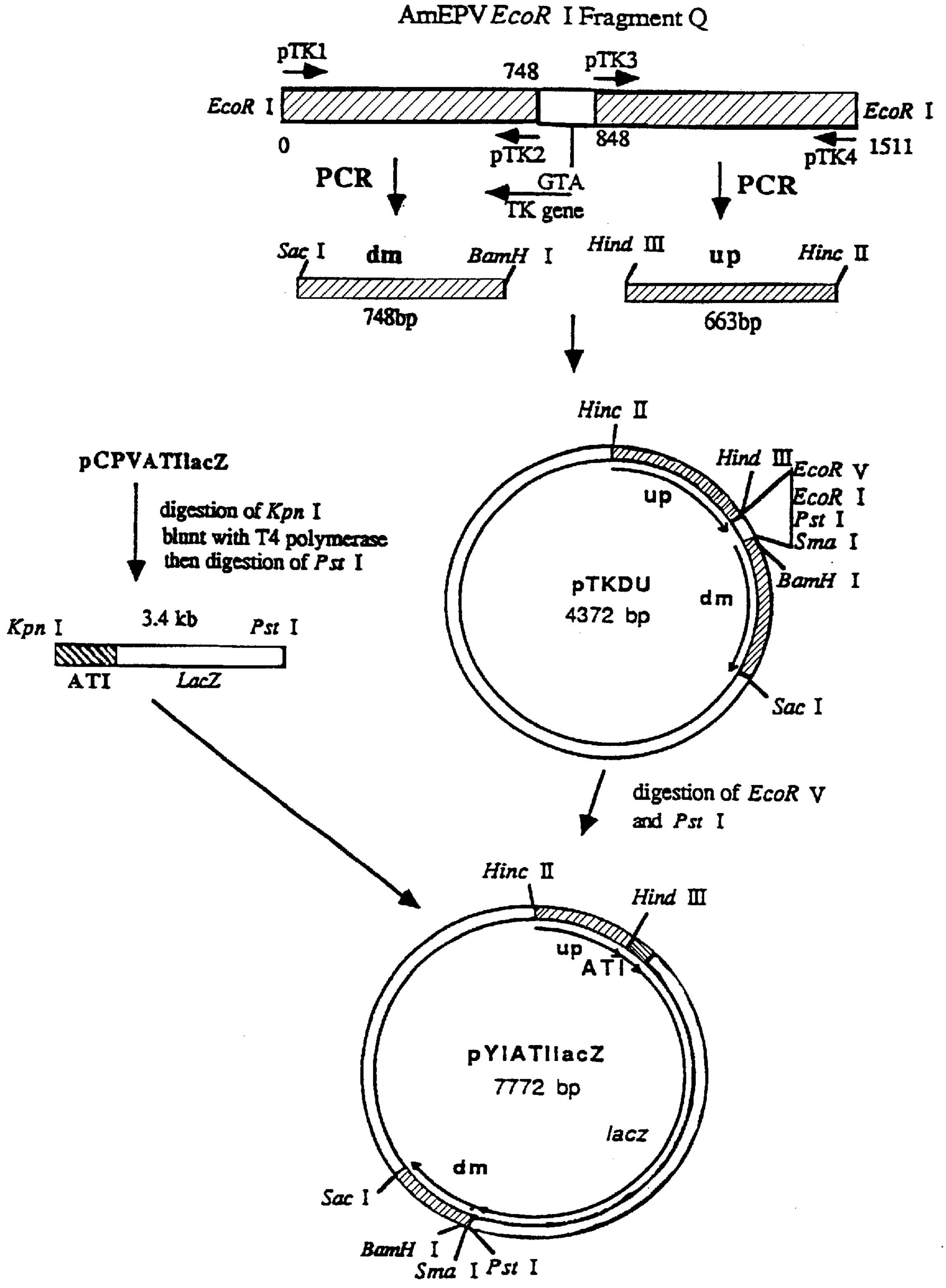
FIG. 9 shows the scheme for providing pYLATILacZ.
Figure 11:
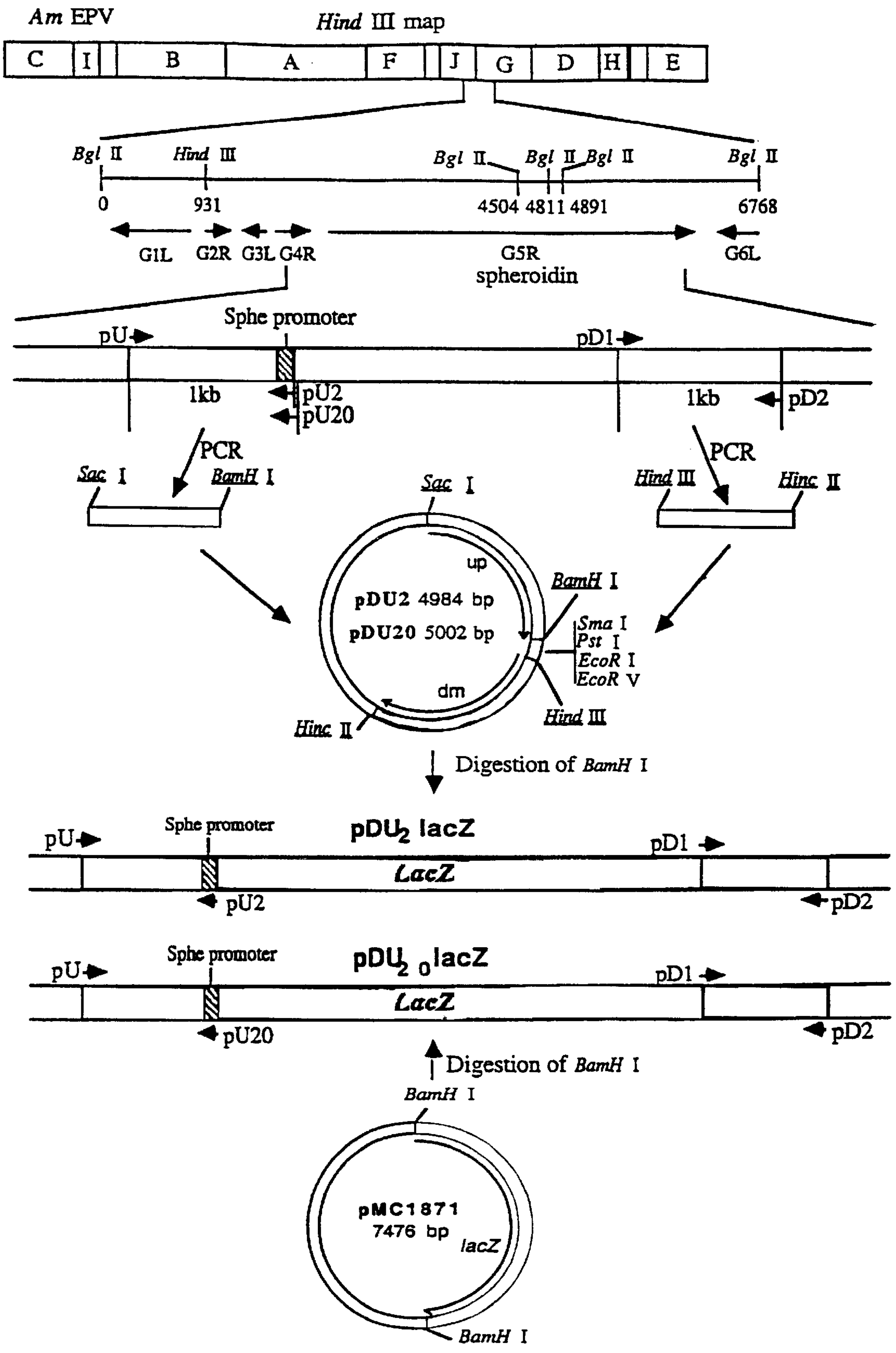
FIG. 11 shows the experiment to further characterize entomopxovirus spheroidin promoter.

The construct used to produce recombinant entomopoxvirus may be modified so as to increase the efficiency with which recombinant virus is produced. This is achieved by the simple expedient of including more Tk gene as flanking sequence on either side of the heterologous gene sought to be recombined into the Entomopoxvirus genome. This increased recombination efficiency was demonstrated in the following experiment (see FIG. 9) in which 748 bp of downstream Tk flanking sequence was used on one side of the ATI-LacZ expression cassette and 664 bp of upstream Tk flanking sequence was used on the other side of the ATI-LacZ expression cassette:

The vector pYLATILacZ was produced as shown in FIG. 11 by PCR amplification of a portion of the EcoRI-Q fragment using as primers pTKI, SEQ ID NO. 65, and pTK2, SEQ ID NO. 66 as a first pair, and pTK3, SEQ ID NO. 67, and pTK4, SEQ ID NO. 68, as a second pair. In this manner, two fragments were produced. The first had SacI and BamHI ends, and the second had HindIII and HincII ends. The first fragment was cloned into pBluescript II (SK+) from Stratagene, and, in a separate step, the second fragment was then cloned into this intermediate clone to produce pTkDU. Because the Tk gene in pTkDU is interrupted, this vector encodes a non-functional Tk gene product. Therefore C11.3 $Tk^-$ cells (produced by a process of adaptation of $Tk^+$ LD652 cells to increasing levels, 10 $\mu$g/ml every 5 weeks, of BuDR over one year up to 100 $\mu$g/ml BuDR) transfected with the pTkDU vector grew well in growth media supplemented with 100 $\mu$g/ml BuDR.

Figure 10:
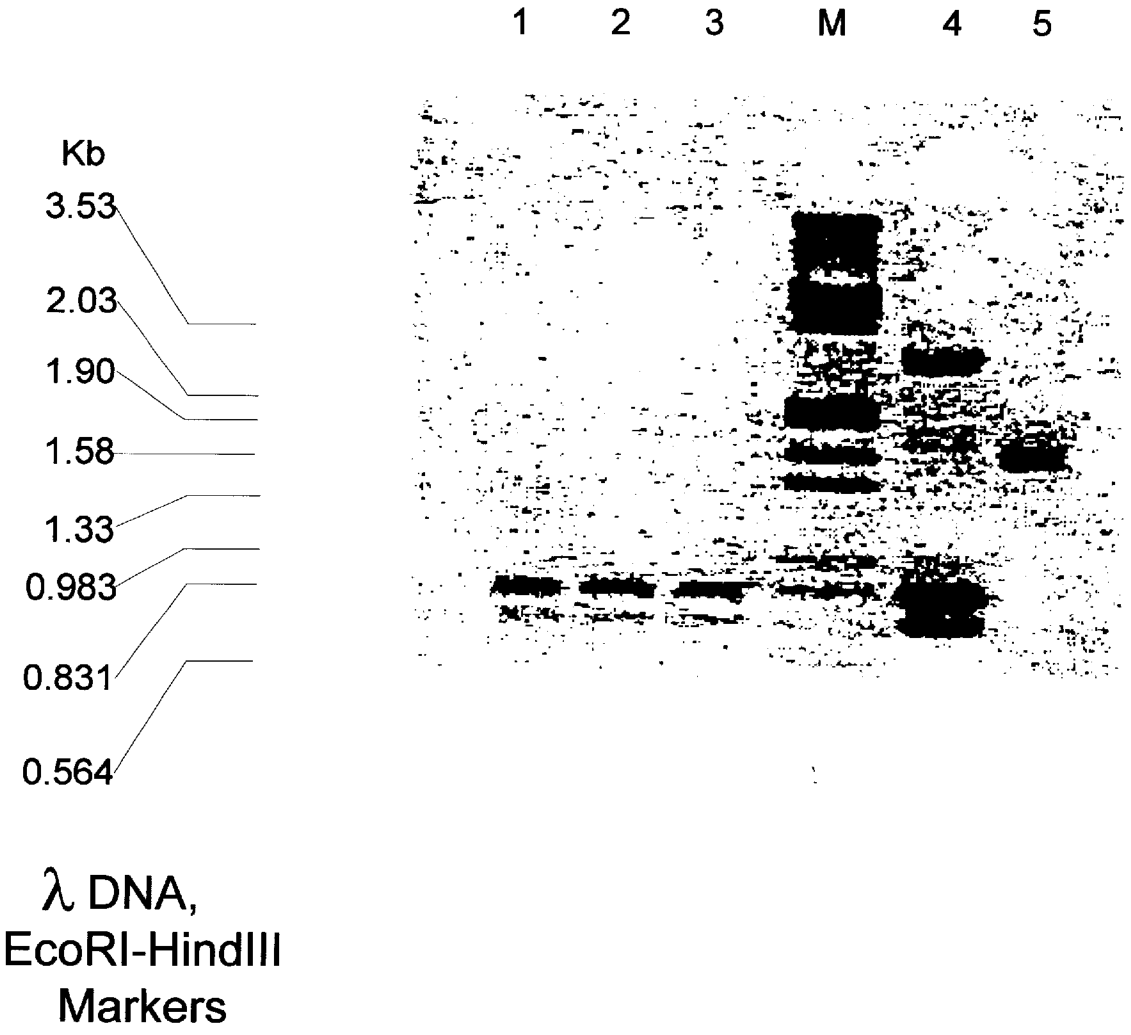
FIG. 10 shows the Southern blot of EcoRI digested AmEPV recombinant.

The ability of this vector to produce recombinant AmEPV was tested by first infecting $Tk^+$ LD652 cells with $Tk^+$ AmEPV. The infected cells were then transfected with the pTkDU vector and the cells were allowed to grow for 4 to 5 days in culture. The entire contents of the cell culture was then used to infect C11.3 $Tk^-$ cells plated with 100 $\mu$g/ml BuDR. Multiple plaques were identified as a result of these steps, thus demonstrating the production of $Tk^-$ recombinant AmEPV. To confirm that the recombinant virus was produced via recombination with the pTkDU vector, virus was isolated, viral DNA was digested with EcoRI, and the digest thus produced was probed with non-radioactively labeled (digoxigenin) EcoRI-Q fragment. Because a new EcoRI site was inserted into the middle of the Tk gene present in the pTkDU vector, if the $Tk^-$ virus was produced via homologous recombination with the transfected pTkDU vector, the predicted Southern blot result is that two fragments would light up, with one fragment having a size of about 748 bp and another fragment of about 664 bp. On the other hand, spontaneous mutants would be predicted to have only one EcoRI fragment having a size of about 1.5 KB. As shown in the Southern blot provided (FIG. 10), two fragments of the predicted size were observed in the digests from several recombinant virus plaques (Lanes 1–3; Lane M=$\lambda$ DNA EcoRI-Hind III molecular weight markers; lane 4=the EcoRI cut pTkDU vector used to create the recombinant viruses shown in lanes 1–3, some partial digestion is noted; lane 5=wild type AmEPV DNA cut with EcoRI-the expected 1.5 KB band is noted).

To produce pYLATILacZ with the heterologous LacZ gene acting as a marker, the pTkDU vector was then digested with EcoRV and PstI to linearize the vector. The KpnI-PstI ATI-LacZ gene cassette was then produced by first digesting with KpnI, blunt ending this end with T4 DNA polymerase and then digesting with PstI. The ATI-LacZ cassette was then ligated to the HincII-PstI linearized pTkDU vector to produce the vector pYLATILacZ. Upon transfection of this construct into AmEPV infected insect cells, blue recombinants are selected as described above.

The production of $Tk^-$ Entomopoxvirus and of blue Entomopoxvirus plaques clearly demonstrates the ability to produce a recombinant Entomopoxvirus and to express an heterologous gene therefrom. It also clearly demonstrates the production of a recombinant cell in which an heterologous protein is produced from a recombinant virus having a thymidine kinase-heterologous gene fusion within its genome. This example also demonstrates the ability to screen for disruption of the thymidine kinase gene. Using exactly analogous methods, the same conclusions for the spheroidin gene are supported by this work. Palmer et al. (1995) have used analogous methods to produce recombinant Entomopoxvirus via insertion of an heterologous gene into the spheroidin locus. A further advantage of the method exemplified in this work is that while recombination into the Entomopoxvirus Tk gene disrupts the Tk gene, the spheroidin gene may be left intact and recombinant Entomopoxvirus could be environmentally stable while embedded in the occlusion body.

EXAMPLE 13

Characterization of the Entomopoxvirus Spheroidin Promoter

To better characterize the Entomopoxvirus spheroidin promoter, the experiment outlined in FIG. 11 was conducted as follows. The end result of the experiment utilizes differential expression from different spheroidin promoter subfragments to drive a reporter gene (LacZ) to show the different strength of the promoter depending on the sequence utilized:

Using PCR primers pU, SEQ ID NO. 69, PU2 SEQ ID NO. 70 and pU20, SEQ ID NO. 71 two different spheroidin promoter fragments having either +2 nucleotides (pU+pU2) or +20 nucleotides (pU+pU20) were produced. In either case, these primers provide a 5'-SacI site and a 3'-BamHI site. In addition, the PCR primers pD1, SEQ ID NO. 72 and pD2, SEQ ID NO. 73 were used to amplify a 1 kb downstream fragment containing the spheroidin coding sequence with a 5'-HindIII and a 3'-HincII terminus. These fragments were then separately cloned into the SacI-BamHI site and the HindIII-HincII site of the commercially available vector pBluescript II ($SK^+$), Stratagene, La Jolla, Calif., to produce vectors pDU2 (4984 bp) and pDU20 (5002 bp). Each of these vectors was then linearized at the BamHI site and the LacZ gene with BamHI termini, derived by digestion of pMC1871 (1746 bp) obtained from Pharmacia Biotech., Inc. Piscataway, N.J. (Cat. No. 27-4945-01) with BamHI, was ligated into the linearized vectors to produce pDU2LacZ and pDU20LacZ. These vectors were then transfected into LD652 cells infected with wt AmEPV at an M.O.I of at least 5, and the amount of LacZ produced 54 hours post-infection was quantitated by freeze-thawing and sonicating the harvest. A chromogenic assay, in which a colored product of ONPG (O-nitrophenyl-β-D-galactoside) is quantitated at 420 nm, according to Miller, J. H., Experiments in *Molecular Genetics*; Cold Spring Harbor Laboratory, Cold Spring Harbor, N.Y., 1972, p. 352–355, using chloroform in place of toluene, was used.

The results of this assay were:

a) For Recombinant AmEPV produced by pDU20LacZ:

$A_{420}$ 0.847

0.878

Average=0.862 b) For Recombinant AmEPV produced by pDU2LacZ:

$A_{420}$ 0.161

0.178

Average=0.170

Thus, the recombinant AmPEV with the +20 spheroidin promoter produced 5.1 times the amount of β-gal activity than did the +2 recombinant.

From this experiment, it is evident that although the spheroidin promoter up to and including the ATG is active, the spheroidin promoter extends beyond the spheroidin ATG.

EXAMPLE 14

Production and Use of a Mammalian/Insect Bi-Functional Vector

Figure 12:
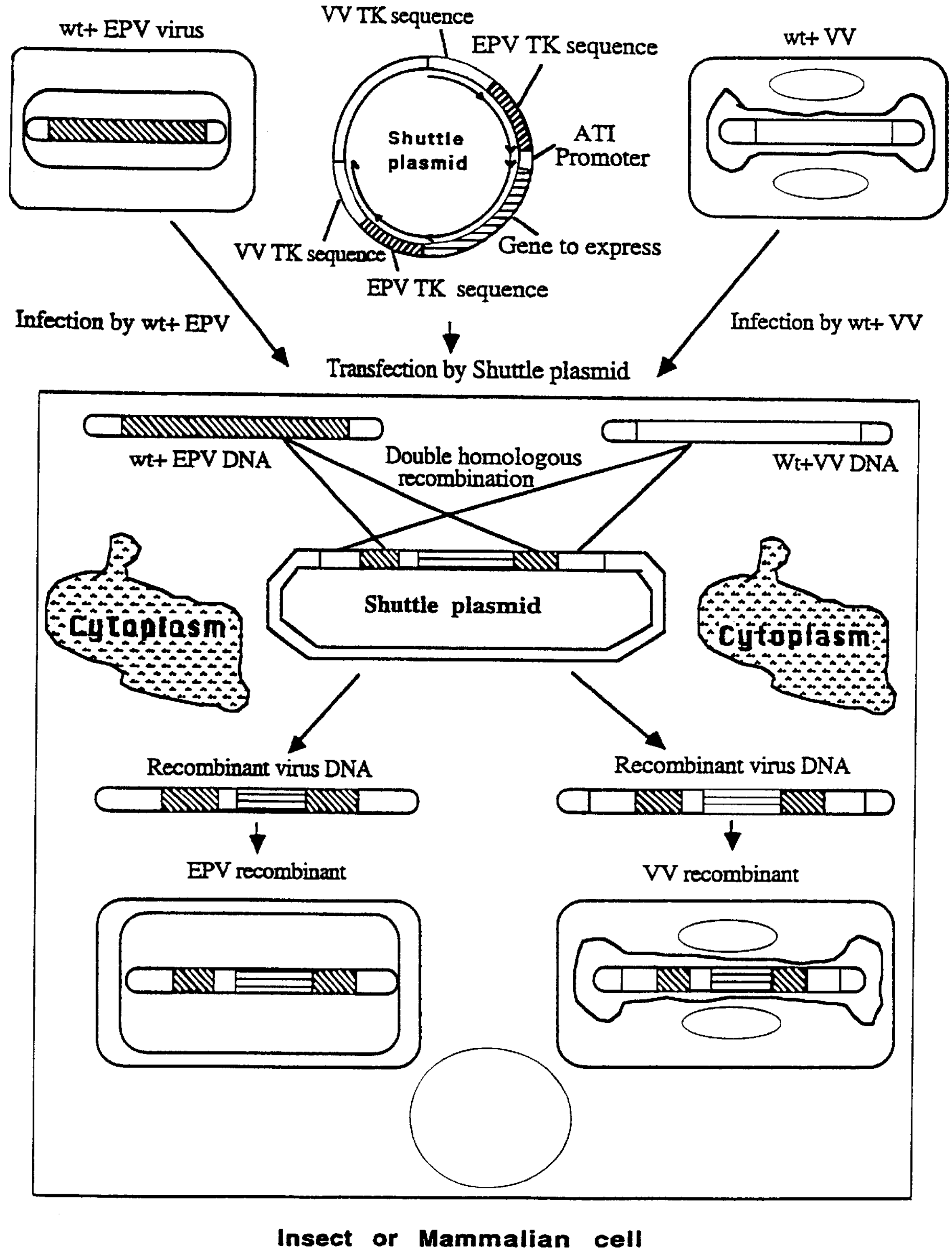
FIG. 12 shows the bi-functional vector for making other recombinant entomopoxvirus or vaccinia virus constructs.

To optimize the utility of the Entomopoxvirus expression system described herein, a bi-functional vector for facile production of either recombinant Entomopoxvirus (for heterologous gene expression in insect cells) or recombinant vaccinia (for heterologous gene expression in mammalian cells) constructs is produced as shown in FIG. 12 and as described below.

Since the vaccinia ATI promoter operates in both Entomopoxvirus infected insect cells, and in vaccinia infected mammalian cells, the ATI promoter is one candidate for use in the bi-functional vector. Naturally, other promoters which similarly function in both host cell types may be utilized. On either side of the ATI promoter gene cassette, AmEPV Tk flanking sequences are provided as described above in example 12. On either side of the AmEPV Tk sequences, vaccinia virus Tk flanking sequences are inserted. Naturally, Tk sequences from Entomopoxvirus strains other than AmEPV could be used and other vertebrate virus Tk flanking sequences than vaccinia Tk sequences could be used. An heterologous gene is then separately cloned into a restriction site such that it is operatively linked to the ATI promoter. Specifically, these steps may be carried out as follows:

pBluescript II (KS+) is digested with BssHII to excise the multiple cloning site and linearize the vector. The linearized vector is then blunt-ended by filling in with nucleotide triphosphates and the Klenow enzyme. A blunt-ended HindIII-XhoI vaccinia DNA fragment (1.76 kb) containing the vaccinia Tk gene is ligated into the blunt-ended vector to create pVTk. pVTk is then cut with EcoRI, which cuts the vaccinia Tk gene into an upstream 786 bp and a downstream 986 bp fragment, and is then blunt-ended with Klenow. The left arm of the AmEPV Tk gene (about 664 bp) is amplified by PCR as described in Example 12, except that the primers are designed to provide SmaI sites at the termini, with an internal HindIII and NotI site being internal to the SmaI site at one end of the amplified fragment. The amplified fragment is cleaved with SmaI and then ligated into the EcoRI cut pVTk vector, to produce pVTkETk0.5. pVTkETk0.5 is then linearized with HindIII, which cuts the AmEPV Tk gene left arm, and blunt-ended with Klenow. The right arm of the AmEPV Tk gene (about 748 bp) is then PCR amplified as described in Example 12, except that the primers are designed to provide SmaI sites at the termini. The amplified fragment is cut with SmaI, and ligated into the linearized pVTkETk0.5 vector to generate pVTkETk having a contiguous segment of nucleotides as follows: 768 bp vaccinia Tk-664 bp AmEPV Tk-748 bp AmEPV Tk-986 bp Vaccinia Tk. Between the two AmEPV Tk segments, there is a unique NotI restriction site. The pVTkETk bi-functional vector is linearized with NotI and is available for insertion of any expression cassette. Thus, to produce an expression cassette, pBluescript II (KS+) is cut with NotI and any other appropriate second enzyme. The ATI promoter is PCR amplified from cowpox virus using primers that provide an NotI restriction site at one end of the promoter and a second site at the other terminus of the promoter which matches the second site used for cleaving the pBluescript vector. The ATI promoter is then ligated into the linearized pBluescript vector. A gene of interest is amplified using PCR primers such that at the downstream end of the gene, there is an NotI site internal to another restriction site, while at the other end, at the start of the sequence to be translated, a site which matches the site external to the NotI and which matches the second site placed at the terminus of the ATI promoter is provided. The fragment is ligated into the pBluescript vector carrying the ATI promoter, in-frame with the promoter, and the construct is amplified by transformation into *E. coli*. The ATI-gene cassette is then excised using NotI and ligated into the pVTkETk bi-functional vector linearized with NotI to produce the bi-functional vector with the ATI promoter driving the heterologous gene. A bi-functional vector produced as described above is then utilized, according to FIG. 12, to produce either entomopoxvirus or vaccinia recombinants.

For production of Entomopoxvirus recombinants which express the foreign gene, insect cells are infected with wild-type Entomopoxvirus and then transfected with the heterologous gene construct, and recombinants containing the heterologous gene are then isolated. For production of vaccinia virus recombinants, mammalian cells are infected with wild-type vaccinia virus and then transfected with the heterologous gene construct, and recombinants containing the heterologous gene are isolated.

It should be understood that the examples and embodiments described herein are for illustrative purposes only. Various modifications or changes in light thereof will be suggested to persons skilled in the art by this specification. The subject invention encompasses recombinant polynucleotide sequences, plasmids, vectors, and transformed hosts which are equivalent to those which are specifically exemplified herein in that the characteristic expression features are retained in said equivalent constructs even if inconsequential modifications to the DNA sequence have been made. For example, it is within the skill of a person trained in the art to use a fragment of the spheroidin gene's non-coding region which is upstream of the structural gene in order to achieve the desired level of expression. Such fragments of the regulatory sequences fall within the scope of the current invention, so long as the desired level of expression which is characteristic of this system is retained. Furthermore, inconsequential changes to the nucleotide sequences can be made without affecting the disclosed functions of these sequences. Such modifications also fall within the scope of the current invention and are to be included within the spirit and purview of this application and the scope of the appended claims.

What is claimed is:

1. An Entomopoxvirus spheroidin gene polynucleotide sequence free from association with other viral nucleotide sequences with which it is associated in nature, characterized by the ability to direct the expression of an heterologous gene to which said sequence or a functional fragment of said sequence is operably linked within a selected host cell, wherein said sequence is either an active spheroidin promoter sequence operably linked to said heterologous gene directly, or said sequence is an active spheroidin promoter operably linked to spheroidin coding sequences which in turn are operably linked to said heterologous gene.

2. A polynucleotide sequence comprising a first polynucleotide sequence comprising an Entomopoxvirus spheroidin gene polynucleotide sequence, including the promoter sequence thereof or a coding sequence thereof operably linked with a second polynucleotide sequence encoding an heterologous gene.

3. A recombinant polynucleotide molecule comprising a polynucleotide sequence encoding the Entomopoxvirus spheroidin promoter sequence operably linked to a selected heterologous gene sequence, said promoter sequence being capable of directing the expression of said gene in a selected host cell.

4. A recombinant polynucleotide molecule comprising a polynucleotide sequence encoding an Entomopoxvirus thymidine kinase promoter sequence, an allelic variant, or a functional fragment thereof, wherein said promoter sequence is operably linked to a selected heterologous gene sequence, said promoter sequence being capable of directing the expression of said gene in a selected host cell.

5. A cell infected with a recombinant virus comprising an Entomopoxvirus spheroidin gene polynucleotide sequence, an allelic variant, or a functional fragment thereof, operably linked to a selected heterologous gene sequence.

6. The cell according to claim 5 selected from the group consisting of insect cells and mammalian cells.

7. A method for producing a selected polypeptide comprising culturing a selected host cell infected with a recombinant virus comprising an Entomopoxvirus thymidine kinase gene polynucleotide sequence operably linked to an heterologous gene sequence encoding said selected polypeptide.

8. A method for producing a selected polypeptide comprising culturing a selected host cell infected with a recombinant virus comprising an Entomopoxvirus spheroidin gene polynucleotide sequence operably linked to a selected heterologous gene sequence encoding said selected polypeptide.

9. A method for screening recombinant virus for insertion of an heterologous gene comprising transforming Entomopoxvirus infected cells with a polynucleotide molecule comprising the heterologous gene sequence inserted into a polynucleotide sequence encoding Entomopox virus spheroidin, wherein the absence of occlusion bodies normally formed by the expression of the spheroidin protein indicates the integration of the heterologous gene.

10. A method for screening recombinant virus for insertion of an heterologous gene comprising infecting said cells with an Entomopoxvirus and transfecting the thus infected cells with a polynucleotide molecule comprising the heterologous gene sequence inserted into a polynucleotide sequence encoding Entomopoxvirus thymidine kinase, wherein the absence of thymidine kinase function indicates the insertion of the heterologous gene.

* * * * *

UNITED STATES PATENT AND TRADEMARK OFFICE

CERTIFICATE OF CORRECTION

PATENT NO. : 6,410,221 B1
DATED : June 25, 2002
INVENTOR(S) : Richard W. Moyer, Richard L. Hall and Michael Gruidl It is certified that error appears in the above-identified patent and that said Letters Patent is hereby corrected as shown below:

<u>Column 7,</u>
Line 67, “pD 1” should read -- pD1 --.

<u>Column 27,</u>
Line 50, “Bgm” should read -- *Bgl*II --.

<u>Column 30,</u>
Line 9, “pUC1 8” should read -- pUC18 --.
Line 12, “pRHS 12” should read -- pRH512 --.
Line 42, “J. P.,et al.” should read -- J.P., *et al.* --.

<u>Column 33,</u>
Line 8, “PAGE. occlusion” should read -- PAGE, occlusion --.

<u>Column 41,</u>
Lines 16 and 22, “$A_{420}$” should read -- $\underline{A}_{420}$ --.

Signed and Sealed this

Seventeenth Day of June, 2003

JAMES E. ROGAN
*Director of the United States Patent and Trademark Office*

SEQUENCE LISTING

<160> NUMBER OF SEQ ID NOS: 78

<210> SEQ ID NO 1
<211> LENGTH: 8457
<212> TYPE: DNA
<213> ORGANISM: Amsacta moorei entomopoxvirus

<400> SEQUENCE: 1
agatctgatg ttctatatat agtacaaatt tgtatgatta attgatattt taaaattcaa 60
gatattaaat attagattct aaactattct tctcattatc aatataacta tcataatcat 120
tttttatttt actacataca ttcataattc tattactatt ttttttatac atatctatta 180
attccataaa ctttttattt tttatattaa atatttctaa tgtatttttta aattcgtcaa 240 tactattaat atcatatcta gaaataaata atgcacctct ataactacta gccaataaat 300
caccaataaa actcatagaa taatataatt ttttaaattc aaatttagat tttatgttga 360
aataaactat ataatataaa aatattatat taaacatacc acaatcggga ctatcatatt 420
gtaattcaaa agtattaaaa aagtaataat ttacattttt aaatatatca tttaaatatt 480
ctgatagtac atcaatgtat aaataagcat aattagtatt aggagtacta ttgtagtgtt 540
tatggctttt tatagtcata tcagattcaa taaacatata ttttttattt tgttttataa 600
gttctggtat ataaccacta ctattaaaaa agtatgcagc ttttttatct ttatcaaagt 660
gtttatctat tacgcaacaa gtaaaatgat cattataaat tataggaaac ataaaaaatc 720
tttttttatc attcattaaa aaaaatttta ctctatcttc aagtttatag catctcatag 780
atgaagctac tgtagcaata tttttatcag ttttttcaaa taaaatcaaa tgaaaataat 840
cataatctgt attaatcata gttaatggat atatacaatt atatatatct cccgaactta 900
accatgtaga tttatcatgt tttcttgggt aagctttagg tttaggatta aatcccaaag 960
gcggtattcc tatttgagca tccaaatcat cataaattgt ggcaaatgta gaaaaatctc 1020
ttgttttgga taattctgat tttagaaaag actttctcat atatactaat ggaatgcctt 1080
tatatttttt agatgtaata aaagtattaa tatttatatt tttatcttgt aaatattttt 1140
ttatagtcca aaatagaaaa aattttcttt taatattatt ttcaaaatta atattattaa 1200
tatgatttgg atctaaaact aattcattat ataatatttc caagtatttt ataggtataa 1260
atgttacttt acctcttgtt tcatcatcat catctatttt ttctaatata gctatatttg 1320
cattagtatt atatttaata ggatttataa aatataccat attatctatt ttactaaaaa 1380
ataacataga cataaaatta ataccagatt ctggcatttt taaattttta tttggaaatc 1440
ttctaatttt attattcatt atttatttaa taaatgtttc tagtttattt caatacattt 1500
ttaataataa ttttattatt tggtattata ggtatttata tattaacatt tgtgtttaat 1560
atagattttt taataaataa taataaaata tatatattat catataacgc aactaatata 1620
aacaatataa ataatttaaa tttatacgat tattcagata ttatattttt gacaaatttt 1680
aacataaata ataatctttt agtaacacaa gctaataatt tacaagatat accaatattt 1740
aatgtaaata atattatatc taatcaatat aatttttatt cagcgtctag taataatgta 1800

-continued

```
aatatattat taggattaag aaaaacatta aatataaata gaaatccatt tttattattt   1860
agaaatacat ctctagctat agttttcaat aataatgaaa cttttcactg ttatataagt   1920
tcaaatcaaa atagtgatgt attagatata gtatcacata tagaatttat gaaatctaga   1980
tataataaat atgtaattat aggagaaata cccgtaaata ataatatatc tattaataat   2040
atattaaata attttgctat tataactaat gtgagattaa tagataaata taactctata   2100
atatcatttt taaatatcaa cgtaggaaca ctttttgtca taaatccata atatttagta   2160
ataatcacta acatattttt tattaaaatg aataaaatat atattgttat tgtcaatatt   2220
ttatatcatt ttacagtctt attttttttt tttgctttta ggtataattt taccttctaa   2280
acgtttatct ccccaaacat ctacagtaga tggtttatta gattctgtgt tatacacatc   2340
tgctggattt gcggcatttg tatccaaacc ataatatcca ggtctataat tatctttaaa   2400
aacttgggat tgagatactt cttcagtttt taaattatta aaatatccaa gattattttt   2460
ttttgatgaa gacataattg atattataat actttataga tatgtcaata tttatctact   2520
atattttcaa caatagattt tatatatata aaagaatgaa tactgtacaa attttagttg   2580
tcatattaat aacaacagca ttatcttttc tagtttttca attatggtat tatgccgaaa   2640
attacgaata tatattaaga tataatgata catattcaaa tttacaattt gcgagaagcg   2700
caaatataaa ttttgatgat ttaactgttt ttgatcccaa cgataatgtt tttaatgttg   2760
aagaaaaatg gcgctgtgct tcaactaata ataatatatt ttatgcagtt tcaacttttg   2820
gatttttaag tacagaaagt actggtatta atttaacata tacaaattct agagattgta   2880
ttatagattt attttctaga attataaaaa tagtatatga tccttgtact gtcgaaacat   2940
ctaacgattg tagattatta agattattga tggccaatac atcataaata cattataata   3000
ttattataat atcaatcata atttttatat atattttatc taaaaggact ttttattttt   3060
tatatattaa taataataaa tgagtaacgt acctttagca accaaaaaca taagaaaatt   3120
atcaaatcga aaatatgaaa taaagattta tttaaaagat gaaaatactt gtttcgaacg   3180
tgtagtagat atggtagttc cattatatga tgtgtgtaat gaaacttctg gtgttacttt   3240
agaatcatgt agtccaaata tagaagtaat tgaattagac aatactcatg ttagaatcaa   3300
agttcacggc gatacattaa aagaaatgtg ttttgaatta ttgttcccgt gtaatgtaaa   3360
cgaagcccaa gtatggaaat atgtaagtcg attattgcta gataatgtat cacataatga   3420
cgtaaaatat aaattagcta attttagact gactcttaat ggaaaacatt taaaattaaa   3480
agaaatcgat caaccgctat ttatttattt tgtcgatgat ttgggaaatt atggattaat   3540
tactaaggaa aatattcaaa ataataattt acaagttaac aaagatgcat catttattac   3600
tatatttcca caatatgcgt atatttgttt aggtagaaaa gtatatttaa atgaaaaagt   3660
aacttttgat gtaactacag atgcaactaa tattacttta gattttaata aatctgttaa   3720
tatcgcagta tcattccttg atatatatta cgaagttaat aataatgaac aaaaagattt   3780
attaaaagat ttacttaaga gatacggtga atttgaagtc tataacgcag atactggatt   3840
aatttatgct aaaaatctaa gtattaaaaa ttatgatact gtgattcaag tagaaaggtt   3900
gccagttaat ttgaaagtta gagcatatac taaggatgaa aatggtcgca atctatgttt   3960
gatgaaaata acatctagta cagaagtaga ccccgagtat gtaactagta ataatgcttt   4020
attgggtacg ctcagagtat ataaaaagtt tgataaatct catttaaaaa ttgtaatgca   4080
taacagagga agtggtaatg tatttccatt aagatcatta tatctggaat tgtctaatgt   4140
aaaaggatat ccagttaaag catctgatac ttcgagatta gatgttggta tttacaaatt   4200
```

-continued

```
aaataaaatt tatgtagata acgacgaaaa taaaattata ttggaagaaa ttgaagcaga   4260

atatagatgc ggaagacaag tattccacga acgtgtaaaa cttaataaac accaatgtaa   4320

atatactccc aaatgtccat tccaatttgt tgtaaacagc ccagatacta cgattcactt   4380

atatggtatt tctaatgttt gtttaaaacc taaagtaccc aaaaatttaa gactttgggg   4440

atggatttta gattgcgata cttctagatt tattaaacat atggctgatg gatctgatga   4500

tttagatctt gacgttaggc ttaatagaaa tgatatatgt ttaaaacaag ccataaaaca   4560

acattatact aatgtaatta tattagagta cgcaaataca tatccaaatt gcacattatc   4620

attgggtaat aatagattta ataatgtatt tgatatgaat gataacaaaa ctatatctga   4680

gtatactaac tttacaaaaa gtagacaaga ccttaataac atgtcatgta tattaggaat   4740

aaacataggt aattccgtaa atattagtag tttgcctggt tgggtaacac ctcacgaagc   4800

taaaattcta agatctggtt gtgctagagt tagagaattt tgtaaatcat tctgtgatct   4860

ttctaataag agattctatg ctatggctag agatctcgta agtttactat ttatgtgtaa   4920

ctatgttaat attgaaatta acgaagcagt atgcgaatat cctggatatg tcatattatt   4980

cgcaagagct attaaagtaa ttaatgattt attattaatt aacggagtag ataatctagc   5040

aggatattca atttccttac ctatacatta tggatctact gaaaagactc taccaaatga   5100

aaagtatggt ggtgttgata agaaatttaa atatctattc ttaaagaata aactaaaaga   5160

tttaatgcgt gatgctgatt ttgtccaacc tccattatat atttctactt actttagaac   5220

tttattggat gctccaccaa ctgataatta tgaaaaatat ttggttgatt cgtccgtaca   5280

atcacaagat gttctacagg gtctgttgaa tacatgtaat actattgata ctaatgctag   5340

agttgcatca agtgttattg gatatgttta tgaaccatgc ggaacatcag aacataaaat   5400

tggttcagaa gcattgtgta aaatggctaa agaagcatct agattaggaa atctaggttt   5460

agtaaatcgt attaatgaaa gtaattacaa caaatgtaat aaatatggtt atagaggagt   5520

atacgaaaat aacaaactaa aaacaaaata ttatagagaa atatttgatt gtaatcctaa   5580

taataataat gaattaatat ccagatatgg atatagaata atggatttac ataaaattgg   5640

agaaattttt gcaaattacg atgaaagtga atctccttgc gaacgaagat gtcattactt   5700

ggaagataga ggtcttttat atggtcctga atatgtacat cacagatatc aagaatcatg   5760

tacgcctaat acgtttggaa ataacacaaa ttgtgtaaca agaaatggtg aacaacacgt   5820

atacgaaaat agttgtggag ataatgcaac atgtggaaga agaacaggat atggaagaag   5880

aagtagggat gaatggaatg actatagaaa accccacgtt tatgacaatt gtgccgatgc   5940

aaatagttca tcttcagata gctgttcaga cagtagtagt agtagtgaat ctgaatctga   6000

ttcagatgga tgttgcgaca cagatgctag tttagattct gatattgaaa attgttatca   6060

aaatccatca aaatgtgatg caggatgcta aatgaaattt aatattatat aatattaact   6120

tacaagttat aaaaatcatt aaaatgattt tttaaaatga tattatcgat agttgtgata   6180

atgtgctctt ttattttatt aattgcgatg attataatat tatcttttag atatatttaa   6240

tattaattat aaatcgactg acaataatat ttattcctat tcataataat catctgctat   6300

atatattaat gtatcattct ctattataaa tataggtata ttgtctttat caatcattaa   6360

ttttgctaca gctgtattat ctttatatac tatatttgtg tctttgttta ataaaccttt   6420

taatatagtg gctctatcat aatctttaca atatgatatg ggatataatt ttatattaat   6480

aataacatta gatacgttca tttctttcat tctagtttta cgtattgtgt caaaaattat   6540
```

-continued

```
ttcattttct gctggttcta tatatttata tgtgttatga atagattcga tagatgatga   6600

ttttaataaa tcaaatataa catttatttt accttgttta tcttttataa tatctaatat   6660

ttctttatct acagattttc tgttgttggt atatgatatt aaaaaatgaa cgttaacata   6720

tctatattct tgtggtaaat ctttatgaga atttaatctt atagatcttc ctattatttg   6780

ttttaattct gattcattcc acggcatatc taatataatt atatcattaa tacatttgaa   6840

tgatatgcct tcagatccag cgtaagaaaa tatgcaaact tttacttttt taccattatt   6900

attttcataa ttattatatt cgtttaattc attatctcta gtttttaaag ttttgctaga   6960

atattcaata taagaaatat taaaacaatt aaaataacat tttaaacttg atattccttc   7020

aaaattaact aaaggttcaa atattaatac ttttcctctc gaatttaaaa ttattttaca   7080

agtttctata tatttacacg aatattgata taatatatta taattattta tatcagtgat   7140

tggtaaatta gtttttattt ttatattatc atttttaaaa ctttcaataa aagattcaga   7200

gaaattaata ttttttgtaa actcggaaaa ttcagcaagt tttcttttaa tcatatcatt   7260

atattctata ttatctaaat ctccttttat tttaagatca taaaaagcaa atgaagatat   7320

taatcttctc atagttttta aaccacctaa ttcagtttta taatcatatt tttctgccat   7380

attatataat ttagattgct catctgacat aattatatta tgataaaata tatttttttt   7440

tgcatatcca tctatataat ttgtttctgt taaactatct gcttctatta atcttttata   7500

agaacatata gctaataatg tttctcttaa ttccttaaaa ttaattaact ttccattatt   7560

tatatattct tcttttatat tcataacatt tggtctaagt aaacctatta aattattaaa   7620

ttcagaaata ttattagtta ctggagtagc ggacatacat aatattttat tattttcgaa   7680

atttgctaat tttattaatt ttttataaat aggagtaaaa tttctttcgt tattatcttt   7740

tttaacagtt cttgatatta atttatgaac ttcgtctatt attattagta atctactttt   7800

tttattaaga gaactttcta tagatctata tatattatta aatttatcta aactagatga   7860

cgaatcataa tatataaatt ttatattact ggtatctgat atatatgatc ttatagtatt   7920

taaccaagga tctatgtata atgatttttt aataaatatt aaaattatcc atcttggaaa   7980

taattctttt atatatttta taatatacac agcagttaat gtttttccca taccagtatc   8040

ccaaaataat aacatactat tcaaattttt taatcctatg aatattctac ttacaaaata   8100

ttgataatct tgtaatgtaa tttcagtatt tgtaatatta ttcataattt tattaggcaa   8160

atgttgtgtt ttatcaagtg cataatttat atgtttacca acaatagaat ctaatgcaaa   8220

catttagtta tataaaaaat aatatttata ttaacttaag atgtttcatt aattttatgt   8280

ctgtgatgtg gagttaaaac ccaagatatt gatatatcta tatcattaat tcttcttttg   8340

aatctatgtc tatcaatcgc aaatttatcc cagtataatt ttcgagtttg ttttgcagca   8400

tataaccaaa catacataat gtggagtttt ggtggttcgg atgaaaagcg tacttt       8457
```

<210> SEQ ID NO 2
<211> LENGTH: 464
<212> TYPE: PRT
<213> ORGANISM: Amsacta moorei entomopoxvirus

<400> SEQUENCE: 2

```
Met Asn Asn Lys Ile Arg Arg Phe Pro Asn Lys Asn Leu Lys Met Pro
1               5                   10                  15

Glu Ser Gly Ile Asn Phe Met Ser Met Leu Phe Phe Ser Lys Ile Asp
            20                  25                  30

Asn Met Val Tyr Phe Ile Asn Pro Ile Lys Tyr Asn Thr Asn Ala Asn
```

-continued

```
        35                  40                  45

Ile Ala Ile Leu Glu Lys Ile Asp Asp Asp Asp Glu Thr Arg Gly Lys
    50                  55                  60

Val Thr Phe Ile Pro Ile Lys Tyr Leu Glu Ile Leu Tyr Asn Glu Leu
65                  70                  75                  80

Val Leu Asp Pro Asn His Ile Asn Asn Ile Asn Phe Glu Asn Asn Ile
                85                  90                  95

Lys Arg Lys Phe Phe Leu Phe Trp Thr Ile Lys Lys Tyr Leu Gln Asp
            100                 105                 110

Lys Asn Ile Asn Ile Asn Thr Phe Ile Thr Ser Lys Lys Tyr Lys Gly
        115                 120                 125

Ile Pro Leu Val Tyr Met Arg Lys Ser Phe Leu Lys Ser Glu Leu Ser
    130                 135                 140

Lys Thr Arg Asp Phe Ser Thr Phe Ala Thr Ile Tyr Asp Asp Leu Asp
145                 150                 155                 160

Ala Gln Ile Gly Ile Pro Pro Leu Gly Phe Asn Pro Lys Pro Lys Ala
                165                 170                 175

Tyr Pro Arg Lys His Asp Lys Ser Thr Trp Leu Ser Ser Gly Asp Ile
            180                 185                 190

Tyr Asn Cys Ile Tyr Pro Leu Thr Met Ile Asn Thr Asp Tyr Asp Tyr
        195                 200                 205

Phe His Leu Ile Leu Phe Glu Lys Thr Asp Lys Asn Ile Ala Thr Val
    210                 215                 220

Ala Ser Ser Met Arg Cys Tyr Lys Leu Glu Asp Arg Val Lys Phe Phe
225                 230                 235                 240

Leu Met Asn Asp Lys Lys Arg Phe Phe Met Phe Pro Ile Ile Tyr Asn
                245                 250                 255

Asp His Phe Thr Cys Cys Val Ile Asp Lys His Phe Asp Lys Asp Lys
            260                 265                 270

Lys Ala Ala Tyr Phe Phe Asn Ser Ser Gly Tyr Ile Pro Glu Leu Ile
        275                 280                 285

Lys Gln Asn Lys Lys Tyr Met Phe Ile Glu Ser Asp Met Thr Ile Lys
    290                 295                 300

Ser His Lys His Tyr Asn Ser Thr Pro Asn Thr Asn Tyr Ala Tyr Leu
305                 310                 315                 320

Tyr Ile Asp Val Leu Ser Glu Tyr Leu Asn Asp Ile Phe Lys Asn Val
                325                 330                 335

Asn Tyr Tyr Phe Phe Asn Thr Phe Glu Leu Gln Tyr Asp Ser Pro Asp
            340                 345                 350

Cys Gly Met Phe Asn Ile Ile Phe Leu Tyr Tyr Ile Val Tyr Phe Asn
        355                 360                 365

Ile Lys Ser Lys Phe Glu Phe Lys Lys Leu Tyr Tyr Ser Met Ser Phe
    370                 375                 380

Ile Gly Asp Leu Leu Ala Ser Ser Tyr Arg Gly Ala Leu Phe Ile Ser
385                 390                 395                 400

Arg Tyr Asp Ile Asn Ser Ile Asp Glu Phe Lys Asn Thr Leu Glu Ile
                405                 410                 415

Phe Asn Ile Lys Asn Lys Lys Phe Met Glu Leu Ile Asp Met Tyr Lys
            420                 425                 430

Lys Asn Ser Asn Arg Ile Met Asn Val Cys Ser Lys Ile Lys Asn Asp
        435                 440                 445

Tyr Asp Ser Tyr Ile Asp Asn Glu Lys Asn Ser Leu Glu Ser Asn Ile
    450                 455                 460
```

<210> SEQ ID NO 3
<211> LENGTH: 225
<212> TYPE: PRT
<213> ORGANISM: Amsacta moorei entomopoxvirus

<400> SEQUENCE: 3

```
Met Phe Leu Val Tyr Phe Asn Thr Phe Leu Ile Ile Ile Leu Leu Phe
1               5                   10                  15

Gly Ile Ile Gly Ile Tyr Ile Leu Thr Phe Val Phe Asn Ile Asp Phe
            20                  25                  30

Leu Ile Asn Asn Asn Lys Ile Tyr Ile Leu Ser Tyr Asn Ala Thr Asn
        35                  40                  45

Ile Asn Asn Ile Asn Asn Leu Asn Leu Tyr Asp Tyr Ser Asp Ile Ile
    50                  55                  60

Phe Leu Thr Asn Phe Asn Ile Asn Asn Asn Leu Leu Val Thr Gln Ala
65                  70                  75                  80

Asn Asn Leu Gln Asp Ile Pro Ile Phe Asn Val Asn Asn Ile Ile Ser
                85                  90                  95

Asn Gln Tyr Asn Phe Tyr Ser Ala Ser Ser Asn Asn Val Asn Ile Leu
            100                 105                 110

Leu Gly Leu Arg Lys Thr Leu Asn Ile Asn Arg Asn Pro Phe Leu Leu
        115                 120                 125

Phe Arg Asn Thr Ser Leu Ala Ile Val Phe Asn Asn Asn Glu Thr Phe
    130                 135                 140

His Cys Tyr Ile Ser Ser Asn Gln Asn Ser Asp Val Leu Asp Ile Val
145                 150                 155                 160

Ser His Ile Glu Phe Met Lys Ser Arg Tyr Asn Lys Tyr Val Ile Ile
                165                 170                 175

Gly Glu Ile Pro Val Asn Asn Asn Ile Ser Ile Asn Asn Ile Leu Asn
            180                 185                 190

Asn Phe Ala Ile Ile Thr Asn Val Arg Leu Ile Asp Lys Tyr Asn Ser
        195                 200                 205

Ile Ile Ser Phe Leu Asn Ile Asn Val Gly Thr Leu Phe Val Ile Asn
    210                 215                 220

Pro
225
```

<210> SEQ ID NO 4
<211> LENGTH: 78
<212> TYPE: PRT
<213> ORGANISM: Amsacta moorei entomopoxvirus

<400> SEQUENCE: 4

```
Met Ser Ser Ser Lys Lys Asn Asn Leu Gly Tyr Phe Asn Asn Leu Lys
1               5                   10                  15

Thr Glu Glu Val Ser Gln Ser Gln Val Phe Lys Asp Asn Tyr Arg Pro
            20                  25                  30

Gly Tyr Tyr Gly Leu Asp Thr Asn Ala Ala Asn Pro Ala Asp Val Tyr
        35                  40                  45

Asn Thr Glu Ser Asn Lys Pro Ser Thr Val Asp Val Trp Gly Asp Lys
    50                  55                  60

Arg Leu Glu Gly Lys Ile Ile Pro Lys Ser Lys Lys Lys Lys
65                  70                  75
```

<210> SEQ ID NO 5

-continued

<211> LENGTH: 161
<212> TYPE: PRT
<213> ORGANISM: Amsacta moorei entomopoxvirus

<400> SEQUENCE: 5

```
Met Ser Ile Phe Ile Tyr Tyr Ile Phe Asn Asn Arg Phe Tyr Ile Tyr
1               5                   10                  15

Lys Arg Met Asn Thr Val Gln Ile Leu Val Val Ile Leu Ile Thr Thr
            20                  25                  30

Ala Leu Ser Phe Leu Val Phe Gln Leu Trp Tyr Tyr Ala Glu Asn Tyr
        35                  40                  45

Glu Tyr Ile Leu Arg Tyr Asn Asp Thr Tyr Ser Asn Leu Gln Phe Ala
    50                  55                  60

Arg Ser Ala Asn Ile Asn Phe Asp Asp Leu Thr Val Phe Asp Pro Asn
65                  70                  75                  80

Asp Asn Val Phe Asn Val Glu Glu Lys Trp Arg Cys Ala Ser Thr Asn
                85                  90                  95

Asn Asn Ile Phe Tyr Ala Val Ser Thr Phe Gly Phe Leu Ser Thr Glu
            100                 105                 110

Ser Thr Gly Ile Asn Leu Thr Tyr Thr Asn Ser Arg Asp Cys Ile Ile
        115                 120                 125

Asp Leu Phe Ser Arg Ile Ile Lys Ile Val Tyr Asp Pro Cys Thr Val
    130                 135                 140

Glu Thr Ser Asn Asp Cys Arg Leu Leu Arg Leu Leu Met Ala Asn Thr
145                 150                 155                 160

Ser
```

<210> SEQ ID NO 6
<211> LENGTH: 1003
<212> TYPE: PRT
<213> ORGANISM: Amsacta moorei entomopoxvirus

<400> SEQUENCE: 6

```
Met Ser Asn Val Pro Leu Ala Thr Lys Thr Ile Arg Lys Leu Ser Asn
1               5                   10                  15

Arg Lys Tyr Glu Ile Lys Ile Tyr Leu Lys Asp Glu Asn Thr Cys Phe
            20                  25                  30

Glu Arg Val Val Asp Met Val Val Pro Leu Tyr Asp Val Cys Asn Glu
        35                  40                  45

Thr Ser Gly Val Thr Leu Glu Ser Cys Ser Pro Asn Ile Glu Val Ile
    50                  55                  60

Glu Leu Asp Asn Thr His Val Arg Ile Lys Val His Gly Asp Thr Leu
65                  70                  75                  80

Lys Glu Met Cys Phe Glu Leu Leu Phe Pro Cys Asn Val Asn Glu Ala
                85                  90                  95

Gln Val Trp Lys Tyr Val Ser Arg Leu Leu Leu Asp Asn Val Ser His
            100                 105                 110

Asn Asp Val Lys Tyr Lys Leu Ala Asn Phe Arg Leu Thr Leu Asn Gly
        115                 120                 125

Lys His Leu Lys Leu Lys Glu Ile Asp Gln Pro Leu Phe Ile Tyr Phe
    130                 135                 140

Val Asp Asp Leu Gly Asn Tyr Gly Leu Ile Thr Lys Glu Asn Ile Gln
145                 150                 155                 160

Asn Asn Asn Leu Gln Val Asn Lys Asp Ala Ser Phe Ile Thr Ile Phe
                165                 170                 175
```

-continued

```
Pro Gln Tyr Ala Tyr Ile Cys Leu Gly Arg Lys Val Tyr Leu Asn Glu
            180                 185                 190

Lys Val Thr Phe Asp Val Thr Thr Asp Ala Thr Asn Ile Thr Leu Asp
        195                 200                 205

Phe Asn Lys Ser Val Asn Ile Ala Val Ser Phe Leu Asp Ile Tyr Tyr
    210                 215                 220

Glu Val Asn Asn Asn Glu Gln Lys Asp Leu Leu Lys Asp Leu Leu Lys
225                 230                 235                 240

Arg Tyr Gly Glu Phe Glu Val Tyr Asn Ala Asp Thr Gly Leu Ile Tyr
                245                 250                 255

Ala Lys Asn Leu Ser Ile Lys Asn Tyr Asp Thr Val Ile Gln Val Glu
            260                 265                 270

Arg Leu Pro Val Asn Leu Lys Val Arg Ala Tyr Thr Lys Asp Glu Asn
        275                 280                 285

Gly Arg Asn Leu Cys Leu Met Lys Ile Thr Ser Ser Thr Glu Val Asp
    290                 295                 300

Pro Glu Tyr Val Thr Ser Asn Asn Ala Leu Leu Gly Thr Leu Arg Val
305                 310                 315                 320

Tyr Lys Lys Phe Asp Lys Ser His Leu Lys Ile Val Met His Asn Arg
                325                 330                 335

Gly Ser Gly Asn Val Phe Pro Leu Arg Ser Leu Tyr Leu Glu Leu Ser
            340                 345                 350

Asn Val Lys Gly Tyr Pro Val Lys Ala Ser Asp Thr Ser Arg Leu Asp
        355                 360                 365

Val Gly Ile Tyr Lys Leu Asn Lys Ile Tyr Val Asp Asn Asp Glu Asn
    370                 375                 380

Lys Ile Ile Leu Glu Glu Ile Glu Ala Glu Tyr Arg Cys Gly Arg Gln
385                 390                 395                 400

Val Phe His Glu Arg Val Lys Leu Asn Lys His Gln Cys Lys Tyr Thr
                405                 410                 415

Pro Lys Cys Pro Phe Gln Phe Val Val Asn Ser Pro Asp Thr Thr Ile
            420                 425                 430

His Leu Tyr Gly Ile Ser Asn Val Cys Leu Lys Pro Lys Val Pro Lys
        435                 440                 445

Asn Leu Arg Leu Trp Gly Trp Ile Leu Asp Cys Asp Thr Ser Arg Phe
    450                 455                 460

Ile Lys His Met Ala Asp Gly Ser Asp Asp Leu Asp Leu Asp Val Arg
465                 470                 475                 480

Leu Asn Arg Asn Asp Ile Cys Leu Lys Gln Ala Ile Lys Gln His Tyr
                485                 490                 495

Thr Asn Val Ile Ile Leu Glu Tyr Ala Asn Thr Tyr Pro Asn Cys Thr
            500                 505                 510

Leu Ser Leu Gly Asn Asn Arg Phe Asn Asn Val Phe Asp Met Asn Asp
        515                 520                 525

Asn Lys Thr Ile Ser Glu Tyr Thr Asn Phe Thr Lys Ser Arg Gln Asp
    530                 535                 540

Leu Asn Asn Met Ser Cys Ile Leu Gly Ile Asn Ile Gly Asn Ser Val
545                 550                 555                 560

Asn Ile Ser Ser Leu Pro Gly Trp Val Thr Pro His Glu Ala Lys Ile
                565                 570                 575

Leu Arg Ser Gly Cys Ala Arg Val Arg Glu Phe Cys Lys Ser Phe Cys
            580                 585                 590

Asp Leu Ser Asn Lys Arg Phe Tyr Ala Met Ala Arg Asp Leu Val Ser
```

-continued

```
        595                 600                 605

Leu Leu Phe Met Cys Asn Tyr Val Asn Ile Glu Ile Asn Glu Ala Val
    610                 615                 620

Cys Glu Tyr Pro Gly Tyr Val Ile Leu Phe Ala Arg Ala Ile Lys Val
625                 630                 635                 640

Ile Asn Asp Leu Leu Leu Ile Asn Gly Val Asp Asn Leu Ala Gly Tyr
                645                 650                 655

Ser Ile Ser Leu Pro Ile His Tyr Gly Ser Thr Glu Lys Thr Leu Pro
            660                 665                 670

Asn Glu Lys Tyr Gly Gly Val Asp Lys Lys Phe Lys Tyr Leu Phe Leu
        675                 680                 685

Lys Asn Lys Leu Lys Asp Leu Met Arg Asp Ala Asp Phe Val Gln Pro
    690                 695                 700

Pro Leu Tyr Ile Ser Thr Tyr Phe Arg Thr Leu Leu Asp Ala Pro Pro
705                 710                 715                 720

Thr Asp Asn Tyr Glu Lys Tyr Leu Val Asp Ser Ser Val Gln Ser Gln
                725                 730                 735

Asp Val Leu Gln Gly Leu Leu Asn Thr Cys Asn Thr Ile Asp Thr Asn
            740                 745                 750

Ala Arg Val Ala Ser Ser Val Ile Gly Tyr Val Tyr Glu Pro Cys Gly
        755                 760                 765

Thr Ser Glu His Lys Ile Gly Ser Glu Ala Leu Cys Lys Met Ala Lys
    770                 775                 780

Glu Ala Ser Arg Leu Gly Asn Leu Gly Leu Val Asn Arg Ile Asn Glu
785                 790                 795                 800

Ser Asn Tyr Asn Lys Cys Asn Lys Tyr Gly Tyr Arg Gly Val Tyr Glu
                805                 810                 815

Asn Asn Lys Leu Lys Thr Lys Tyr Tyr Arg Glu Ile Phe Asp Cys Asn
            820                 825                 830

Pro Asn Asn Asn Asn Glu Leu Ile Ser Arg Tyr Gly Tyr Arg Ile Met
        835                 840                 845

Asp Leu His Lys Ile Gly Glu Ile Phe Ala Asn Tyr Asp Glu Ser Glu
    850                 855                 860

Ser Pro Cys Glu Arg Arg Cys His Tyr Leu Glu Asp Arg Gly Leu Leu
865                 870                 875                 880

Tyr Gly Pro Glu Tyr Val His His Arg Tyr Gln Glu Ser Cys Thr Pro
                885                 890                 895

Asn Thr Phe Gly Asn Asn Thr Asn Cys Val Thr Arg Asn Gly Glu Gln
            900                 905                 910

His Val Tyr Glu Asn Ser Cys Gly Asp Asn Ala Thr Cys Gly Arg Arg
        915                 920                 925

Thr Gly Tyr Gly Arg Arg Ser Arg Asp Glu Trp Asn Asp Tyr Arg Lys
    930                 935                 940

Pro His Val Tyr Asp Asn Cys Ala Asp Ala Asn Ser Ser Ser Ser Asp
945                 950                 955                 960

Ser Cys Ser Asp Ser Ser Ser Ser Ser Glu Ser Glu Ser Asp Ser Asp
                965                 970                 975

Gly Cys Cys Asp Thr Asp Ala Ser Leu Asp Ser Asp Ile Glu Asn Cys
            980                 985                 990

Tyr Gln Asn Pro Ser Lys Cys Asp  Ala Gly Cys
        995                 1000
```

<210> SEQ ID NO 7

-continued

<211> LENGTH: 163
<212> TYPE: PRT
<213> ORGANISM: Amsacta moorei entomopoxvirus

<400> SEQUENCE: 7

```
Arg Ser Ile Arg Leu Asn Ser His Lys Asp Leu Pro Gln Glu Tyr Arg
1               5                   10                  15

Tyr Val Asn Val His Phe Leu Ile Ser Tyr Thr Asn Asn Arg Lys Ser
            20                  25                  30

Val Asp Lys Glu Ile Leu Asp Ile Ile Lys Asp Lys Gln Gly Lys Ile
        35                  40                  45

Asn Val Ile Phe Asp Leu Leu Lys Ser Ser Ser Ile Glu Ser Ile His
    50                  55                  60

Asn Thr Tyr Lys Tyr Ile Glu Pro Ala Glu Asn Glu Ile Ile Phe Asp
65                  70                  75                  80

Thr Ile Arg Lys Thr Arg Met Lys Glu Met Asn Val Ser Asn Val Ile
                85                  90                  95

Ile Asn Ile Lys Leu Tyr Pro Ile Ser Tyr Cys Lys Asp Tyr Asp Arg
            100                 105                 110

Ala Thr Ile Leu Lys Gly Leu Leu Asn Lys Asp Thr Asn Ile Val Tyr
        115                 120                 125

Lys Asp Asn Thr Ala Val Ala Lys Leu Met Ile Asp Lys Asp Asn Ile
    130                 135                 140

Pro Ile Phe Ile Ile Glu Asn Asp Thr Leu Ile Tyr Ile Ala Asp Asp
145                 150                 155                 160

Tyr Tyr Glu
```

<210> SEQ ID NO 8
<211> LENGTH: 1511
<212> TYPE: DNA
<213> ORGANISM: Amsacta moorei entomopoxvirus

<400> SEQUENCE: 8

```
gaattcaagt taaatattta taaacaacaa tcatattttt ttaaagaatc taataaattt     60

tttaacattt tattattatt tgataattgt ttatttaatt cgttattgat attaacaata    120

ttatttatca ttttacctat tttttttttt ctatctacta acgaaatatc agattttgca    180

ccttcaatat cagaataata attatcatta ttttgcattt atgaataaaa atattaatat    240

gaattattat aacataatct acacacagga acatataaat cttgtccacc tatttcaatt    300

atttgatttt tattatgttt tttaattgta aaagaagcat ctttataaca aaattgacat    360

atagcttgta atttttttat tttttctact ttaggaatta attttgatat agaattaaat    420

atatttctgt taaagtcaca atttaatcca gcaacaataa cttttttttt attattagcc    480

attttatcac aaaattgttc taaatcattt tcttcaaaaa attgacactc atctatgcca    540

ataatatcat aattatctac gatattgatt tcattaatta aattatttgt tttaatgtat    600

aaatattctt tatttaatat atttccgtca tgatttatta tatttttatt tataaatcta    660

ttatctatat tatgagttat aattacacat ttttgattag ataaaatata tctattaatt    720

tttcgcatca attctgttgt tttgccagaa aacataggac caattattaa ttctatcgac    780

attttttttt attatttgat atattttttc aaaaaaaaat taatcaatga aaaaaaaata    840

aaattatcaa aatggattta ctaaattctg atataatttt aataaatatt ttaaaatatt    900

ataatttaaa aaaaataata ataaacagag ataatgttat taatattaat atattaaaaa    960

aattagttaa tttagaagaa ttgcatataa tatattatga taataatatt ttaaataata   1020
```

-continued

```
ttccagaaaa tattaaaagt ttatatattt caaatttaaa tattattaat ttaaatttta   1080

taacaaaatt aaaaaatata acatatttag atatatctta taacaaaaat agcaatataa   1140

gtaatattat actaccacat tctatagaat ttttaaattg tgaatcatgt aatataaatg   1200

actataattt tattaataat ttagtaaatt taaaaaaatt aataatatct aaaaataaat   1260

ttggtaactt taataatgtt tttcctatta gtatagttga gttaaatatg gaatcaatac   1320

aaataaaaga ttataaattt atagaaaaat taattaattt aaaaaaatta gatatatctt   1380

tcaatgttaa aaaaaataat atacatttga taaaatttcc aaaaagtata actcatttat   1440

gtgattatca atcatataaa gaaaattata attatttaaa aaatttatca aatataattg   1500

aatatgaatt c                                                        1511


<210> SEQ ID NO 9
<211> LENGTH: 66
<212> TYPE: PRT
<213> ORGANISM: Amsacta moorei entomopoxvirus

<400> SEQUENCE: 9

Met Gln Asn Asn Asp Asn Tyr Tyr Ser Asp Ile Glu Gly Ala Lys Ser
1               5                   10                  15

Asp Ile Ser Leu Val Asp Arg Lys Lys Lys Ile Gly Lys Met Ile Asn
            20                  25                  30

Asn Ile Val Asn Ile Asn Asn Glu Leu Asn Lys Gln Leu Ser Asn Asn
        35                  40                  45

Asn Lys Met Leu Lys Asn Leu Leu Asp Ser Leu Lys Lys Tyr Asp Cys
    50                  55                  60

Cys Leu
65


<210> SEQ ID NO 10
<211> LENGTH: 182
<212> TYPE: PRT
<213> ORGANISM: Amsacta moorei entomopoxvirus

<400> SEQUENCE: 10

Met Ser Ile Glu Leu Ile Ile Gly Pro Met Phe Ser Gly Lys Thr Thr
1               5                   10                  15

Glu Leu Met Arg Lys Ile Asn Arg Tyr Ile Leu Ser Asn Gln Lys Cys
            20                  25                  30

Val Ile Ile Thr His Asn Ile Asp Asn Arg Phe Ile Asn Lys Asn Ile
        35                  40                  45

Ile Asn His Asp Gly Asn Ile Leu Asn Lys Glu Tyr Leu Tyr Ile Lys
    50                  55                  60

Thr Asn Asn Leu Ile Asn Glu Ile Asn Ile Val Asp Asn Tyr Asp Ile
65                  70                  75                  80

Ile Gly Ile Asp Glu Cys Gln Phe Phe Glu Glu Asn Asp Leu Glu Gln
                85                  90                  95

Phe Cys Asp Lys Met Ala Asn Asn Lys Lys Lys Val Ile Val Ala Gly
            100                 105                 110

Leu Asn Cys Asp Phe Asn Arg Asn Ile Phe Asn Ser Ile Ser Lys Leu
        115                 120                 125

Ile Pro Lys Val Glu Lys Ile Lys Lys Leu Gln Ala Ile Cys Gln Phe
    130                 135                 140

Cys Tyr Lys Asp Ala Ser Phe Thr Ile Lys Lys His Asn Lys Asn Gln
145                 150                 155                 160
```

-continued

```
Ile Ile Glu Ile Gly Gly Gln Asp Leu Tyr Val Pro Val Cys Arg Leu
                165                 170                 175

Cys Tyr Asn Asn Ser Tyr
            180


<210> SEQ ID NO 11
<211> LENGTH: 220
<212> TYPE: PRT
<213> ORGANISM: Amsacta moorei entomopoxvirus

<400> SEQUENCE: 11

Met Asp Leu Leu Asn Ser Asp Ile Ile Leu Ile Asn Ile Leu Lys Tyr
1               5                   10                  15

Tyr Asn Leu Lys Lys Ile Ile Ile Asn Arg Asp Asn Val Ile Asn Ile
            20                  25                  30

Asn Ile Leu Lys Lys Leu Val Asn Leu Glu Glu Leu His Ile Ile Tyr
        35                  40                  45

Tyr Asp Asn Asn Ile Leu Asn Asn Ile Pro Glu Asn Ile Lys Ser Leu
    50                  55                  60

Tyr Ile Ser Asn Leu Asn Ile Ile Asn Leu Asn Phe Ile Thr Lys Leu
65                  70                  75                  80

Lys Asn Ile Thr Tyr Leu Asp Ile Ser Tyr Asn Lys Asn Ser Asn Ile
                85                  90                  95

Ser Asn Ile Ile Leu Pro His Ser Ile Glu Phe Leu Asn Cys Glu Ser
            100                 105                 110

Cys Asn Ile Asn Asp Tyr Asn Phe Ile Asn Asn Leu Val Asn Leu Lys
        115                 120                 125

Lys Leu Ile Ile Ser Lys Asn Lys Phe Gly Asn Phe Asn Asn Val Phe
    130                 135                 140

Pro Ile Ser Ile Val Glu Leu Asn Met Glu Ser Ile Gln Ile Lys Asp
145                 150                 155                 160

Tyr Lys Phe Ile Glu Lys Leu Ile Asn Leu Lys Lys Leu Asp Ile Ser
                165                 170                 175

Phe Asn Val Lys Lys Asn Asn Ile His Leu Ile Lys Phe Pro Lys Ser
            180                 185                 190

Ile Thr His Leu Cys Asp Tyr Gln Ser Tyr Lys Glu Asn Tyr Asn Tyr
        195                 200                 205

Leu Lys Asn Leu Ser Asn Ile Ile Glu Tyr Glu Phe
    210                 215                 220


<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide RM58.
<221> NAME/KEY: misc_feature
<222> LOCATION: (6)..(6)
<223> OTHER INFORMATION: N can be A, G, C, or T.
<221> NAME/KEY: misc_feature
<222> LOCATION: (12)..(12)
<223> OTHER INFORMATION: N can be A, G, C, or T.

<400> SEQUENCE: 12

gargtngayc cngartaygt                                                  20


<210> SEQ ID NO 13
<211> LENGTH: 20
<212> TYPE: DNA
```

-continued

<213> ORGANISM: Artificial Sequence
<220> FEATURE:
<223> OTHER INFORMATION: Synthetic oligonucleotide RM82.

<400> SEQUENCE: 13
tttcaaatta actggcaacc 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide RM83.

<400> SEQUENCE: 14
gggatggatt ttagattgcg 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide RM92.

<400> SEQUENCE: 15
gcctggttgg gtaacacctc 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide RM118.

<400> SEQUENCE: 16
ctgctagatt atctactccg 20

<210> SEQ ID NO 17
<211> LENGTH: 35
<212> TYPE: DNA
<213> ORGANISM: Artificial Sequence
<220> FEATURE:
<223> OTHER INFORMATION: Synthetic oligonucleotide RM165.

<400> SEQUENCE: 17
gttcgaaaca agtattttca tcttttaaat aaatc 35

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide RM03.

<400> SEQUENCE: 18
gaygarggrg grcarttytt 20

<210> SEQ ID NO 19
<211> LENGTH: 17
<212> TYPE: DNA
<213> ORGANISM: Artificial Sequence
<220> FEATURE:
<223> OTHER INFORMATION: Synthetic oligonucleotide RM04.
<221> NAME/KEY: misc_feature
<222> LOCATION: (3)..(3)
<223> OTHER INFORMATION: N = A, C, G, or T.
<221> NAME/KEY: misc_feature -continued
<222> LOCATION: (15)..(15)
<223> OTHER INFORMATION: N = A, C, G, or T.

<400> SEQUENCE: 19
ggncccatgt tytcngg 17

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide RM129.

<400> SEQUENCE: 20
ggtgcaaaat ctgatatttc 20

<210> SEQ ID NO 21
<211> LENGTH: 3012
<212> TYPE: DNA
<213> ORGANISM: Amsacta moorei entomopoxvirus

<400> SEQUENCE: 21
atgagtaacg tacctttagc aaccaaaaca ataagaaaat tatcaaatcg aaaatatgaa 60
ataaagattt atttaaaaga tgaaaatact tgtttcgaac gtgtagtaga tatggtagtt 120
ccattatatg atgtgtgtaa tgaaacttct ggtgttactt tagaatcatg tagtccaaat 180
atagaagtaa ttgaattaga caatactcat gttagaatca aagttcacgg cgatacatta 240
aaagaaatgt gttttgaatt attgttcccg tgtaatgtaa acgaagccca agtatggaaa 300
tatgtaagtc gattattgct agataatgta tcacataatg acgtaaaata taaattagct 360
aattttagac tgactcttaa tggaaaacat ttaaaattaa aagaaatcga tcaaccgcta 420
tttatttatt ttgtcgatga tttgggaaat tatggattaa ttactaagga aaatattcaa 480
aataataatt tacaagttaa caaagatgca tcatttatta ctatatttcc acaatatgcg 540
tatatttgtt taggtagaaa agtatattta aatgaaaaag taacttttga tgtaactaca 600
gatgcaacta atattacttt agattttaat aaatctgtta atatcgcagt atcattcctt 660
gatatatatt acgaagttaa taataatgaa caaaaagatt tattaaaaga tttacttaag 720
agatacggtg aatttgaagt ctataacgca gatactggat taatttatgc taaaaatcta 780
agtattaaaa attatgatac tgtgattcaa gtagaaaggt tgccagttaa tttgaaagtt 840
agagcatata ctaaggatga aaatggtcgc aatctatgtt tgatgaaaat aacatctagt 900
acagaagtag accccgagta tgtaactagt aataatgctt tattgggtac gctcagagta 960
tataaaaagt ttgataaatc tcatttaaaa attgtaatgc ataacagagg aagtggtaat 1020
gtatttccat taagatcatt atatctggaa ttgtctaatg taaaaggata tccagttaaa 1080
gcatctgata cttcgagatt agatgttggt atttacaaat taaataaaat ttatgtagat 1140
aacgacgaaa ataaaattat attggaagaa attgaagcag aatatagatg cggaagacaa 1200
gtattccacg aacgtgtaaa acttaataaa caccaatgta aatatactcc caaatgtcca 1260
ttccaatttg ttgtaaacag cccagatact acgattcact tatatggtat ttctaatgtt 1320
tgtttaaaac ctaaagtacc caaaaattta agactttggg gatggatttt agattgcgat 1380
acttctagat ttattaaaca tatggctgat ggatctgatg atttagatct tgacgttagg 1440
cttaatagaa atgatatatg tttaaaacaa gccataaaac aacattatac taatgtaatt 1500
atattagagt acgcaaatac atatccaaat tgcacattat cattgggtaa taatagattt 1560

-continued

```
aataatgtat ttgatatgaa tgataacaaa actatatctg agtatactaa ctttacaaaa   1620
agtagacaag accttaataa catgtcatgt atattaggaa taaacatagg taattccgta   1680
aatattagta gtttgcctgg ttgggtaaca cctcacgaag ctaaaattct aagatctggt   1740
tgtgctagag ttagagaatt ttgtaaatca ttctgtgatc tttctaataa gagattctat   1800
gctatggcta gagatctcgt aagtttacta tttatgtgta actatgttaa tattgaaatt   1860
aacgaagcag tatgcgaata tcctggatat gtcatattat tcgcaagagc tattaaagta   1920
attaatgatt tattattaat taacggagta gataatctag caggatattc aatttcctta   1980
cctatacatt atggatctac tgaaaagact ctaccaaatg aaaagtatgg tggtgttgat   2040
aagaaattta aatatctatt cttaaagaat aaactaaaag atttaatgcg tgatgctgat   2100
tttgtccaac ctccattata tatttctact tactttagaa ctttattgga tgctccacca   2160
actgataatt atgaaaaata tttggttgat tcgtccgtac aatcacaaga tgttctacag   2220
ggtctgttga atacatgtaa tactattgat actaatgcta gagttgcatc aagtgttatt   2280
ggatatgttt atgaaccatg cggaacatca gaacataaaa ttggttcaga agcattgtgt   2340
aaaatggcta aagaagcatc tagattagga aatctaggtt tagtaaatcg tattaatgaa   2400
agtaattaca acaaatgtaa taaatatggt tatagaggag tatacgaaaa taacaaacta   2460
aaaacaaaat attatagaga aatatttgat tgtaatccta ataataataa tgaattaata   2520
tccagatatg gatatagaat aatggattta cataaaattg gagaaatttt tgcaaattac   2580
gatgaaagtg aatctccttg cgaacgaaga tgtcattact tggaagatag aggtctttta   2640
tatggtcctg aatatgtaca tcacagatat caagaatcat gtacgcctaa tacgtttgga   2700
aataacacaa attgtgtaac aagaaatggt gaacaacacg tatacgaaaa tagttgtgga   2760
gataatgcaa catgtggaag aagaacagga tatggaagaa gaagtaggga tgaatggaat   2820
gactatagaa aaccccacgt ttatgacaat tgtgccgatg caaatagttc atcttcagat   2880
agctgttcag acagtagtag tagtagtgaa tctgaatctg attcagatgg atgttgcgac   2940
acagatgcta gtttagattc tgatattgaa aattgttatc aaaatccatc aaaatgtgat   3000
gcaggatgct aa                                                        3012
```

<210> SEQ ID NO 22
<211> LENGTH: 419
<212> TYPE: DNA
<213> ORGANISM: Amsacta moorei entomopoxvirus

<400> SEQUENCE: 22

```
tcaactaata ataatatatt ttatgcagtt tcaacttttg gatttttaag tacagaaagt     60
actggtatta atttaacata tacaaattct agagattgta ttatagattt attttctaga    120
attataaaaa tagtatatga tccttgtact gtcgaaacat ctaacgattg tagattatta    180
agattattga tggccaatac atcataaata cattataata ttattataat atcaatcata    240
atttttatat atattttatc taaaaggact ttttattttt tatatattaa taataataaa    300
tgagtaacgt acctttagca accaaaacaa taagaaaatt atcaaatcga aaatatgaaa    360
taaagattta tttaaaagat gaaaatactt gtttcgaacg tgtagtagat atggtagtt     419
```

<210> SEQ ID NO 23
<211> LENGTH: 678
<212> TYPE: DNA
<213> ORGANISM: Amsacta moorei entomopoxvirus

<400> SEQUENCE: 23

-continued

```
atgtttctag tttatttcaa tacattttta ataataattt tattatttgg tattataggt     60

atttatatat taacatttgt gtttaatata gattttttaa taaataataa taaaatatat    120

atattatcat ataacgcaac taatataaac aatataaata atttaaattt atacgattat    180

tcagatatta tatttttgac aaattttaac ataaataata atcttttagt aacacaagct    240

aataatttac aagatatacc aatatttaat gtaaataata ttatatctaa tcaatataat    300

ttttattcag cgtctagtaa taatgtaaat atattattag gattaagaaa aacattaaat    360

ataaatagaa atccattttt attatttaga aatacatctc tagctatagt tttcaataat    420

aatgaaactt ttcactgtta tataagttca aatcaaaata gtgatgtatt agatatagta    480

tcacatatag aatttatgaa atctagatat aataaatatg taattatagg agaaataccc    540

gtaaataata atatatctat taataatata ttaaataatt ttgctattat aactaatgtg    600

agattaatag ataaatataa ctctataata tcatttttaa atatcaacgt aggaacactt    660

tttgtcataa atccataa                                                  678
```

<210> SEQ ID NO 24
<211> LENGTH: 486
<212> TYPE: DNA
<213> ORGANISM: Amsacta moorei entomopoxvirus

<400> SEQUENCE: 24

```
atgtcaatat ttatctacta tattttcaac aatagatttt atatatataa aagaatgaat     60

actgtacaaa ttttagttgt catattaata acaacagcat tatcttttct agtttttcaa    120

ttatggtatt atgccgaaaa ttacgaatat atattaagat ataatgatac atattcaaat    180

ttacaatttg cgagaagcgc aaatataaat tttgatgatt taactgtttt tgatcccaac    240

gataatgttt ttaatgttga agaaaaatgg cgctgtgctt caactaataa taatatattt    300

tatgcagttt caacttttgg atttttaagt acagaaagta ctggtattaa tttaacatat    360

acaaattcta gagattgtat tatagattta ttttctagaa ttataaaaat agtatatgat    420

ccttgtactg tcgaaacatc taacgattgt agattattaa gattattgat ggccaataca    480

tcataa                                                               486
```

<210> SEQ ID NO 25
<211> LENGTH: 1395
<212> TYPE: DNA
<213> ORGANISM: Amsacta moorei entomopoxvirus

<400> SEQUENCE: 25

```
ttaaatatta gattctaaac tattcttctc attatcaata taactatcat aatcattttt     60

tattttacta catacattca taattctatt actatttttt ttatacatat ctattaattc    120

cataaacttt ttattttttta tattaaatat ttctaatgta tttttaaatt cgtcaatact    180

attaatatca tatctagaaa taaataatgc acctctataa ctactagcca ataaatcacc    240

aataaaactc atagaataat ataatttttt aaattcaaat ttagatttta tgttgaaata    300

aactatataa tataaaaata ttatattaaa cataccacaa tcgggactat catattgtaa    360

ttcaaaagta ttaaaaaagt aataatttac atttttaaat atatcattta aatattctga    420

tagtacatca atgtataaat aagcataatt agtattagga gtactattgt agtgtttatg    480

gctttttata gtcatatcag attcaataaa catatatttt ttattttgtt ttataagttc    540

tggtatataa ccactactat taaaaaagta tgcagctttt ttatctttat caaagtgttt    600
```

-continued atctattacg caacaagtaa aatgatcatt ataaattata ggaaacataa aaaatctttt 660
tttatcattc attaaaaaaa attttactct atcttcaagt ttatagcatc tcatagatga 720
agctactgta gcaatatttt tatcagtttt ttcaaataaa atcaaatgaa aataatcata 780
atctgtatta atcatagtta atggatatat acaattatat atatctcccg aacttaacca 840
tgtagattta tcatgttttc ttgggtaagc tttaggttta ggattaaatc ccaaaggcgg 900
tattcctatt tgagcatcca aatcatcata aattgtggca aatgtagaaa aatctcttgt 960
tttggataat tctgatttta gaaaagactt tctcatatat actaatggaa tgcctttata 1020
ttttttagat gtaataaaag tattaatatt tatattttta tcttgtaaat atttttttat 1080
agtccaaaat agaaaaaatt ttcttttaat attattttca aaattaatat tattaatatg 1140
atttggatct aaaactaatt cattatataa tatttccaag tattttatag gtataaatgt 1200
tactttacct cttgtttcat catcatcatc tattttttct aatatagcta tatttgcatt 1260
agtattatat ttaataggat ttataaaata taccatatta tctattttac taaaaaataa 1320
catagacata aaattaatac cagattctgg catttttaaa tttttatttg gaaatcttct 1380
aattttatta ttcat 1395

<210> SEQ ID NO 26
<211> LENGTH: 237
<212> TYPE: DNA
<213> ORGANISM: Amsacta moorei entomopoxvirus

<400> SEQUENCE: 26
ttattttttt tttttgcttt taggtataat tttaccttct aaacgtttat ctccccaaac 60
atctacagta gatggtttat tagattctgt gttatacaca tctgctggat ttgcggcatt 120
tgtatccaaa ccataatatc caggtctata attatcttta aaaacttggg attgagatac 180
ttcttcagtt tttaaattat taaaatatcc aagattattt ttttttgatg aagacat 237

<210> SEQ ID NO 27
<211> LENGTH: 492
<212> TYPE: DNA
<213> ORGANISM: Amsacta moorei entomopoxvirus

<400> SEQUENCE: 27
ctattcataa taatcatctg ctatatatat taatgtatca ttctctatta taaatatagg 60
tatattgtct ttatcaatca ttaattttgc tacagctgta ttatctttat atactatatt 120
tgtgtctttg tttaataaac cttttaatat agtggctcta tcataatctt tacaatatga 180
tatgggatat aattttatat taataataac attagatacg ttcatttctt tcattctagt 240
tttacgtatt gtgtcaaaaa ttatttcatt ttctgctggt tctatatatt tatatgtgtt 300
atgaatagat tcgatagatg atgattttaa taaatcaaat ataacattta ttttaccttg 360
tttatctttt ataatatcta atatttcttt atctacagat tttctgttgt tggtatatga 420
tattaaaaaa tgaacgttaa catatctata ttcttgtggt aaatctttat gagaatttaa 480
tcttatagat ct 492

<210> SEQ ID NO 28
<211> LENGTH: 549
<212> TYPE: DNA
<213> ORGANISM: Amsacta moorei entomopoxvirus

<400> SEQUENCE: 28
ttaatatgaa ttattataac ataatctaca cacaggaaca tataaatctt gtccacctat 60

-continued ttcaattatt tgatttttat tatgtttttt aattgtaaaa gaagcatctt tataacaaaa 120
ttgacatata gcttgtaatt tttttatttt ttctacttta ggaattaatt ttgatataga 180
attaaatata tttctgttaa agtcacaatt taatccagca acaataactt tttttttatt 240
attagccatt ttatcacaaa attgttctaa atcattttct tcaaaaaatt gacactcatc 300
tatgccaata atatcataat tatctacgat attgatttca ttaattaaat tatttgtttt 360
aatgtataaa tattctttat ttaatatatt tccgtcatga tttattatat ttttatttat 420
aaatctatta tctatattat gagttataat tacacatttt tgattagata aaatatatct 480
attaattttt cgcatcaatt ctgttgtttt gccagaaaac ataggaccaa ttattaattc 540
tatcgacat 549

<210> SEQ ID NO 29
<211> LENGTH: 69
<212> TYPE: DNA
<213> ORGANISM: Amsacta moorei entomopoxvirus

<400> SEQUENCE: 29 tttttttat tatttgatat attttttcaa aaaaaaatta atcaatgaaa aaaaaataaa 60
attatcaaa 69

<210> SEQ ID NO 30
<211> LENGTH: 141
<212> TYPE: DNA
<213> ORGANISM: Amsacta moorei entomopoxvirus

<400> SEQUENCE: 30
aaacatagga ccaattatta attctatcga catttttttt tattatttga tatatttttt 60
caaaaaaaaa ttaatcaatg aaaaaaaaat aaaattatca aaatggattt actaaattct 120
gatataattt taataaatat t 141

<210> SEQ ID NO 31
<211> LENGTH: 201
<212> TYPE: DNA
<213> ORGANISM: Amsacta moorei entomopoxvirus

<400> SEQUENCE: 31
ttataaacaa caatcatatt tttttaaaga atctaataaa ttttttaaca ttttattatt 60
atttgataat tgtttattta attcgttatt gatattaaca atattattta tcattttacc 120
tatttttttt tttctatcta ctaacgaaat atcagatttt gcaccttcaa tatcagaata 180
ataattatca ttattttgca t 201

<210> SEQ ID NO 32
<211> LENGTH: 660
<212> TYPE: DNA
<213> ORGANISM: Amsacta moorei entomopoxvirus

<400> SEQUENCE: 32
atggatttac taaattctga tataatttta ataaatattt taaaatatta taatttaaaa 60
aaaataataa taaacagaga taatgttatt aatattaata tattaaaaaa attagttaat 120
ttagaagaat tgcatataat atattatgat aataatattt taaataatat tccagaaaat 180
attaaaagtt tatatatttc aaatttaaat attattaatt taaattttat aacaaaatta 240
aaaaatataa catatttaga tatatcttat aacaaaaata gcaatataag taatattata 300

-continued

```
ctaccacatt ctatagaatt tttaaattgt gaatcatgta atataaatga ctataatttt    360

attaataatt tagtaaattt aaaaaaatta ataatatcta aaaataaatt tggtaacttt    420

aataatgttt ttcctattag tatagttgag ttaaatatgg aatcaataca aataaaagat    480

tataaattta tagaaaaatt aattaattta aaaaaattag atatatcttt caatgttaaa    540

aaaaataata tacatttgat aaaatttcca aaaagtataa ctcatttatg tgattatcaa    600

tcatataaag aaaattataa ttatttaaaa aatttatcaa atataattga atatgaattc    660
```

<210> SEQ ID NO 33
<211> LENGTH: 3907
<212> TYPE: DNA
<213> ORGANISM: Amsacta moorei entomopoxvirus

<400> SEQUENCE: 33

```
ttctaaacgt ttatctcccc aaacatctac agtagatggt ttattagatt ctgtgttata     60

cacatctgct ggatttgcgg catttgtatc caaaccataa tatccaggtc tataattatc    120

tttaaaaact tgggattgag atacttcttc agtttttaaa ttattaaaat atccaagatt    180

attttttttt gatgaagaca taattgatat tataatactt tatagatatg tcaatattta    240

tctactatat tttcaacaat agattttata tatataaaag aatgaatact gtacaaattt    300

tagttgtcat attaataaca acagcattat cttttctagt ttttcaatta tggtattatg    360

ccgaaaatta cgaatatata ttaagatata atgatacata ttcaaattta caatttgcga    420

gaagcgcaaa tataaatttt gatgatttaa ctgtttttga tcccaacgat aatgttttta    480

atgttgaaga aaaatggcgc tgtgcttcaa ctaataataa tatattttat gcagtttcaa    540

cttttggatt tttaagtaca gaaagtactg gtattaattt aacatataca aattctagag    600

attgtattat agatttattt tctagaatta taaaaatagt atatgatcct tgtactgtcg    660

aaacatctaa cgattgtaga ttattaagat tattgatggc caatacatca taaatacatt    720

ataatattat tataatatca atcataattt ttatatatat tttatctaaa aggacttttt    780

atttttttata tattaataat aataaatgag taacgtacct ttagcaacca aaacaataag    840

aaaattatca aatcgaaaat atgaaataaa gatttattta aaagatgaaa atacttgttt    900

cgaacgtgta gtagatatgg tagttccatt atatgatgtg tgtaatgaaa cttctggtgt    960

tactttagaa tcatgtagtc caaatataga agtaattgaa ttagacaata ctcatgttag   1020

aatcaaagtt cacggcgata cattaaaaga aatgtgtttt gaattattgt tcccgtgtaa   1080

tgtaaacgaa gcccaagtat ggaaatatgt aagtcgatta ttgctagata atgtatcaca   1140

taatgacgta aaatataaat tagctaattt tagactgact cttaatggaa aacatttaaa   1200

attaaaagaa atcgatcaac cgctatttat ttattttgtc gatgatttgg gaaattatgg   1260

attaattact aaggaaaata ttcaaaataa taatttacaa gttaacaaag atgcatcatt   1320

tattactata tttccacaat atgcgtatat ttgtttaggt agaaaagtat atttaaatga   1380

aaaagtaact tttgatgtaa ctacagatgc aactaatatt actttagatt ttaataaatc   1440

tgttaatatc gcagtatcat tccttgatat atattacgaa gttaataata atgaacaaaa   1500

agatttatta aaagatttac ttaagagata cggtgaattt gaagtctata acgcagatac   1560

tggattaatt tatgctaaaa atctaagtat taaaaattat gatactgtga ttcaagtaga   1620

aaggttgcca gttaatttga aagttagagc atatactaag gatgaaaatg gtcgcaatct   1680

atgtttgatg aaaataacat ctagtacaga agtagacccc gagtatgtaa ctagtaataa   1740

tgctttattg ggtacgctca gagtatataa aaagtttgat aaatctcatt taaaaattgt   1800
```

-continued aatgcataac agaggaagtg gtaatgtatt tccattaaga tcattatatc tggaattgtc 1860
taatgtaaaa ggatatccag ttaaagcatc tgatacttcg agattagatg ttggtattta 1920
caaattaaat aaaatttatg tagataacga cgaaaataaa attatattgg aagaaattga 1980
agcagaatat agatgcggaa gacaagtatt ccacgaacgt gtaaaactta ataaacacca 2040
atgtaaatat actcccaaat gtccattcca atttgttgta aacagcccag atactacgat 2100
tcacttatat ggtatttcta atgtttgttt aaaacctaaa gtacccaaaa atttaagact 2160
ttggggatgg attttagatt gcgatacttc tagatttatt aaacatatgg ctgatggatc 2220
tgatgattta gatcttgacg ttaggcttaa tagaaatgat atatgtttaa aacaagccat 2280
aaaacaacat tatactaatg taattatatt agagtacgca aatacatatc caaattgcac 2340
attatcattg ggtaataata gatttaataa tgtatttgat atgaatgata acaaaactat 2400
atctgagtat actaacttta caaaaagtag acaagacctt aataacatgt catgtatatt 2460
aggaataaac ataggtaatt ccgtaaatat tagtagtttg cctggttggg taacacctca 2520
cgaagctaaa attctaagat ctggttgtgc tagagttaga gaattttgta aatcattctg 2580
tgatctttct aataagagat tctatgctat ggctagagat ctcgtaagtt tactatttat 2640
gtgtaactat gttaatattg aaattaacga agcagtatgc gaatatcctg gatatgtcat 2700
attattcgca agagctatta aagtaattaa tgatttatta ttaattaacg gagtagataa 2760
tctagcagga tattcaattt ccttacctat acattatgga tctactgaaa agactctacc 2820
aaatgaaaag tatggtggtg ttgataagaa atttaaatat ctattcttaa agaataaact 2880
aaaagattta atgcgtgatg ctgattttgt ccaacctcca ttatatattt ctacttactt 2940
tagaacttta ttggatgctc caccaactga taattatgaa aaatatttgg ttgattcgtc 3000
cgtacaatca caagatgttc tacagggtct gttgaataca tgtaatacta ttgatactaa 3060
tgctagagtt gcatcaagtg ttattggata tgtttatgaa ccatgcggaa catcagaaca 3120
taaaattggt tcagaagcat tgtgtaaaat ggctaaagaa gcatctagat taggaaatct 3180
aggtttagta aatcgtatta atgaaagtaa ttacaacaaa tgtaataaat atggttatag 3240
aggagtatac gaaaataaca aactaaaaac aaaatattat agagaaatat ttgattgtaa 3300
tcctaataat aataatgaat taatatccag atatggatat agaataatgg atttacataa 3360
aattggagaa atttttgcaa attacgatga aagtgaatct ccttgcgaac gaagatgtca 3420
ttacttggaa gatagaggtc ttttatatgg tcctgaatat gtacatcaca gatatcaaga 3480
atcatgtacg cctaatacgt ttggaaataa cacaaattgt gtaacaagaa atggtgaaca 3540
acacgtatac gaaaatagtt gtggagataa tgcaacatgt ggaagaagaa caggatatgg 3600
aagaagaagt agggatgaat ggaatgacta tagaaaaccc cacgtttatg acaattgtgc 3660
cgatgcaaat agttcatctt cagatagctg ttcagacagt agtagtagta gtgaatctga 3720
atctgattca gatggatgtt gcgacacaga tgctagttta gattctgata ttgaaaattg 3780
ttatcaaaat ccatcaaaat gtgatgcagg atgctaaatg aaatttaata ttatataata 3840
ttaacttaca agttataaaa atcattaaaa tgattttta aaatgatatt atcgatagtt 3900
gtgataa 3907

<210> SEQ ID NO 34
<211> LENGTH: 25
<212> TYPE: PRT
<213> ORGANISM: Amsacta moorei entomopoxvirus
<220> FEATURE:

-continued

<221> NAME/KEY: MISC_FEATURE
<222> LOCATION: (3)..(3)
<223> OTHER INFORMATION: X = Asn or Arg.
<221> NAME/KEY: MISC_FEATURE
<222> LOCATION: (12)..(12)
<223> OTHER INFORMATION: X = Asn or Arg.
<221> NAME/KEY: MISC_FEATURE
<222> LOCATION: (13)..(13)
<223> OTHER INFORMATION: X = Unknown amino acid.
<221> NAME/KEY: MISC_FEATURE
<222> LOCATION: (24)..(24)
<223> OTHER INFORMATION: X = Unknown amino acid.

<400> SEQUENCE: 34

```
Met Ala Xaa Asp Leu Val Ser Leu Leu Phe Met Xaa Xaa Tyr Val Asn
1               5                   10                  15

Ile Glu Ile Asn Glu Ala Val Xaa Glu
            20                  25
```

<210> SEQ ID NO 35
<211> LENGTH: 17
<212> TYPE: PRT
<213> ORGANISM: Amsacta moorei entomopoxvirus
<220> FEATURE:
<221> NAME/KEY: MISC_FEATURE
<222> LOCATION: (15)..(15)
<223> OTHER INFORMATION: X = Thr or Ile.

<400> SEQUENCE: 35

```
Met Lys Ile Thr Ser Ser Thr Glu Val Asp Pro Glu Tyr Val Xaa Ser
1               5                   10                  15

Asn
```

<210> SEQ ID NO 36
<211> LENGTH: 8
<212> TYPE: PRT
<213> ORGANISM: Amsacta moorei entomopoxvirus

<400> SEQUENCE: 36

```
Asn Ala Leu Phe Phe Asn Val Phe
1               5
```

<210> SEQ ID NO 37
<211> LENGTH: 7
<212> TYPE: PRT
<213> ORGANISM: Artificial Sequence
<220> FEATURE:
<223> OTHER INFORMATION: Peptide encoded by RM58.

<400> SEQUENCE: 37

```
Glu Val Asp Pro Glu Tyr Val
1               5
```

<210> SEQ ID NO 38
<211> LENGTH: 74
<212> TYPE: DNA
<213> ORGANISM: Amsacta moorei entomopoxvirus

<400> SEQUENCE: 38

```
atggctagag atctcgtaag tttactattt atgtgtaact atgttaatat tgaaattaac     60

gaagcagtat gcga                                                       74
```

<210> SEQ ID NO 39
<211> LENGTH: 51
<212> TYPE: DNA
<213> ORGANISM: Amsacta moorei entomopoxvirus -continued

<400> SEQUENCE: 39
atgaaaataa catctagtac agaagtagac cccgagtatg taactagtaa t 51

<210> SEQ ID NO 40
<211> LENGTH: 24
<212> TYPE: DNA
<213> ORGANISM: Amsacta moorei entomopoxvirus

<400> SEQUENCE: 40
aataatagat ttaataatgt attt 24

<210> SEQ ID NO 41
<211> LENGTH: 1689
<212> TYPE: DNA
<213> ORGANISM: Amsacta moorei entomopoxvirus

<400> SEQUENCE: 41
tcctattatt tgttttaatt ctgattcatt ccacggcata tctaatataa ttatatcatt 60
aatacatttg aatgatatgc cttcagatcc agcgtaagaa aatatgcaaa cttttacttt 120
tttaccatta ttattttcat aattattata ttcgtttaat tcattatctc tagtttttaa 180
agttttgcta gaatattcaa tataagaaat attaaaacaa ttaaaataac attttaaact 240
tgatattcct tcaaaattaa ctaaaggttc aaatattaat acttttcctc tcgaatttaa 300
aattatttta caagtttcta tatatttaca cgaatattga tataatatat tataattatt 360
tatatcagtg attggtaaat tagtttttat ttttatatta tcatttttaa aactttcaat 420
aaaagattca gagaaattaa tattttttgt aaactcggaa aattcagcaa gttttctttt 480
aatcatatca ttatattcta tattatctaa atctcctttt attttaagat cataaaaagc 540
aaatgaagat attaatcttc tcatagtttt taaaccacct aattcagttt tataatcata 600
tttttctgcc atattatata atttagattg ctcatctgac ataattatat tatgataaaa 660
tatatttttt tttgcatatc catctatata atttgtttct gttaaactat ctgcttctat 720
taatctttta taagaacata tagctaataa tgtttctctt aattccttaa aattaattaa 780
ctttccatta tttatatatt cttcttttat attcataaca tttggtctaa gtaaacctat 840
taaattatta aattcagaaa tattattagt tactggagta gcggacatac ataatatttt 900
attattttcg aaatttgcta attttattaa ttttttataa ataggagtaa aatttctttc 960
gttattatct tttttaacag ttcttgatat taatttatga acttcgtcta ttattattag 1020
taatctactt tttttattaa gagaactttc tatagatcta tatatattat taaatttatc 1080
taaactagat gacgaatcat aatatataaa ttttatatta ctggtatctg atatatatga 1140
tcttatagta tttaaccaag gatctatgta taatgatttt ttaataaata ttaaaattat 1200
ccatcttgga aataattctt ttatatattt tataatatac acagcagtta atgtttttcc 1260
cataccagta tcccaaaata ataacatact attcaaattt tttaatccta tgaatattct 1320
acttacaaaa tattgataat cttgtaatgt aatttcagta tttgtaatat tattcataat 1380
tttattaggc aaatgttgtg ttttatcaag tgcataattt atatgtttac caacaataga 1440
atctaatgca aacatttagt tatataaaaa ataatattta tattaactta agatgtttca 1500
ttaattttat gtctgtgatg tggagttaaa acccaagata ttgatatatc tatatcatta 1560
attcttcttt tgaatctatg tctatcaatc gcaaatttat cccagtataa ttttcgagtt 1620
tgttttgcag catataacca aacatacata atgtggagtt ttggtggttc ggatgaaaag 1680

-continued

```
cgtactttt                                                         1689

<210> SEQ ID NO 42
<211> LENGTH: 485
<212> TYPE: PRT
<213> ORGANISM: Amsacta moorei entomopoxvirus

<400> SEQUENCE: 42

Met Phe Ala Leu Asp Ser Ile Val Gly Lys His Ile Asn Tyr Ala Leu
1               5                   10                  15

Asp Lys Thr Gln His Leu Pro Asn Lys Ile Met Asn Asn Ile Thr Asn
            20                  25                  30

Thr Glu Ile Thr Leu Gln Asp Tyr Gln Tyr Phe Val Ser Arg Ile Phe
        35                  40                  45

Ile Gly Leu Lys Asn Leu Asn Ser Met Leu Leu Phe Trp Asp Thr Gly
    50                  55                  60

Met Gly Lys Thr Leu Thr Ala Val Tyr Ile Ile Lys Tyr Ile Lys Glu
65                  70                  75                  80

Leu Phe Pro Arg Trp Ile Ile Leu Ile Phe Ile Lys Lys Ser Leu Tyr
                85                  90                  95

Ile Asp Pro Trp Leu Asn Thr Ile Arg Ser Tyr Ile Ser Asp Thr Ser
            100                 105                 110

Asn Ile Lys Phe Ile Tyr Tyr Asp Ser Ser Ser Ser Leu Asp Lys Phe
        115                 120                 125

Asn Asn Ile Tyr Arg Ser Ile Glu Ser Ser Leu Asn Lys Lys Ser Arg
    130                 135                 140

Leu Leu Ile Ile Ile Asp Glu Val His Lys Leu Ile Ser Arg Thr Val
145                 150                 155                 160

Lys Lys Asp Asn Asn Glu Arg Asn Phe Thr Pro Ile Tyr Lys Lys Leu
                165                 170                 175

Ile Lys Leu Ala Asn Phe Glu Asn Asn Lys Ile Leu Cys Met Ser Ala
            180                 185                 190

Thr Pro Val Thr Asn Asn Ile Ser Glu Phe Asn Asn Leu Ile Gly Leu
        195                 200                 205

Leu Arg Pro Asn Val Met Asn Ile Lys Glu Glu Tyr Ile Asn Asn Gly
    210                 215                 220

Lys Leu Ile Asn Phe Lys Glu Leu Arg Glu Thr Leu Leu Ala Ile Cys
225                 230                 235                 240

Ser Tyr Lys Arg Leu Ile Glu Ala Asp Ser Leu Thr Glu Thr Asn Tyr
                245                 250                 255

Ile Asp Gly Tyr Ala Lys Lys Asn Ile Phe Tyr His Asn Ile Ile Met
            260                 265                 270

Ser Asp Glu Gln Ser Lys Leu Tyr Asn Met Ala Glu Lys Tyr Asp Tyr
        275                 280                 285

Lys Thr Glu Leu Gly Gly Leu Lys Thr Met Arg Arg Leu Ile Ser Ser
    290                 295                 300

Phe Ala Phe Tyr Asp Leu Lys Ile Lys Gly Asp Leu Asp Asn Ile Glu
305                 310                 315                 320

Tyr Asn Asp Met Ile Lys Arg Lys Leu Ala Glu Phe Ser Glu Phe Thr
                325                 330                 335

Lys Asn Ile Asn Phe Ser Glu Ser Phe Ile Glu Ser Phe Lys Asn Asp
            340                 345                 350

Asn Ile Lys Ile Lys Thr Asn Leu Pro Ile Thr Asp Ile Asn Asn Tyr
        355                 360                 365
```

-continued

```
Asn Ile Leu Tyr Gln Tyr Ser Cys Lys Tyr Ile Glu Thr Cys Lys Ile
    370                 375                 380

Ile Leu Asn Ser Arg Gly Lys Val Leu Ile Phe Glu Pro Leu Val Asn
385                 390                 395                 400

Phe Glu Gly Ile Ser Ser Leu Lys Cys Tyr Phe Asn Cys Phe Asn Ile
                405                 410                 415

Ser Tyr Ile Glu Tyr Ser Ser Lys Thr Leu Lys Thr Arg Asp Asn Glu
            420                 425                 430

Leu Asn Glu Tyr Asn Asn Tyr Glu Asn Asn Asn Gly Lys Lys Val Lys
        435                 440                 445

Val Cys Ile Phe Ser Tyr Ala Gly Ser Glu Gly Ile Ser Phe Lys Cys
    450                 455                 460

Ile Asn Asp Ile Ile Ile Leu Asp Met Pro Trp Asn Glu Ser Glu Leu
465                 470                 475                 480

Lys Gln Ile Ile Gly
                485


<210> SEQ ID NO 43
<211> LENGTH: 235
<212> TYPE: DNA
<213> ORGANISM: Choristoneura biennis entomopoxvirus

<400> SEQUENCE: 43

aaaagtttga taaatcacat ttaaaaattg ttatgcataa tagaggaagt ggtaatgtat     60

tccctattag atcactatat ttggaattat tgaacgtcaa aggttatcct gtaaaagcat    120

ccgatacgtc taggttagat gttggtgttt ataaactaaa taaaatatat attgataatg    180

atgaaaataa aataatttta gaagaaattg aaaccgatta tagatgtgga agaga         235


<210> SEQ ID NO 44
<211> LENGTH: 77
<212> TYPE: PRT
<213> ORGANISM: Choristoneura biennis entomopoxvirus

<400> SEQUENCE: 44

Lys Phe Asp Lys Ser His Leu Lys Ile Val Met His Asn Arg Gly Ser
1               5                   10                  15

Gly Asn Val Phe Pro Ile Arg Ser Leu Tyr Leu Glu Leu Leu Asn Val
            20                  25                  30

Lys Gly Tyr Pro Val Lys Ala Ser Asp Thr Ser Arg Leu Asp Val Gly
        35                  40                  45

Val Tyr Lys Leu Asn Lys Ile Tyr Ile Asp Asn Asp Glu Asn Lys Ile
    50                  55                  60

Ile Leu Glu Glu Ile Glu Thr Asp Tyr Arg Cys Gly Arg
65                  70                  75


<210> SEQ ID NO 45
<211> LENGTH: 235
<212> TYPE: DNA
<213> ORGANISM: Choristoneura fumiferana entomopoxvirus

<400> SEQUENCE: 45

aaaagtttga taaatcacat ttaaaaatcg ttatgcacaa tagaggaagc ggtaatgtat     60

tccctattag atcactatat ttggaattat tgaacgtcaa aggttatcct gttaaagcat    120

ccgatacgtc taggttagac gttggtgttt ataaactaaa taaaatatat attgataatg    180

atgaaaataa aataatttta gaagaaatcg aaaccgatta tagatgtgga agaga         235
```

-continued

<210> SEQ ID NO 46
<211> LENGTH: 77
<212> TYPE: PRT
<213> ORGANISM: Choristoneura fumiferana entomopoxvirus

<400> SEQUENCE: 46

```
Lys Phe Asp Lys Ser His Leu Lys Ile Val Met His Asn Arg Gly Ser
1               5                   10                  15

Gly Asn Val Phe Pro Ile Arg Ser Leu Tyr Leu Glu Leu Leu Asn Val
            20                  25                  30

Lys Gly Tyr Pro Val Lys Ala Ser Asp Thr Ser Arg Leu Asp Val Gly
        35                  40                  45

Val Tyr Lys Leu Asn Lys Ile Tyr Ile Asp Asn Asp Glu Asn Lys Ile
    50                  55                  60

Ile Leu Glu Glu Ile Glu Thr Asp Tyr Arg Cys Gly Arg
65                  70                  75
```

<210> SEQ ID NO 47
<211> LENGTH: 10
<212> TYPE: PRT
<213> ORGANISM: Choristoneura biennis entomopoxvirus

<400> SEQUENCE: 47

```
Lys Phe Lys Tyr Leu Phe Leu Lys Asn Lys
1               5                   10
```

<210> SEQ ID NO 48
<211> LENGTH: 11
<212> TYPE: PRT
<213> ORGANISM: Choristoneura biennis entomopoxvirus

<400> SEQUENCE: 48

```
Lys Ser Val Asn Ile Ala Val Ser Phe Leu Asp
1               5                   10
```

<210> SEQ ID NO 49
<211> LENGTH: 11
<212> TYPE: PRT
<213> ORGANISM: Choristoneura biennis entomopoxvirus

<400> SEQUENCE: 49

```
Lys Tyr Leu Val Asp Ser Ser Val Gln Ser Gln
1               5                   10
```

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide RM206.

<400> SEQUENCE: 50

```
agatgatgat taaagtgtgg                                                   20
```

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide RM212.

<400> SEQUENCE: 51

```
gataatgata ctccggttgc                                                   20
```

-continued

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide RM58.
<221> NAME/KEY: misc_feature
<222> LOCATION: (6)..(6)
<223> OTHER INFORMATION: N = A, C, G, or T.
<221> NAME/KEY: misc_feature
<222> LOCATION: (12)..(12)
<223> OTHER INFORMATION: N = A, C, G, or T.

<400> SEQUENCE: 52
gaagtngatc cngaatatgt 20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide RM75.

<400> SEQUENCE: 53
gaaaataaaa ttatattgga 20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide RM76.

<400> SEQUENCE: 54
agacaattcc agatataatg 20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide RM78.

<400> SEQUENCE: 55
ccgcatctat attctgcttc 20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide RM79.

<400> SEQUENCE: 56
gtttaaaacc taaagtaccc 20

<210> SEQ ID NO 57
<211> LENGTH: 20
<212> TYPE: DNA
<213> ORGANISM: Artificial Sequence
<220> FEATURE:
<223> OTHER INFORMATION: Synthetic oligonucleotide RM87.

<400> SEQUENCE: 57
gttgcatctg tagttacatc 20

-continued

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide RM91.

<400> SEQUENCE: 58
tctagcaata atcgacttac 20

<210> SEQ ID NO 59
<211> LENGTH: 20
<212> TYPE: DNA
<213> ORGANISM: Artificial Sequence
<220> FEATURE:
<223> OTHER INFORMATION: Synthetic oligonucleotide RM93.

<400> SEQUENCE: 59
catttctatt aagcctaacg 20

<210> SEQ ID NO 60
<211> LENGTH: 20
<212> TYPE: DNA
<213> ORGANISM: Artificial Sequence
<220> FEATURE:
<223> OTHER INFORMATION: Synthetic oligonucleotide RM95.

<400> SEQUENCE: 60
gtacctttag caaccaaaac 20

<210> SEQ ID NO 61
<211> LENGTH: 20
<212> TYPE: DNA
<213> ORGANISM: Artificial Sequence
<220> FEATURE:
<223> OTHER INFORMATION: Synthetic oligonucleotide RM169.

<400> SEQUENCE: 61
aattgcacat tatcattggg 20

<210> SEQ ID NO 62
<211> LENGTH: 20
<212> TYPE: DNA
<213> ORGANISM: Artificial Sequence
<220> FEATURE:
<223> OTHER INFORMATION: Synthetic oligonucleotide RM170.

<400> SEQUENCE: 62
attacccaat gataatgtgc 20

<210> SEQ ID NO 63
<211> LENGTH: 29
<212> TYPE: DNA
<213> ORGANISM: Artificial Sequence
<220> FEATURE:
<223> OTHER INFORMATION: Synthetic oligonucleotide RM282.

<400> SEQUENCE: 63
ccggaattcc ataatctaca cacaggaac 29

<210> SEQ ID NO 64
<211> LENGTH: 29
<212> TYPE: DNA
<213> ORGANISM: Artificial Sequence
<220> FEATURE:
<223> OTHER INFORMATION: Synthetic oligonucleotide RM283.

-continued

<400> SEQUENCE: 64
ccggaattcg tcgatagaat taataattg 29

<210> SEQ ID NO 65
<211> LENGTH: 30
<212> TYPE: DNA
<213> ORGANISM: Artificial Sequence
<220> FEATURE:
<223> OTHER INFORMATION: Synthetic oligonucleotide pTk1.

<400> SEQUENCE: 65
acaggagctc gaattcaagt taaatattta 30

<210> SEQ ID NO 66
<211> LENGTH: 30
<212> TYPE: DNA
<213> ORGANISM: Artificial Sequence
<220> FEATURE:
<223> OTHER INFORMATION: Synthetic oligonucleotide pTk2.

<400> SEQUENCE: 66
cacaggatcc ctggcaaaac aacagaattg 30

<210> SEQ ID NO 67
<211> LENGTH: 31
<212> TYPE: DNA
<213> ORGANISM: Artificial Sequence
<220> FEATURE:
<223> OTHER INFORMATION: Synthetic oligonucleotide pTk3.

<400> SEQUENCE: 67
agagaagctt caaaatggat ttactaaatt c 31

<210> SEQ ID NO 68
<211> LENGTH: 30
<212> TYPE: DNA
<213> ORGANISM: Artificial Sequence
<220> FEATURE:
<223> OTHER INFORMATION: Synthetic oligonucleotide pTk4.

<400> SEQUENCE: 68
cacagttaac gaattcatat tcaattatat 30

<210> SEQ ID NO 69
<211> LENGTH: 30
<212> TYPE: DNA
<213> ORGANISM: Artificial Sequence
<220> FEATURE:
<223> OTHER INFORMATION: Synthetic oligonucleotide pU.

<400> SEQUENCE: 69
acaggagctc gctattataa ctaatgtgag 30

<210> SEQ ID NO 70
<211> LENGTH: 30
<212> TYPE: DNA
<213> ORGANISM: Artificial Sequence
<220> FEATURE:
<223> OTHER INFORMATION: Synthetic oligonucleotide pU2.

<400> SEQUENCE: 70
cacaggatcc ctcatttatt attattaata 30

<210> SEQ ID NO 71

-continued

<211> LENGTH: 30
<212> TYPE: DNA
<213> ORGANISM: Artificial Sequence
<220> FEATURE:
<223> OTHER INFORMATION: Synthetic oligonucleotide pU20.

<400> SEQUENCE: 71
cacaggatcc gttgctaaag gtacgttact 30

<210> SEQ ID NO 72
<211> LENGTH: 30
<212> TYPE: DNA
<213> ORGANISM: Artificial Sequence
<220> FEATURE:
<223> OTHER INFORMATION: Synthetic oligonucleotide pD1.

<400> SEQUENCE: 72
agagaagctt cagcccagat actacgattc 30

<210> SEQ ID NO 73
<211> LENGTH: 30
<212> TYPE: DNA
<213> ORGANISM: Artificial Sequence
<220> FEATURE:
<223> OTHER INFORMATION: Synthetic oligonucleotide pD2.

<400> SEQUENCE: 73
cacagttaac acacttgatg caactctagc 30

<210> SEQ ID NO 74
<211> LENGTH: 1947
<212> TYPE: DNA
<213> ORGANISM: Amsacta moorei entomopoxvirus

<400> SEQUENCE: 74
ctattcataa taatcatctg ctatatatat taatgtatca ttctctatta taaatatagg 60
tatattgtct ttatcaatca ttaattttgc tacagctgta ttatctttat atactatatt 120
tgtgtctttg tttaataaac cttttaatat agtggctcta tcataatctt tacaatatga 180
tatgggatat aattttatat taataataac attagatacg ttcatttctt tcattctagt 240
tttacgtatt gtgtcaaaaa ttatttcatt ttctgctggt tctatatatt tatatgtgtt 300
atgaatagat tcgatagatg atgattttaa taaatcaaat ataacattta ttttaccttg 360
tttatctttt ataatatcta atatttcttt atctacagat tttctgttgt tggtatatga 420
tattaaaaaa tgaacgttaa catatctata ttcttgtggt aaatctttat gagaatttaa 480
tcttatagat cttcctatta tttgttttaa ttctgattca ttccacggca tatctaatat 540
aattatatca ttaatacatt tgaatgatat gccttcagat ccagcgtaag aaaatatgca 600
aacttttact tttttaccat tattattttc ataattatta tattcgttta attcattatc 660
tctagttttt aaagttttgc tagaatattc aatataagaa atattaaaac aattaaaata 720
acattttaaa cttgatattc cttcaaaatt aactaaaggt tcaaatatta atacttttcc 780
tctcgaattt aaaattattt tacaagtttc tatatattta cacgaatatt gatataatat 840
attataatta tttatatcag tgattggtaa attagttttt atttttatat tatcattttt 900
aaaactttca ataaaagatt cagagaaatt aatatttttt gtaaactcgg aaaattcagc 960
aagttttctt ttaatcatat cattatattc tatattatct aaatctcctt ttattttaag 1020
atcataaaaa gcaaatgaag atattaatct tctcatagtt tttaaaccac ctaattcagt 1080
tttataatca tatttttctg ccatattata taatttagat tgctcatctg acataattat 1140

-continued

```
attatgataa aatatatttt tttttgcata tccatctata taatttgttt ctgttaaact   1200

atctgcttct attaatcttt tataagaaca tatagctaat aatgtttctc ttaattcctt   1260

aaaattaatt aactttccat tatttatata ttcttctttt atattcataa catttggtct   1320

aagtaaacct attaaattat taaattcaga aatattatta gttactggag tagcggacat   1380

acataatatt ttattatttt cgaaatttgc taattttatt aattttttat aaataggagt   1440

aaaatttctt tcgttattat cttttttaac agttcttgat attaatttat gaacttcgtc   1500

tattattatt agtaatctac tttttttatt aagagaactt tctatagatc tatatatatt   1560

attaaattta tctaaactag atgacgaatc ataatatata aattttatat tactggtatc   1620

tgatatatat gatcttatag tatttaacca aggatctatg tataatgatt ttttaataaa   1680

tattaaaatt atccatcttg gaaataattc ttttatatat tttataatat acacagcagt   1740

taatgttttt cccataccag tatcccaaaa taataacata ctattcaaat tttttaatcc   1800

tatgaatatt ctacttacaa aatattgata atcttgtaat gtaatttcag tatttgtaat   1860

attattcata attttattag gcaaatgttg tgttttatca agtgcataat ttatatgttt   1920

accaacaata gaatctaatg caaacat                                        1947
```

<210> SEQ ID NO 75
<211> LENGTH: 648
<212> TYPE: PRT
<213> ORGANISM: Amsacta moorei entomopoxvirus

<400> SEQUENCE: 75

```
Met Phe Ala Leu Asp Ser Ile Val Gly Lys His Ile Asn Tyr Ala Leu
1               5                   10                  15

Asp Lys Thr Gln His Leu Pro Asn Lys Ile Met Asn Asn Ile Thr Asn
            20                  25                  30

Thr Glu Ile Thr Leu Gln Asp Tyr Gln Tyr Phe Val Ser Arg Ile Phe
        35                  40                  45

Ile Gly Leu Lys Asn Leu Asn Ser Met Leu Leu Phe Trp Asp Thr Gly
    50                  55                  60

Met Gly Lys Thr Leu Thr Ala Val Tyr Ile Ile Lys Tyr Ile Lys Glu
65                  70                  75                  80

Leu Phe Pro Arg Trp Ile Ile Leu Ile Phe Ile Lys Lys Ser Leu Tyr
                85                  90                  95

Ile Asp Pro Trp Leu Asn Thr Ile Arg Ser Tyr Ile Ser Asp Thr Ser
            100                 105                 110

Asn Ile Lys Phe Ile Tyr Tyr Asp Ser Ser Ser Ser Leu Asp Lys Phe
        115                 120                 125

Asn Asn Ile Tyr Arg Ser Ile Glu Ser Ser Leu Asn Lys Lys Ser Arg
    130                 135                 140

Leu Leu Ile Ile Ile Asp Glu Val His Lys Leu Ile Ser Arg Thr Val
145                 150                 155                 160

Lys Lys Asp Asn Asn Glu Arg Asn Phe Thr Pro Ile Tyr Lys Lys Leu
                165                 170                 175

Ile Lys Leu Ala Asn Phe Glu Asn Asn Lys Ile Leu Cys Met Ser Ala
            180                 185                 190

Thr Pro Val Thr Asn Asn Ile Ser Glu Phe Asn Asn Leu Ile Gly Leu
        195                 200                 205

Leu Arg Pro Asn Val Met Asn Ile Lys Glu Glu Tyr Ile Asn Asn Gly
    210                 215                 220
```

-continued

```
Lys Leu Ile Asn Phe Lys Glu Leu Arg Glu Thr Leu Leu Ala Ile Cys
225                 230                 235                 240

Ser Tyr Lys Arg Leu Ile Glu Ala Asp Ser Leu Thr Glu Thr Asn Tyr
                245                 250                 255

Ile Asp Gly Tyr Ala Lys Lys Asn Ile Phe Tyr His Asn Ile Ile Met
            260                 265                 270

Ser Asp Glu Gln Ser Lys Leu Tyr Asn Met Ala Glu Lys Tyr Asp Tyr
        275                 280                 285

Lys Thr Glu Leu Gly Gly Leu Lys Thr Met Arg Arg Leu Ile Ser Ser
    290                 295                 300

Phe Ala Phe Tyr Asp Leu Lys Ile Lys Gly Asp Leu Asp Asn Ile Glu
305                 310                 315                 320

Tyr Asn Asp Met Ile Lys Arg Lys Leu Ala Glu Phe Ser Glu Phe Thr
                325                 330                 335

Lys Asn Ile Asn Phe Ser Glu Ser Phe Ile Glu Ser Phe Lys Asn Asp
            340                 345                 350

Asn Ile Lys Ile Lys Thr Asn Leu Pro Ile Thr Asp Ile Asn Asn Tyr
        355                 360                 365

Asn Ile Leu Tyr Gln Tyr Ser Cys Lys Tyr Ile Glu Thr Cys Lys Ile
    370                 375                 380

Ile Leu Asn Ser Arg Gly Lys Val Leu Ile Phe Glu Pro Leu Val Asn
385                 390                 395                 400

Phe Glu Gly Ile Ser Ser Leu Lys Cys Tyr Phe Asn Cys Phe Asn Ile
                405                 410                 415

Ser Tyr Ile Glu Tyr Ser Ser Lys Thr Leu Lys Thr Arg Asp Asn Glu
            420                 425                 430

Leu Asn Glu Tyr Asn Asn Tyr Glu Asn Asn Asn Gly Lys Lys Val Lys
        435                 440                 445

Val Cys Ile Phe Ser Tyr Ala Gly Ser Glu Gly Ile Ser Phe Lys Cys
    450                 455                 460

Ile Asn Asp Ile Ile Ile Leu Asp Met Pro Trp Asn Glu Ser Glu Leu
465                 470                 475                 480

Lys Gln Ile Ile Gly Arg Ser Ile Arg Leu Asn Ser His Lys Asp Leu
                485                 490                 495

Pro Gln Glu Tyr Arg Tyr Val Asn Val His Phe Leu Ile Ser Tyr Thr
            500                 505                 510

Asn Asn Arg Lys Ser Val Asp Lys Glu Ile Leu Asp Ile Ile Lys Asp
        515                 520                 525

Lys Gln Gly Lys Ile Asn Val Ile Phe Asp Leu Leu Lys Ser Ser Ser
    530                 535                 540

Ile Glu Ser Ile His Asn Thr Tyr Lys Tyr Ile Glu Pro Ala Glu Asn
545                 550                 555                 560

Glu Ile Ile Phe Asp Thr Ile Arg Lys Thr Arg Met Lys Glu Met Asn
                565                 570                 575

Val Ser Asn Val Ile Ile Asn Ile Lys Leu Tyr Pro Ile Ser Tyr Cys
            580                 585                 590

Lys Asp Tyr Asp Arg Ala Thr Ile Leu Lys Gly Leu Leu Asn Lys Asp
        595                 600                 605

Thr Asn Ile Val Tyr Lys Asp Asn Thr Ala Val Ala Lys Leu Met Ile
    610                 615                 620

Asp Lys Asp Asn Ile Pro Ile Phe Ile Ile Glu Asn Asp Thr Leu Ile
625                 630                 635                 640

Tyr Ile Ala Asp Asp Tyr Tyr Glu
```

-continued

```
                645


<210> SEQ ID NO 76
<211> LENGTH: 235
<212> TYPE: DNA
<213> ORGANISM: Amsacta moorei entomopoxvirus

<400> SEQUENCE: 76

aaaagtttga taaatctcat ttaaaaattg taatgcataa cagaggaagt ggtaatgtat      60

ttccattaag atcattatat ctggaattgt ctaatgtaaa aggatatcca gttaaagcat     120

ctgatacttc gagattagat gttggtattt acaaattaaa taaaatttat gtagataacg     180

acgaaaataa aattatattg gaagaaattg aagcagaata tagatgcgga agaca          235


<210> SEQ ID NO 77
<211> LENGTH: 77
<212> TYPE: PRT
<213> ORGANISM: Amsacta moorei entomopoxvirus

<400> SEQUENCE: 77

Lys Phe Asp Lys Ser His Leu Lys Ile Val Met His Asn Arg Gly Ser
1               5                   10                  15

Gly Asn Val Phe Pro Leu Arg Ser Leu Tyr Leu Glu Leu Ser Asn Val
            20                  25                  30

Lys Gly Tyr Pro Val Lys Ala Ser Asp Thr Ser Arg Leu Asp Val Gly
        35                  40                  45

Ile Tyr Lys Leu Asn Lys Ile Tyr Val Asp Asn Asp Glu Asn Lys Ile
    50                  55                  60

Ile Leu Glu Glu Ile Glu Ala Glu Tyr Arg Cys Gly Arg
65                  70                  75


<210> SEQ ID NO 78
<211> LENGTH: 20
<212> TYPE: DNA
<213> ORGANISM: Amsacta moorei entomopoxvirus

<400> SEQUENCE: 78

gaagtagacc ccgagtatgt                                                  20
```